(12) United States Patent
Mehta et al.

(10) Patent No.: US 12,414,850 B2
(45) Date of Patent: Sep. 16, 2025

(54) SYSTEMS, DEVICES, AND METHODS FOR THE RETRIEVAL OF AN IMPLANT IN THE PROSTATIC URETHRA

(71) Applicant: ZENFLOW, INC., San Francisco, CA (US)

(72) Inventors: Shreya Mehta, San Francisco, CA (US); Aaron M. Weiss, Oakland, CA (US); Austin Michael Bly, San Clemente, CA (US)

(73) Assignee: ZENFLOW, INC., San Francisco, CA (US)

( * ) Notice: Subject to any disclaimer, the term of this patent is extended or adjusted under 35 U.S.C. 154(b) by 952 days.

(21) Appl. No.: 17/495,996

(22) Filed: Oct. 7, 2021

(65) Prior Publication Data

US 2022/0110737 A1   Apr. 14, 2022

Related U.S. Application Data

(60) Provisional application No. 63/089,205, filed on Oct. 8, 2020.

(51) Int. Cl.
*A61F 2/95* (2013.01)
*A61B 17/00* (2006.01)
*A61F 2/04* (2013.01)

(52) U.S. Cl.
CPC .......... *A61F 2/04* (2013.01); *A61B 17/00234* (2013.01); *A61B 2017/00274* (2013.01); *A61F 2002/047* (2013.01)

(58) Field of Classification Search
CPC ...... A61F 2002/9528; A61F 2002/9534; A61F 2002/047; A61F 2002/046–2002/048; A61F 2/95; A61F 2002/9505–2002/9511
See application file for complete search history.

(56) References Cited

U.S. PATENT DOCUMENTS

| | | | | |
|---|---|---|---|---|
| 5,941,895 A | * | 8/1999 | Myler | A61F 2/95 606/198 |
| 11,571,290 B2 | * | 2/2023 | Bachar | A61F 2/04 |
| 12,076,226 B2 | * | 9/2024 | Bachar | A61F 2/9517 |
| 2002/0120277 A1 | * | 8/2002 | Hauschild | A61F 2/95 606/108 |
| 2002/0161427 A1 | * | 10/2002 | Rabkin | A61F 2/95 623/1.11 |

(Continued)

FOREIGN PATENT DOCUMENTS

| | | |
|---|---|---|
| CN | 102 438 533 B | 11/2014 |
| CN | 108836587 A | 11/2018 |

(Continued)

OTHER PUBLICATIONS

EP, 21878507.9 Extended Search Report, Oct. 10, 2024.
WO, PCT/US21/53904 ISR and Written Opinion, Feb. 17, 2022.
JP, 2023-521338 Office Action, Jul. 1, 2025.

*Primary Examiner* — Alvin J Stewart
(74) *Attorney, Agent, or Firm* — ONE LLP

(57) ABSTRACT

Systems, devices, and methods are provided for retrieval of an implant from the prostatic urethra. Embodiments of retrieval systems can include a device for insertion into the patient and a proximal control device for use in grasping a portion of the implant and withdrawing the implant into a lumen of the retrieval system.

12 Claims, 37 Drawing Sheets

(56) References Cited

U.S. PATENT DOCUMENTS

| | | | |
|---|---|---|---|
| 2002/0188344 A1* | 12/2002 | Bolea | A61F 2/95 623/1.11 |
| 2005/0131423 A1* | 6/2005 | Yachia | A61F 2/95 606/108 |
| 2005/0131515 A1* | 6/2005 | Cully | A61F 2/07 623/1.13 |
| 2007/0186933 A1 | 8/2007 | Domingo et al. | |
| 2010/0094327 A1* | 4/2010 | Milsom | A61B 17/0218 606/191 |
| 2011/0054519 A1 | 3/2011 | Neuss | |
| 2015/0257908 A1 | 9/2015 | Chao et al. | |
| 2016/0030047 A1 | 2/2016 | Allen et al. | |
| 2016/0206449 A1* | 7/2016 | Mort | A61F 2/86 |
| 2016/0346107 A1* | 12/2016 | Matthison-Hansen | A61B 17/30 |
| 2017/0065299 A1 | 3/2017 | Gillespie et al. | |
| 2019/0038443 A1 | 2/2019 | Sicotte et al. | |
| 2019/0099280 A1 | 4/2019 | Ben Muvhar | |
| 2019/0117423 A1 | 4/2019 | Chao et al. | |
| 2019/0175199 A1 | 6/2019 | Girdhar et al. | |
| 2019/0307548 A1 | 10/2019 | Sicotte et al. | |
| 2020/0038213 A1 | 2/2020 | Bly et al. | |
| 2020/0164188 A1 | 5/2020 | Chang et al. | |
| 2020/0323618 A1 | 10/2020 | Bly et al. | |
| 2021/0137711 A1* | 5/2021 | Fukumoto | A61F 2/9522 |
| 2021/0145619 A1 | 5/2021 | Bly et al. | |
| 2021/0161641 A1* | 6/2021 | Bachar | A61F 2/962 |
| 2021/0161642 A1* | 6/2021 | Jen | A61B 1/0008 |
| 2021/0251789 A1* | 8/2021 | Ouyang | A61B 1/00052 |
| 2021/0275335 A1 | 9/2021 | Sicotte et al. | |
| 2022/0110737 A1* | 4/2022 | Mehta | A61F 2/95 |
| 2024/0115405 A1* | 4/2024 | Kadlec | A61F 2/86 |

FOREIGN PATENT DOCUMENTS

| | | | | |
|---|---|---|---|---|
| EP | 1 917 922 A1 | 5/2008 | | |
| JP | H1076015 A | * 3/1998 | | A61B 17/221 |
| WO | WO 2017/184887 A1 | 10/2017 | | |
| WO | WO 2019/222481 A1 | 11/2019 | | |
| WO | WO 2020/142846 A1 | 7/2020 | | |
| WO | WO 2021/101951 A1 | 5/2021 | | |

* cited by examiner

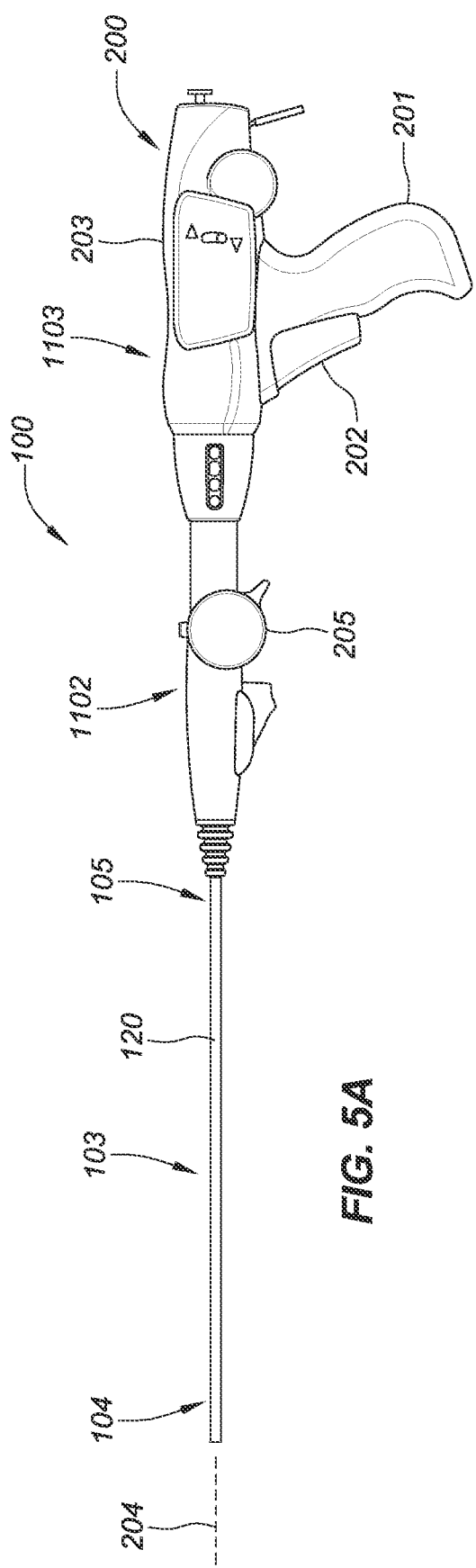
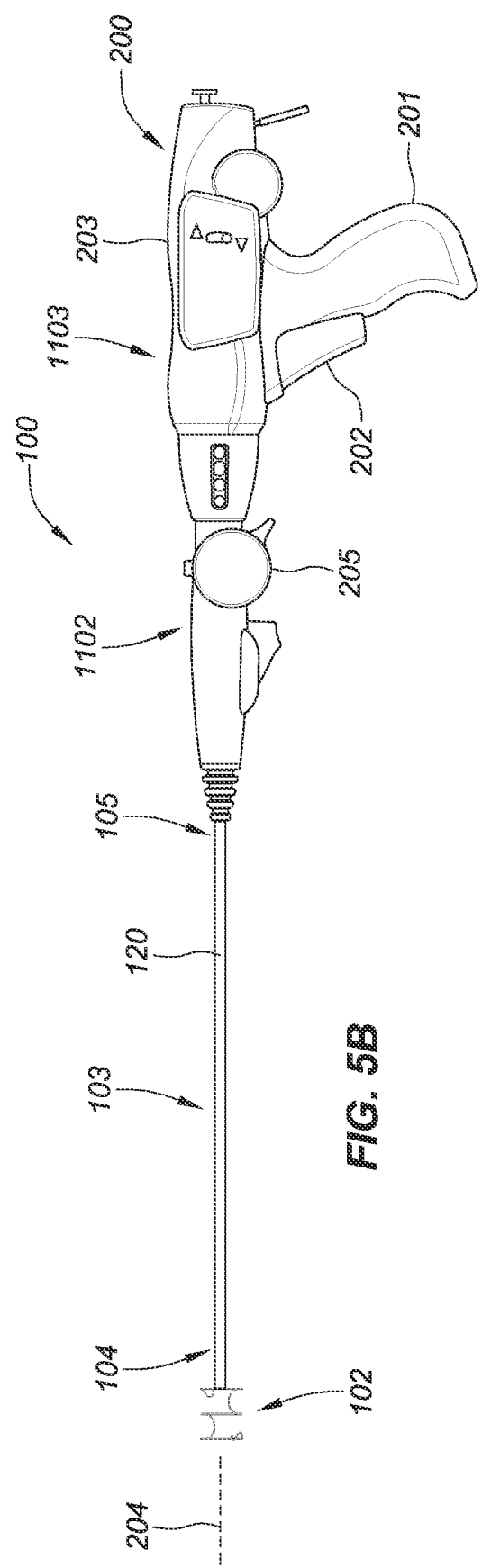
FIG. 5A
FIG. 5B

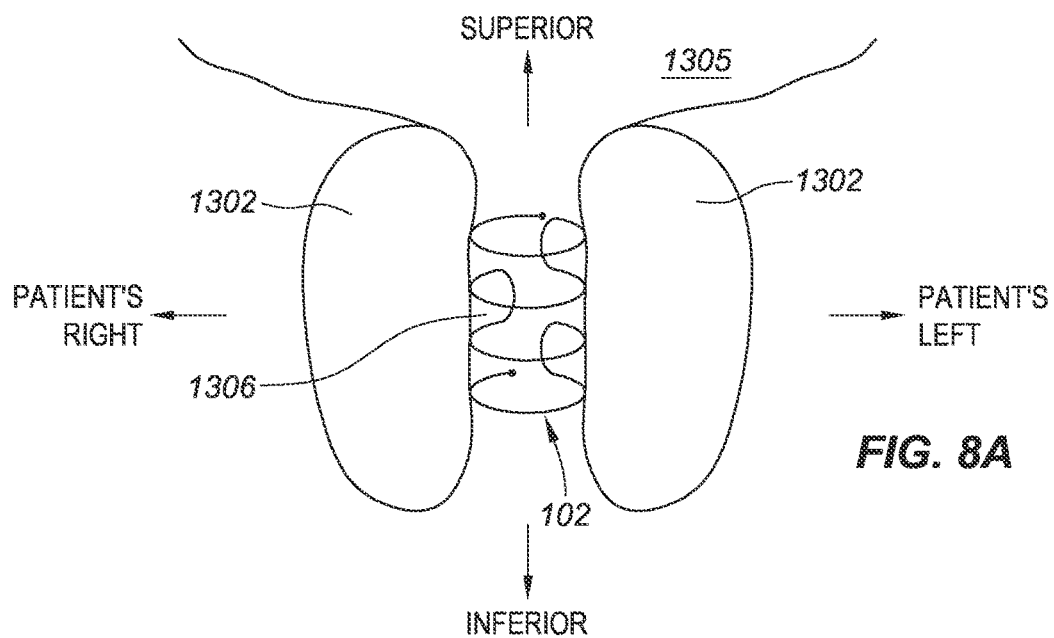
FIG. 8A
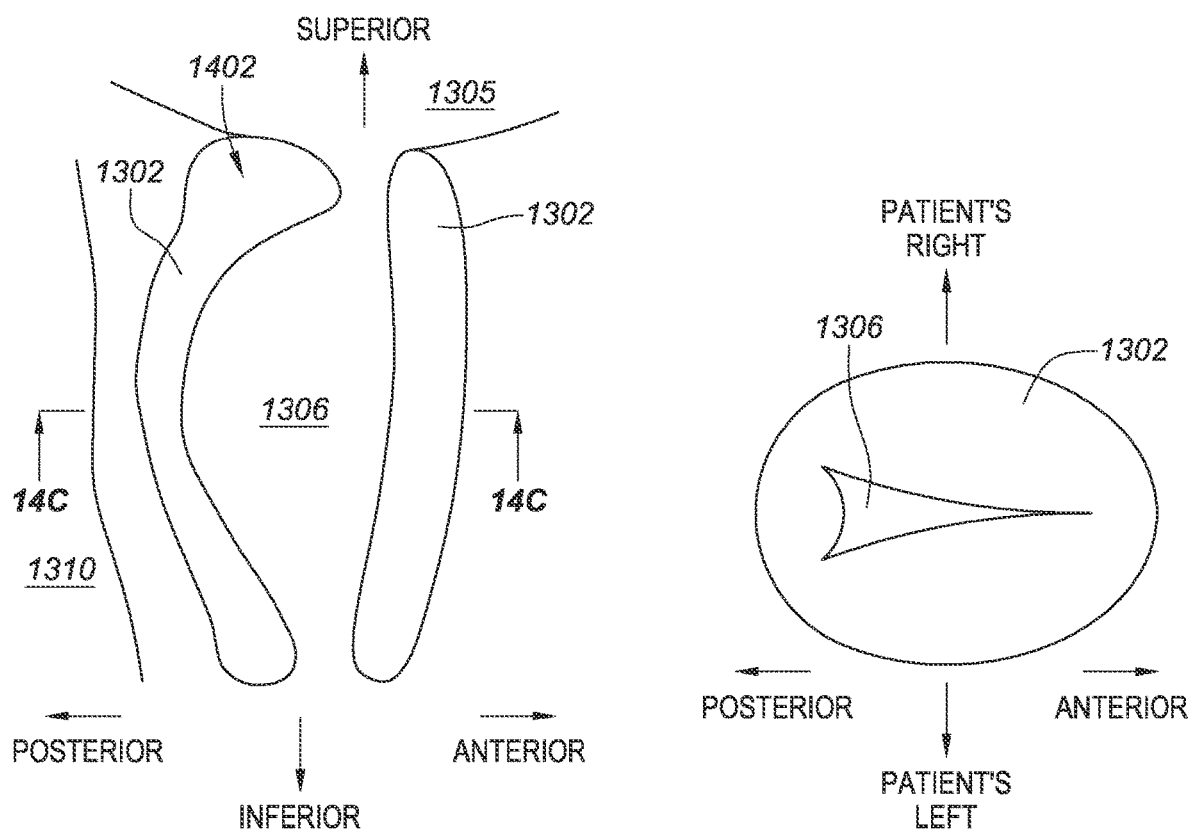
FIG. 8B
FIG. 8C

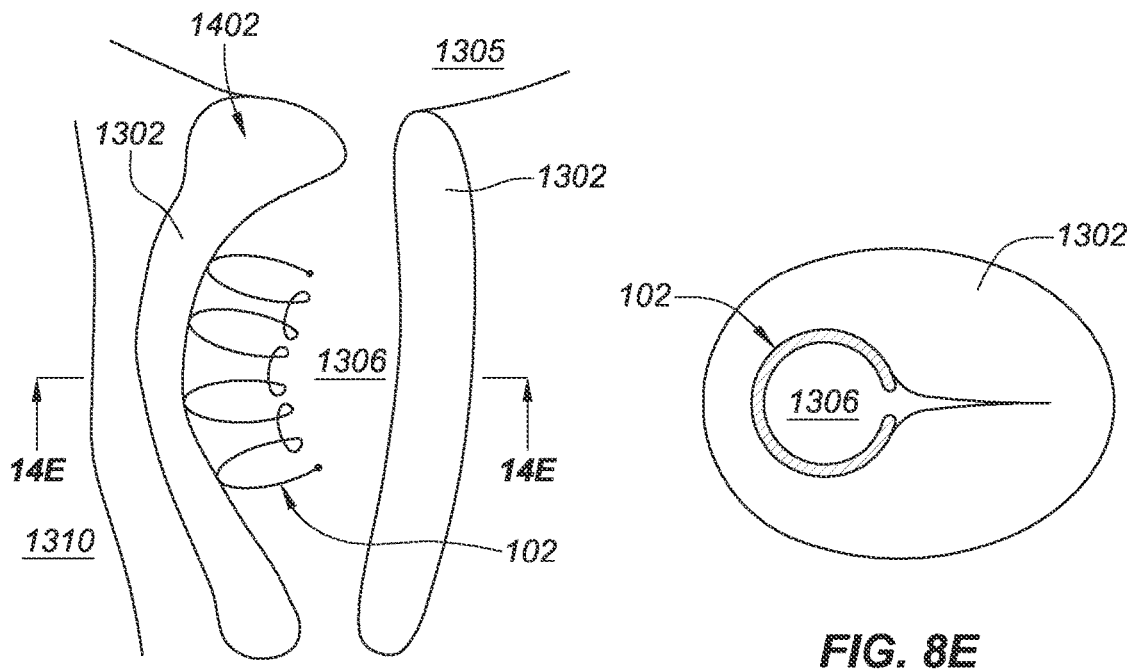
FIG. 8D
FIG. 8E
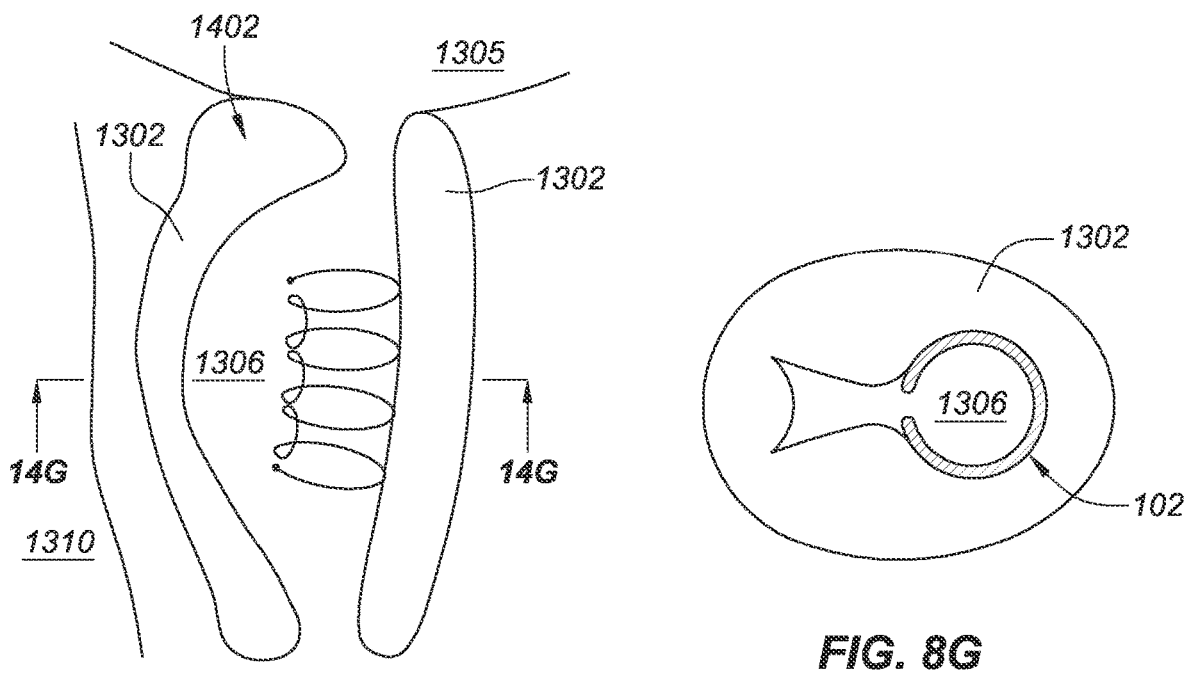
FIG. 8F
FIG. 8G

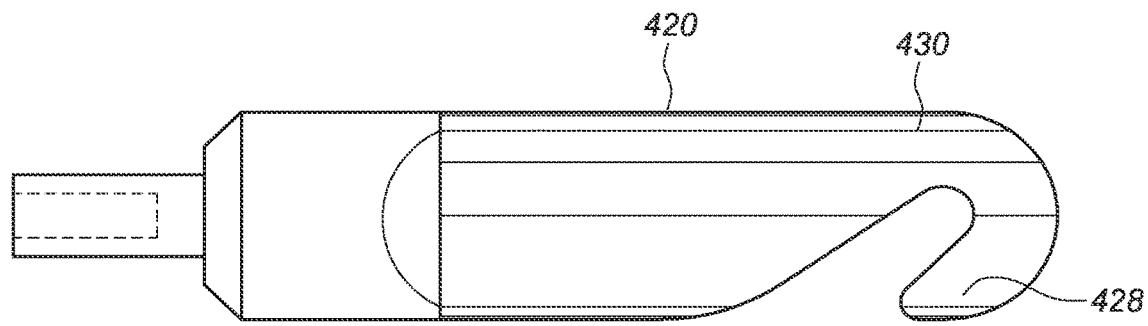
FIG. 15A
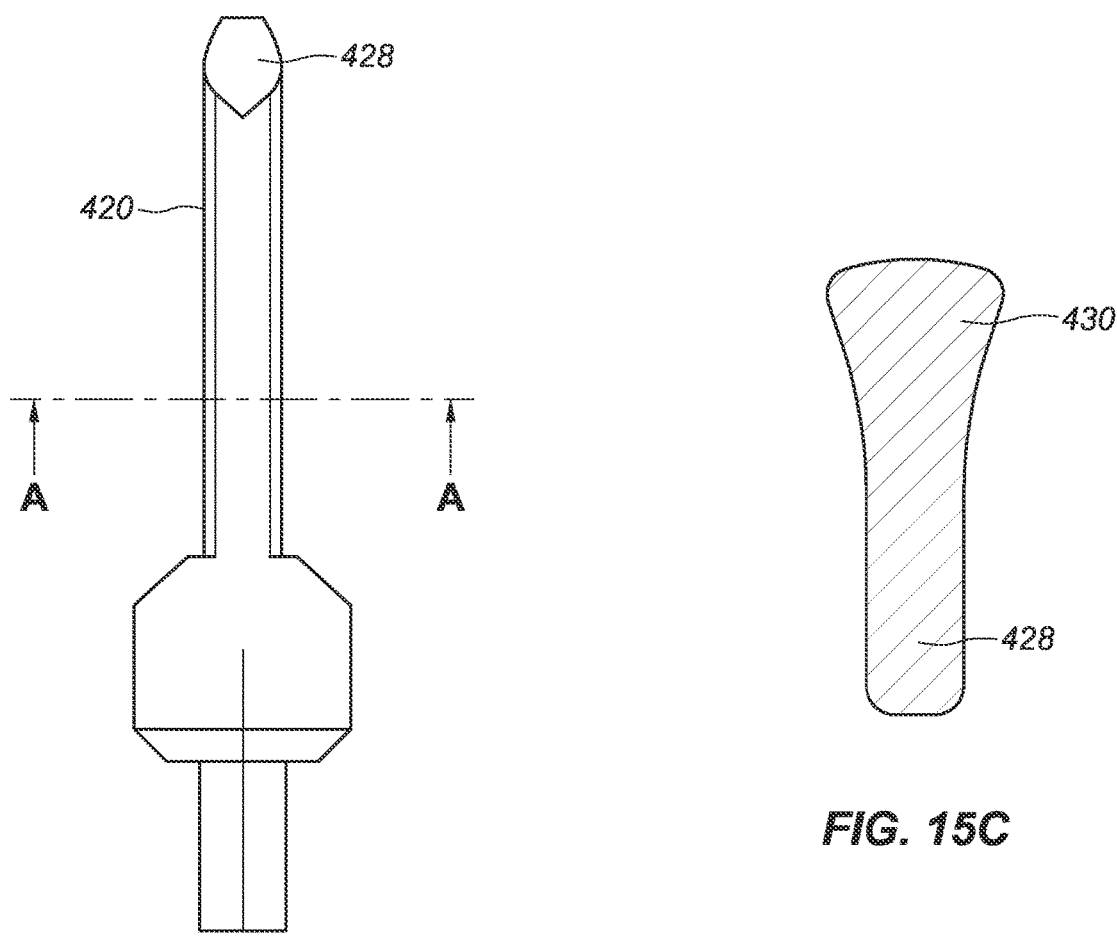
FIG. 15B
FIG. 15C

SYSTEMS, DEVICES, AND METHODS FOR THE RETRIEVAL OF AN IMPLANT IN THE PROSTATIC URETHRA

CROSS-REFERENCE TO RELATED APPLICATIONS

This application claims priority to, and the benefit of, U.S. Provisional Application No. 63/089,205, filed Oct. 8, 2020, which is hereby expressly incorporated by reference in its entirety for all purposes.

STATEMENT OF GOVERNMENT SPONSOR RESEARCH

This invention was made with government support under NIH SBIR Phase II R44DK124094 awarded by the National Institutes of Health. The government has certain rights in the invention.

FIELD

The subject matter described herein relates to systems, devices, and methods for delivery or deployment of an implant into the prostatic urethra, more specifically, delivery in an atraumatic and minimally-invasive manner through the tortuous bends of the male urethra.

BACKGROUND

There are numerous clinical reasons for placement of an implant into the prostatic urethra, such as for treatment of urinary retention associated with benign prostatic hyperplasia (BPH), blockages from prostate cancer, bladder cancer, urinary tract injury, prostatitis, bladder sphincter dyssynergia, benign or malignant urethral stricture, and other conditions for which treatment is desired. Due to the naturally complex and tortuous anatomical geometry, patient-to-patient geometric and tissue variability, and anatomical restrictions associated with those conditions, accurate and consistent placement of an implant into the prostatic urethral lumen has proven challenging. Furthermore, complex challenges are presented in the design and/or fabrication of systems with sufficient flexibility to deliver such an implant in a minimally-invasive manner. For these and other reasons, needs exist for improved systems, devices, and methods of implant delivery to the prostatic urethra.

SUMMARY

Provided herein are a number of example embodiments of delivery systems for delivering or deploying implants within the prostatic urethra or other parts of the body, and methods related thereto. Embodiments of the delivery system can include a delivery device insertable into the prostatic urethra and a proximal control device coupled with the delivery device and configured to control deployment of one or more implants from the delivery device. In some embodiments, the delivery device can include multiple tubular components each having various functions described in more detail herein. Embodiments of the delivery system have imaging capabilities. Multiple embodiments of implants for use with the delivery systems are also described, as are various implanted placements of those implants.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 5A-5B are side views depicting an example embodiment of a delivery system in various stages of deployment of an implant.

FIG. 8A is an example cross-section of the male anatomy having an example embodiment of an implant deployed therein.

FIG. 8B is an example cross-section of the male anatomy.

FIG. 8C is an example cross-section of the male anatomy taken along line 8C-8C of FIG. 8B.

FIG. 8D is an example cross-section of the male anatomy having an example embodiment of an implant deployed therein and FIG. 8E is an example cross-section of the male anatomy taken along line 8E-8E of FIG. 8D.

FIG. 8F is an example cross-section of the male anatomy having an example embodiment of an implant deployed therein and FIG. 8G is an example cross-section of the male anatomy taken along line 8F-8F of FIG. 8G.

FIGS. 15A-15B are example embodiments of a hook of a retrieval device.

FIG. 15C is an example cross-section of a hook of a retrieval device.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The subject matter presented herein is described in the context of delivery or deployment of one or more implants within the prostatic urethra. The purpose for deployment of the implant(s) in the prostatic urethra can vary. The embodiments described herein are particularly suited for treatment of BPH, but they are not limited to such. Other conditions for which these embodiments can be used include, but are not limited to, treatment of blockages from prostate cancer, bladder cancer, urinary tract injury, prostatitis, bladder sphincter dyssynergia, and/or benign or malignant urethral stricture. Further, these embodiments can have applicability for deployment of one or more implants in other locations of the urinary tract or in the bladder, as well as other biological lumens, cavities, or spaces, such as the human vasculature, cardiac system, pulmonary system, or gastro-intestinal tract, including locations within the heart, stomach, intestines, liver, spleen, pancreas, and kidney.

The subject matter presented herein further describes methods for removing the implant from the prostatic urethra. Although the implant is intended to be a permanent implant, removal is required under certain circumstances, such as initial implant misplacement, implant migration, safety issues, or efficacy issues. The methods of removal described herein are simple and do not cause any permanent tissue damage. The device can be removed acutely (during a procedure) or chronically (after years of implantation).

Figure 1A:
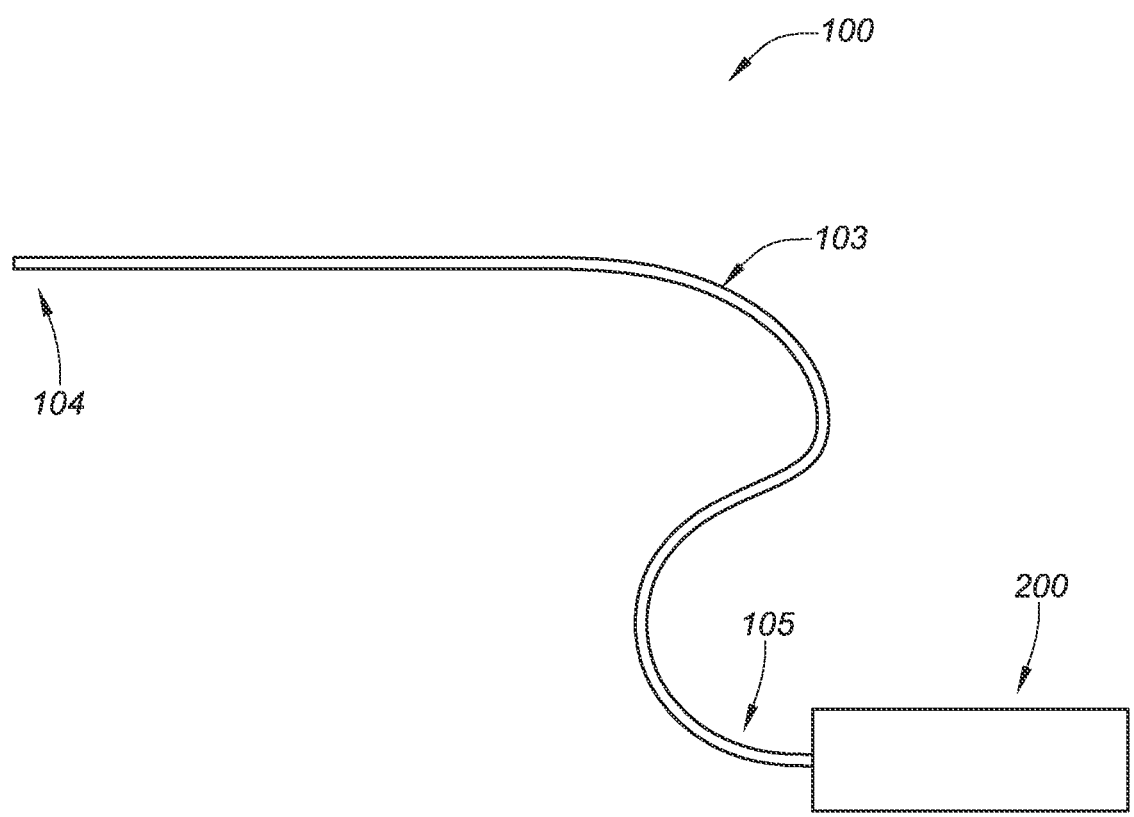
FIG. 1A is a block diagram depicting an example embodiment of a delivery system.

FIG. 1A is a block diagram depicting an example embodiment of delivery system 100 having an elongate delivery device 103 coupled with a proximal control device 200. A distal end region 104 is adapted to be inserted into the patient's urethra (or other lumen or body cavity of the patient) through the urethral orifice. Distal end region 104 preferably has an atraumatic configuration (e.g., relatively soft and rounded) to minimize irritation or trauma to the patient. Elongate delivery device 103 carries or houses one or more implants 102 (not shown) to be delivered or deployed within or adjacent to the prostatic urethra. A proximal end region 105 of delivery device 103 is coupled with proximal control device 200, which remains outside of the patient's body and is configured to be used by the physician or other healthcare professional to control the delivery of one or more implants 102.

Example Embodiments of Delivery Devices and Related Methods

Figure 1B:
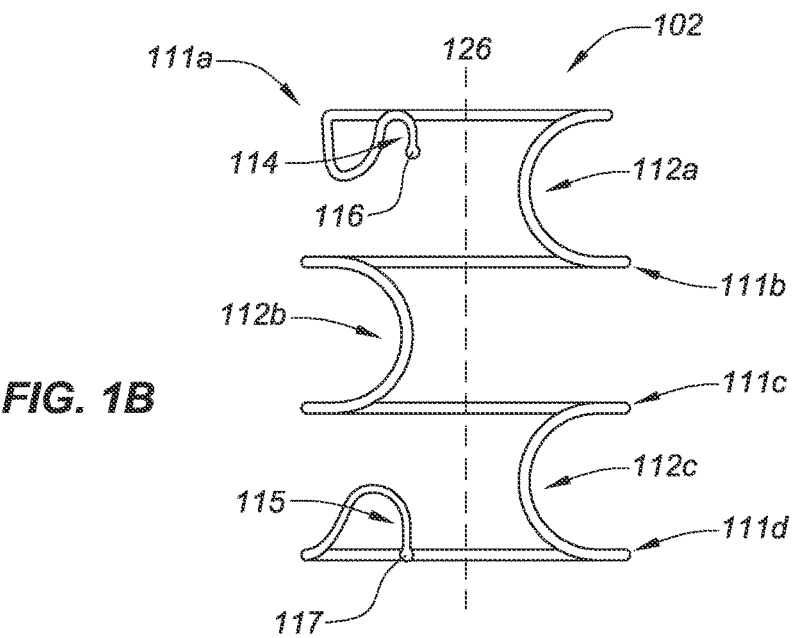
FIGS. 1B, 1C, and 1D are side, end, and perspective views, respectively, depicting an example embodiment of an implant.
Figure 1C:
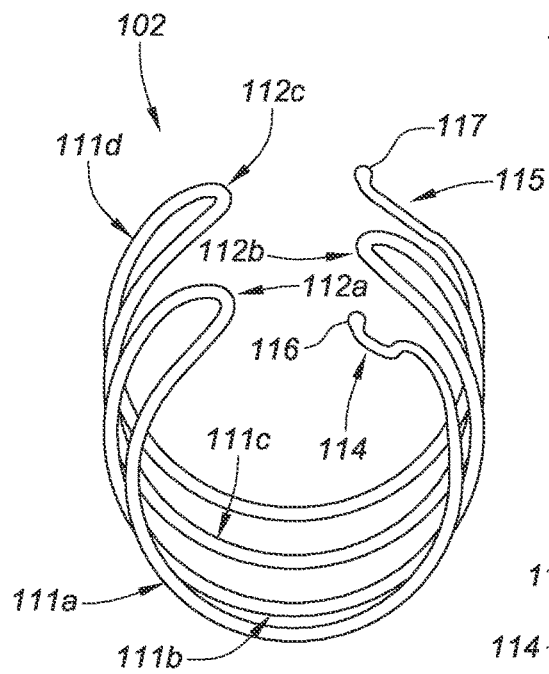
Figure 1D:
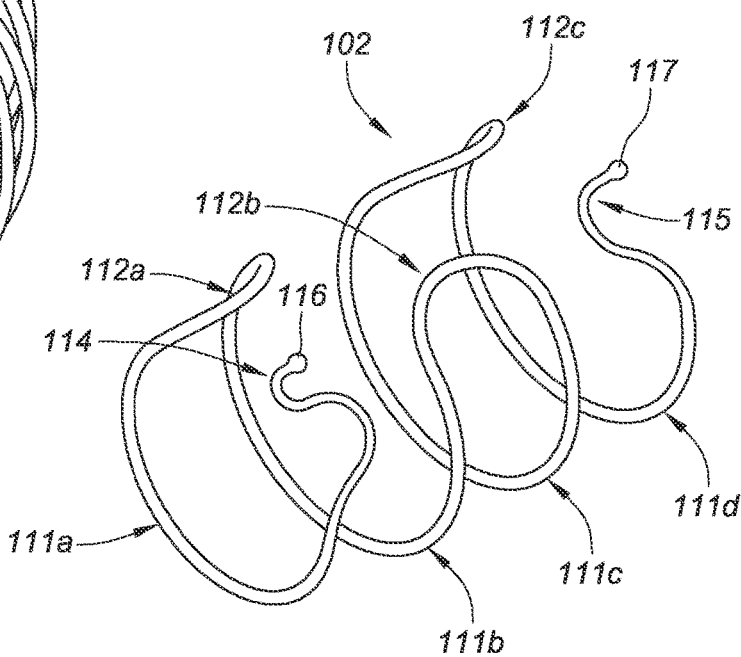

FIGS. 1B, 1C, and 1D are side, end, and perspective views, respectively, depicting an example embodiment of implant 102 in an at-rest configuration. Implantable device 102 is biased towards the at-rest configuration depicted here and is deformable between the at-rest configuration and a relatively more elongate housed (or delivery) configuration (e.g., see FIG. 3A) for housing implant 102 within delivery device 103. The housed configuration can be a straight or lineated state with minimal curvature. The at-rest configuration has a relatively greater lateral width, and a relatively shorter longitudinal length than the housed configuration. Upon exiting an open end of delivery device 103, implant 102 is free to transition its shape back towards that of the at-rest configuration although restraints imparted by the patient's urethral wall may prevent implant 102 from fully reaching the at-rest configuration. Because implant 102 is biased towards the at-rest configuration, implant 102 is configured to automatically expand when freed from the restraint of delivery device 103, and can be referred to as "self-expanding." The shape of implant 102 in its deployed state within, e.g., the patient's urethra, can be referred to as the deployed configuration, and will often be a shape that is deformed from the at-rest configuration by the surrounding tissue, although the deployed configuration can be the same as the at-rest configuration.

Implant 102 can be configured in numerous different ways, including any and all of those implant configurations described in U.S. Patent Publ. No. 2015/0257908 and/or Int'l Publ. No. WO 2017/184887, both of which are incorporated by reference herein for all purposes.

Implant 102 can be formed from one or more discrete bodies (e.g., wires, ribbons, tubular members) of varying geometries. Referring to the embodiment of FIGS. 1B-1D, implant 102 has a main body formed of only one single wire member set in a predetermined shape. Implant 102 can have two or more ring-shaped structures 111 (in this embodiment there are four: 111a, 111b, 111c, and 111d) with one or more interconnections 112 extending between each pair of adjacent ring-shaped structures 111 (in this embodiment there is one interconnection between each adjacent pair, for a total of three: 112a, 112b, and 112c). Each interconnection 112 extends from one ring-shaped structure 111 to an immediately adjacent ring-shaped structure 111. Each interconnection 112 can have a relatively straight shape (not shown) or a curved (e.g., semi-circular or semi-elliptical) shape as shown in FIGS. 1B-1D.

Ring-shaped structures 111 are configured to maintain the urethra in a fully or partially open state when expanded from the housed configuration. Device 100 can be manufactured in various sizes as desired, such that the width (e.g., diameter) of each ring-shaped structure 111 is slightly larger than the width of the urethra, and the length of each interconnection 112 determines the spacing between ring-shaped structures 111. Ring-shaped structures 111 can have the same or different widths. For example, in the embodiment depicted here, ring-shaped structure 111a has a relatively smaller width than structures 111b-111d, which have the same width. This can accommodate prostatic urethras that converge to a smaller geometry before the bladder neck.

Each ring-shaped structure 111 can be located or lie in a single plane, and in some embodiments that single plane can be oriented with a normal axis perpendicular to a central axis 124 of implant 102 (as depicted in FIG. 1B). In other embodiments, ring-shaped structures 111 can be located in multiple planes. Ring-shaped structures 111 can extend around central axis 126 to form a complete circle (e.g., a 360 degree revolution) or can form less than a complete circle (e.g., less than 360 degrees) as shown here. Although not limited to such, in many embodiments ring-shaped structures 111 extend between 270 and 360 degrees.

As can be seen from FIGS. 1B-1D, the geometry of implant 102 can have a cylindrical or substantially cylindrical outline shape with a circular or elliptical cross-section. In other embodiments, implant 102 can have a prismatic or substantially prismatic shape with triangular or substantially triangular cross-section, or otherwise.

Implant 102 can also include a distal engagement member 114 and a proximal engagement member 115 that are each configured to engage with elements of delivery device 103. Engagement with delivery device 103 can serve one or more purposes such as allowing control of the release of implant 102, allowing movement of the ends of implant 102 relative to each other, and/or allowing retrieval of implant 102 after deployment, e.g., in an instance where the physician desires to recapture implant 102 and redeploy implant 102 in a different position. In this embodiment, distal engagement member 114 is a wire-like extension from ring-shaped structure 111a that has a curved (e.g., S-like) shape for positioning an atraumatic end 116 (e.g., rounded, spherical, ballized) in a location suitable for engagement with delivery device 103 and thereby allow control of the distal end region of implant 102. Likewise, proximal engagement member 115 has a curved shape for positioning another atraumatic end 117 in a location suitable for engagement with delivery device 103 and thereby allow control of the proximal end region of implant 102. In other embodiments, distal engagement member 114 and proximal engagement member 115 can be configured such that the atraumatic ends 116 and 117 point in different directions. For example, atraumatic ends 116 and 117 can be pointing distally instead of proximally. In another embodiment, atraumatic ends 116 and 117 can be pointing in opposite directions (e.g., atraumatic end 116 can be pointing distally and atraumatic end 117 can be pointing proximally, and vice versa). In other embodiments, distal engagement member 114 and proximal engagement member 115 can be omitted, and delivery device 103 can couple with implant 102 at one or more other distal and/or proximal locations, such as on a ring-shaped structure 111 or interconnect 112. Moreover, an extension having an atraumatic end (similar to distal engagement member 114 and proximal engagement member 115) can be attached in the middle of implant 102 in order to provide an additional structure to control placement of the middle portion of the implant.

Figure 2A:
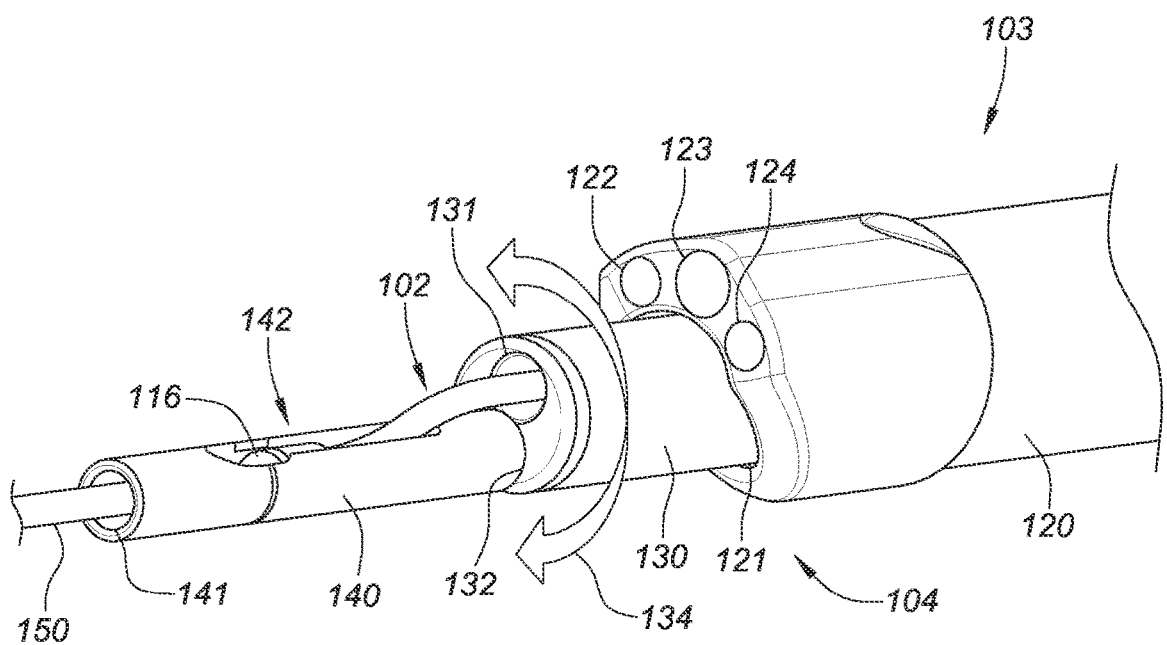
FIGS. 2A-2B are perspective views depicting example embodiments of a delivery system in different stages of deployment of an implant.

Delivery device 103 can include one or more elongate flexible members (e.g., 120, 130, 140, and 150 as described below), each having one or more inner lumens. Alternatively, one or more elongate flexible members of delivery device 103 can be a solid or a non-hollow member with no inner lumen. FIG. 2A is a perspective view depicting an example embodiment of distal end region 104 of a delivery device 103. In this embodiment, delivery device 103 includes a first elongate tubular member 120, a second elongate tubular member 130, a third elongate tubular member 140, and a fourth elongate tubular member 150. Delivery device 103 can vary and in other embodiments can include more or less tubular members.

In this embodiment, first elongate tubular member 120 is the outermost tubular member and is flexible yet provides support for members contained therein. First tubular member 120 is referred to herein as outer shaft 120 and can have one or more inner lumens. In this embodiment, outer shaft 120 includes a first inner lumen 121 housing second elongate tubular member 130, which is referred to herein as inner shaft 130. Outer shaft 120 and inner shaft 130 are each controllable independent of the other. Inner shaft 130 can slide distally and proximally within lumen 121 and is shown here partially extending from an open distal terminus of outer shaft 120.

In this embodiment, outer shaft 120 includes three additional lumens 122, 123, and 124. An illumination device (not shown) and an imaging device (not shown) can be housed in two of lumens 122-124 (e.g., lumens 122 and 123). The imaging device can utilize any desired type of imaging modality, such as optical or ultrasound imaging. In one example embodiment the imaging device utilizes a forward (distal) looking CMOS imager. The illumination device can be configured to provide adequate illumination for optical imaging, and in one embodiment includes one or more light emitting diodes (LEDs). In embodiments where illumination is not required, such as for ultrasound imaging, the illumination device and its respective lumen can be omitted or the lumen could be used for an alternative purpose, e.g., as an irrigation or flushing channel. The illumination device and/or the imaging device can each be fixedly secured at the distal terminuses of lumens 122 and 123, or each can be slidable within lumens 122 and 123 to allow advancement further distally from outer shaft 120 and/or retraction into outer shaft 120. In one example embodiment, the illumination device and the imaging device are mounted together and only a single lumen 122 or 123 is present for that purpose. The remaining lumen (e.g., lumen 124) can be configured as an irrigation or flush port from which fluid such as saline can be introduced to the urethra to flush the region and provide adequate fluid through which implant 102 and the surrounding prostatic urethra wall can be imaged. In one embodiment, the outer shaft may contain two separate lumens for fluid management. One lumen may be used for irrigation and the other lumen may be used for flushing.

Outer shaft 120 has a proximal end (not shown) coupled with proximal control device 200. Delivery device 103 can be configured to be steerable to navigate tortuous anatomy. Steerability can be unidirectional (e.g., using a single pull wire) or multidirectional (e.g., using two or more pull wires arranged at different radial locations about device 103) depending on the needs of the application. In some embodiments, the structures (e.g., pull wires) for steerability extend from distal end region 104 of delivery device 103 (e.g., where the distal ends of the pull wires are secured to a plate or other structure within distal end region 104) to proximal control device 200, where they can be manipulated by the user to steer delivery device 103. The steering structures can be located in one or more lumens of outer shaft 120, or can be coupled to or embedded within a sidewall of outer shaft 120. Delivery device 103 can be biased to deflect in a particular lateral direction (e.g., bend) such that device 103 automatically deflects in that manner and forces imparted to steer delivery device 103 are in opposition to this biased deflection. Other mechanisms for steering delivery device 103 can also be used. The steering mechanism may also be locked or adjusted during deployment of implant 102 to control the position of implant 102 within the anatomy (e.g., steering anteriorly during deployment may help place implant 102 in a more desirable anterior position).

Inner shaft 130 can include one or more inner lumens for housing one or more implants 102 and/or other components. In this embodiment, inner shaft 130 includes a first lumen 131 in which one or more implants 102 can be housed, and a second lumen 132 in which third elongate tubular member 140 can be housed. In this embodiment, third elongate tubular member 140 is configured to releasably couple with the distal end region of implant 102 and is referred to as a distal control member or tether 140. Distal control member 140 can be slidably advanced and/or retracted with respect to inner shaft 130. Distal control member 140 can include an inner lumen 141 that houses fourth elongate tubular member 150, which is shown here extending from an open distal terminus of distal control member 140. Fourth elongate tubular member 150 is configured to anchor delivery device 103 with respect to the patient's anatomy, e.g., to keep components of delivery device 103 stationary with respect to the anatomy during deployment of implant 102, and is referred to as anchor delivery member 150.

In the configuration depicted in FIG. 2A, anchor delivery member 150 is extended from lumen 141 of distal control member 140, and distal control member 140 along with inner shaft 130 are shown extended from lumen 121 of outer shaft 120. When delivery device 130 is advanced through the urethra, anchor delivery member 150 is preferably housed entirely within distal control member 140, and distal control member 140 along with inner shaft 130 are retracted from the positions shown in FIG. 2A such that they reside within lumen 121 of outer shaft 120 and do not extend from the open distal terminus of lumen 120. In other words, in some embodiments the open distal terminus of outer shaft 120 forms the distalmost structure of device 103 upon initial advancement through the urethra. This facilitates steering of delivery device 103 by outer shaft 120. The physician can advance distal end region 104 of delivery device 103 to be in proximity with the desired implantation site, or entirely into the patient's bladder. Anchor delivery member 150 can be exposed from the open distal terminus of distal control member 140, either by distally advancing anchor delivery member 150 further into the bladder, or if already present within the bladder, then by proximally retracting the other components of delivery device 103. At this point the anchor from anchor delivery member 150 can be deployed in the bladder.

Figure 2B:
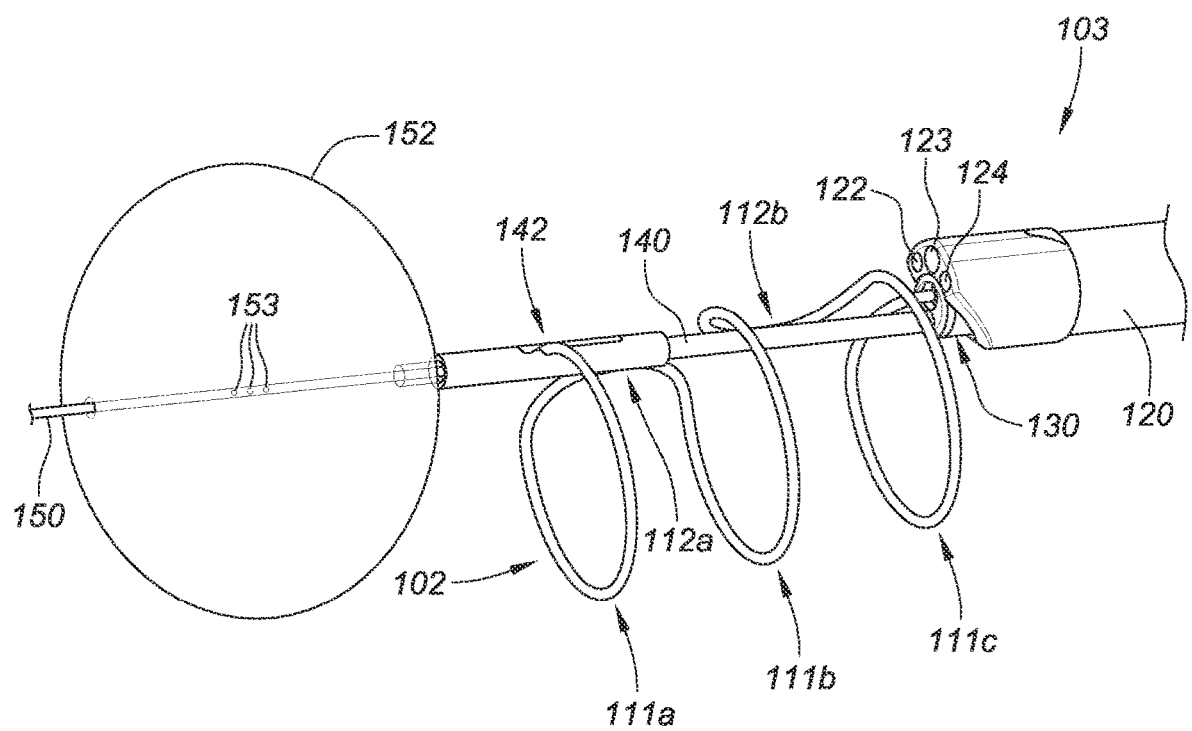

FIG. 2B is a perspective view depicting distal end region 104 of delivery device 103 with the various components deployed. In this embodiment, anchor delivery member 150 includes an anchor 152 in the form of an inflatable member or balloon.

Other embodiments of anchors 152 are described in International Application No. PCT/US19/32637, filed May 16, 2019, which is hereby incorporated by reference in its entirety for all purposes. Anchor 152 expands (or otherwise transitions) to a size greater than that of the bladder neck such that anchor 152 resists proximal retraction (e.g., a relatively light tension). In embodiments where anchor 152 is a balloon, that balloon can be an elastic or inelastic and inflatable with an inflation medium (e.g., air or liquid such as saline) introduced into balloon 152 through one or more inflation ports 153. Here three inflation ports 153 are located on the shaft of anchor delivery member 150 and communicate with an inflation lumen that extends proximally back to proximal control device 200, which can include a port for inflation with a syringe. Upon deployment of anchor 152, the physician can proximally retract delivery system 100 until anchor 152 is in contact with the bladder neck and/or wall (if not already).

The physician can use the imaging device of outer shaft 120 to move delivery device 103 proximally away from anchor 152 until the physician is in the desired position within the urethra to begin deployment of implant 102. A retainer 142 on distal control member 140 is releasably coupled with distal engagement member 114 of implant 102. The physician can position retainer 142 in a location along the length of the urethra where the physician desires the distal end of implant 102 to deploy. This can involve moving distal control member 140 and inner shaft 130, together, proximally and/or distally with respect to anchor delivery member 150. In another embodiment, the position of retainer 142 is fixed with respect to anchor 152 such that the longitudinal position of implant 102 within the anatomy is set by the system independently of any manipulation by the physician. The coupling of distal engagement member 114 with retainer 142 also permits the physician to manipulate the radial orientation of implant 102 by rotating distal control member 140 and inner shaft 130 together. Active or passive shaping of distal control member 140 may allow for a more desirable placement of implant 102. For example, member 140 may have a curvature that places the implant in a more anterior anatomical position. This curvature may be inherently set in member 150 or actively applied by the physician though a separate entity such as a control wire. Once in the desired location and orientation, the physician can proximally retract inner shaft 130 with respect to distal control member 140 to initiate deployment of implant 102.

Distal engagement member 114 is held in place with respect to distal control member 140 by retainer 142, and proximal retraction of inner shaft 130 with respect to distal control member 140 causes ring-shaped structures 111 to begin to deploy in sequence (111a, then 111b, then 111c, then 111d (not shown)). Distal control member 140 can remain stationary or be moved longitudinally with respect to the urethra during deployment. In some embodiments, distal control member 140 is steerable to allow for angulation of implant 102 to accommodate relatively tortuous anatomy. The steerability of distal control member 140 can also accomplish relatively anterior placement of the implant relative to the bladder neck, which potentially contributes to improved flow results. For example, see distal control member 140 as shown in FIGS. 2C-2G and FIGS. 10C and 10D. Mechanisms for accomplishing steerability are discussed elsewhere herein and can likewise be applied to distal control member 140. In these or other embodiments, distal control member 140 can be significantly flexible to passively accommodate tortuous anatomy. In some embodiments, distal control member 140 has a predefined curve to assist in navigation.

To assist in deployment, inner shaft 130 can rotate clockwise and counterclockwise (as depicted by arrow 134) about distal control member 140. Referring back to FIGS. 1B-1C, implant 102 has a non-constant direction of winding that, when viewed as commencing at distal engagement member 114, proceeds clockwise along ring-shaped structure 111a, then reverses along interconnect 112a to a counterclockwise direction for ring-shaped structure 111b, then reverses along interconnect 112b to a clockwise direction for ring-shaped structure 111c, and then reverses along interconnect 112c to a counterclockwise direction for ring-shaped structure 111d, until ending at proximal engagement member 115. Depending on the direction of winding of the portion of implant 102 about to exit the open distal terminus of lumen 131, the transition of implant 102 towards the at-rest configuration can impart a torque on shaft 130 if shaft 130 is not actively rotated as implant 102 is deployed. That torque can cause shaft 130 to passively rotate (without user intervention) either clockwise or counterclockwise accordingly. In certain embodiments described elsewhere herein, shaft 130 is actively rotated during deployment. Rotation of inner shaft 130 with respect to distal control member 140 thus allows delivery device 103 to rotate and follow the direction of winding of implant 102. In some embodiments, all ring-shaped structures 111 are wound in the same direction, clockwise or counterclockwise (e.g., as in the case of a fully spiral or helical implant), or do not have a set direction of winding.

In this or other embodiments, the distal end region of inner shaft 130 is configured to be relatively more flexible than the more proximal portion of inner shaft 130, which can permit avoidance of excessive motion of the rest of device 103 during deployment, resulting in better visualization and less tissue contact by device 103. Such a configuration can also reduce the stress imparted on implant 102 by device 103 during delivery. For example, the portion of inner shaft 130 extending from outer shaft 120 during deployment can be relatively more flexible than the portion of inner shaft 130 that remains within outer shaft 120, thus allowing inner shaft 130 to flex more readily as implant 102 exits inner lumen 131. This in turn can stabilize delivery device 103 and allow the physician to obtain stable images of the appointment process.

Figure 4A:
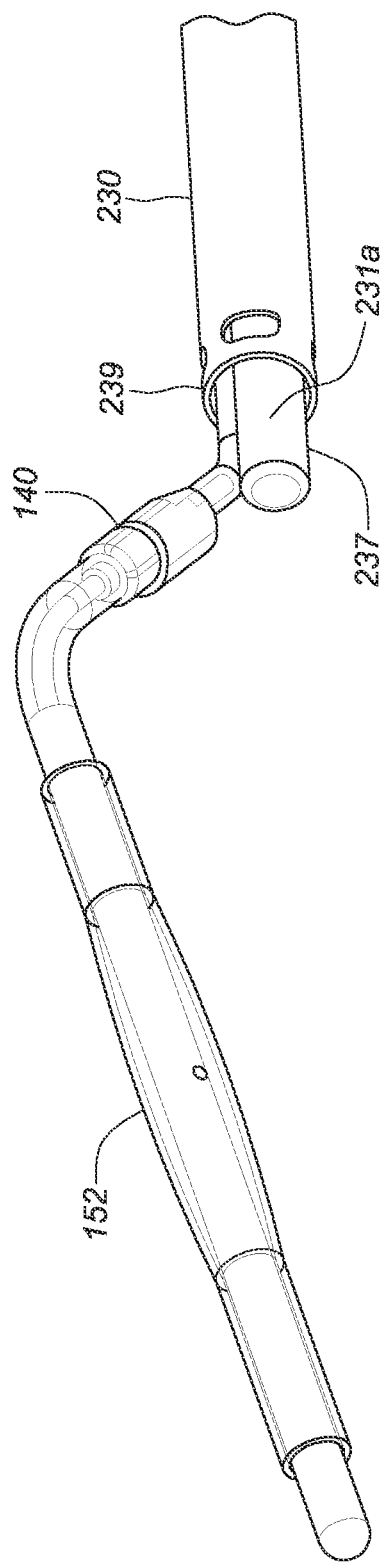
FIGS. 4A-4C are perspective views depicting an example embodiment of an inner shaft.
Figure 4B:
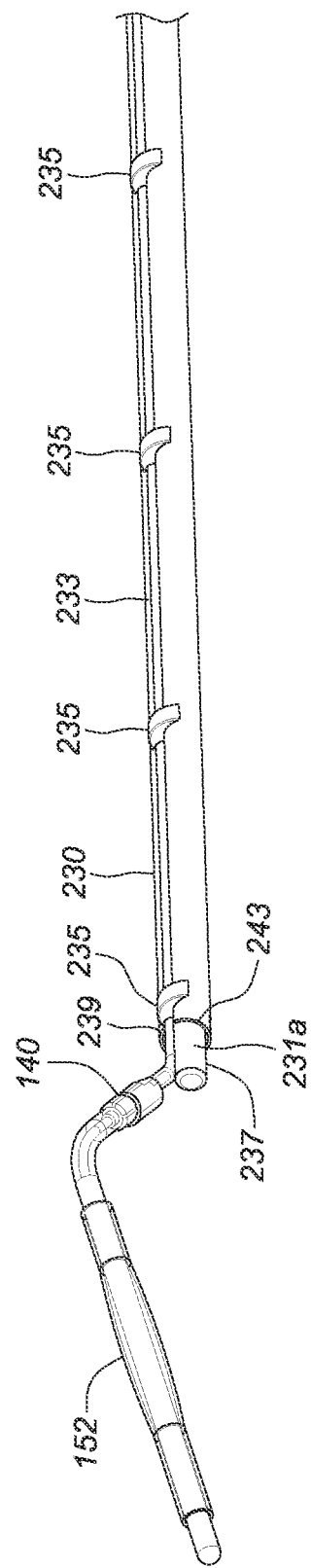
Figure 4C:
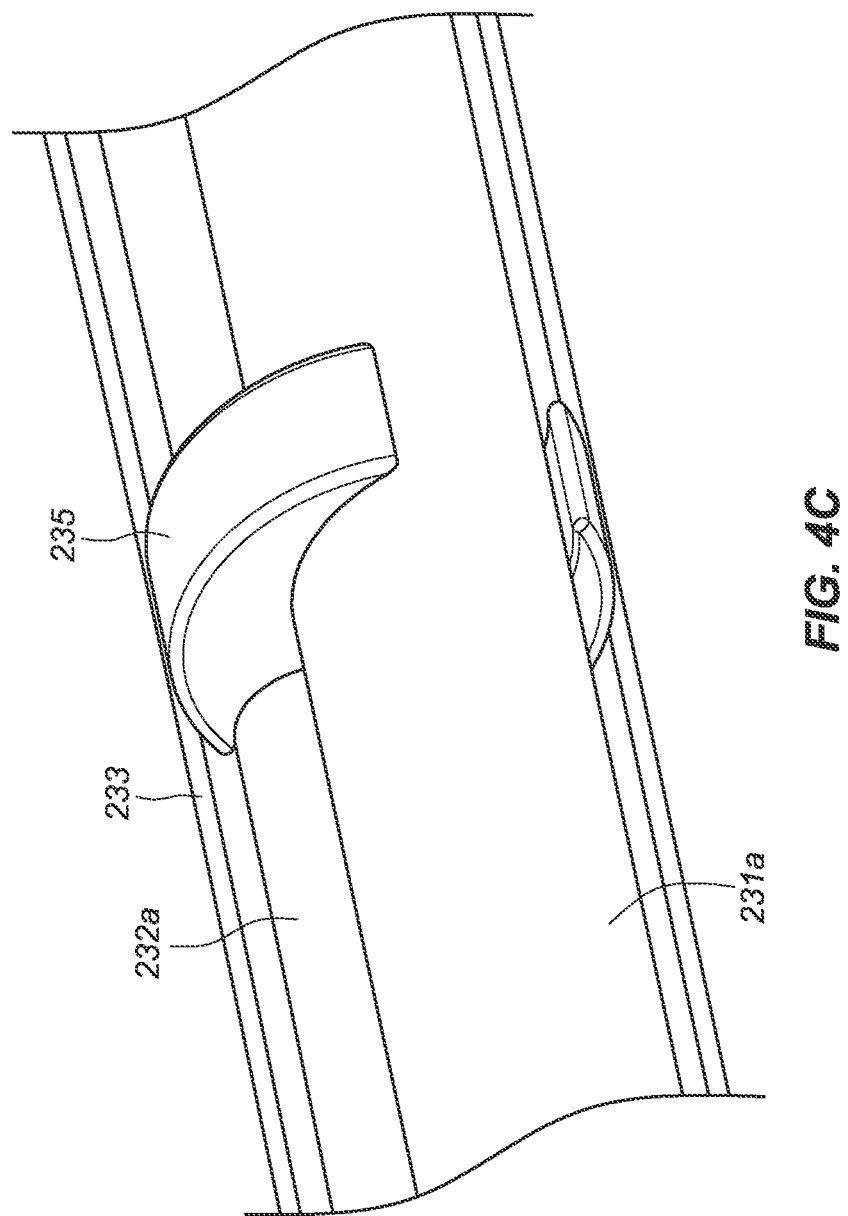
Figure 4D:
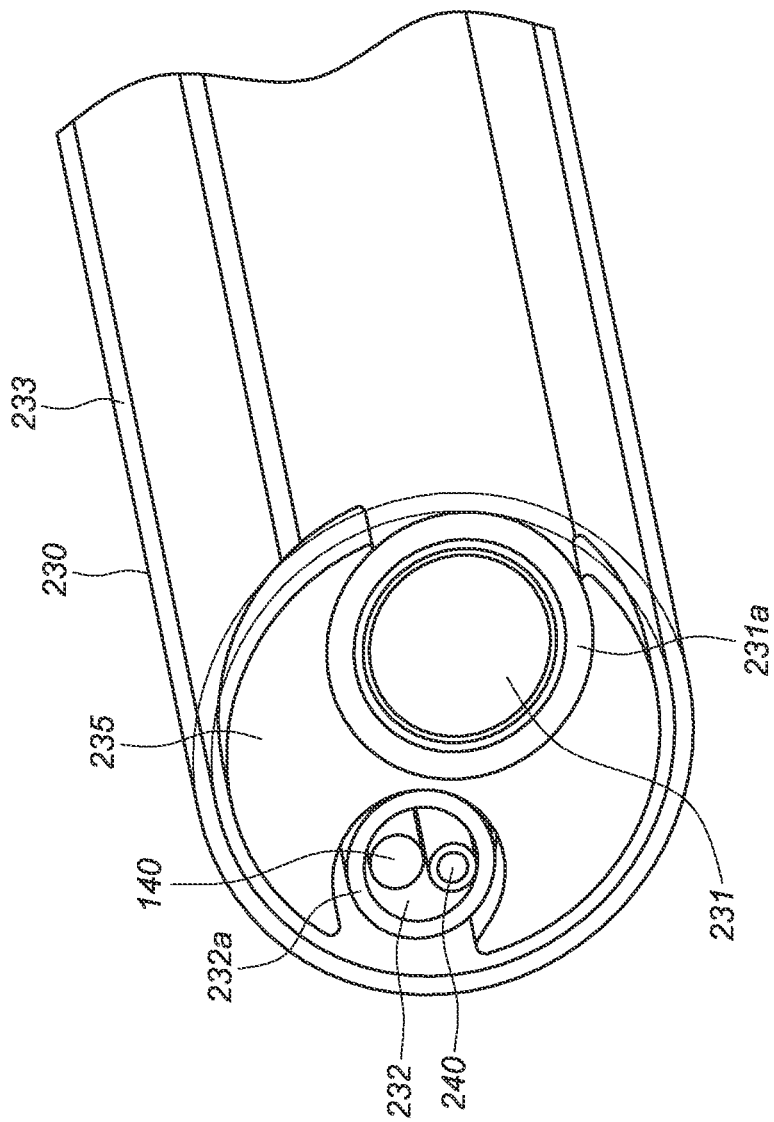
FIGS. 4D-4E are cross-sectional views depicting an example embodiment of an inner shaft.
Figure 4E:
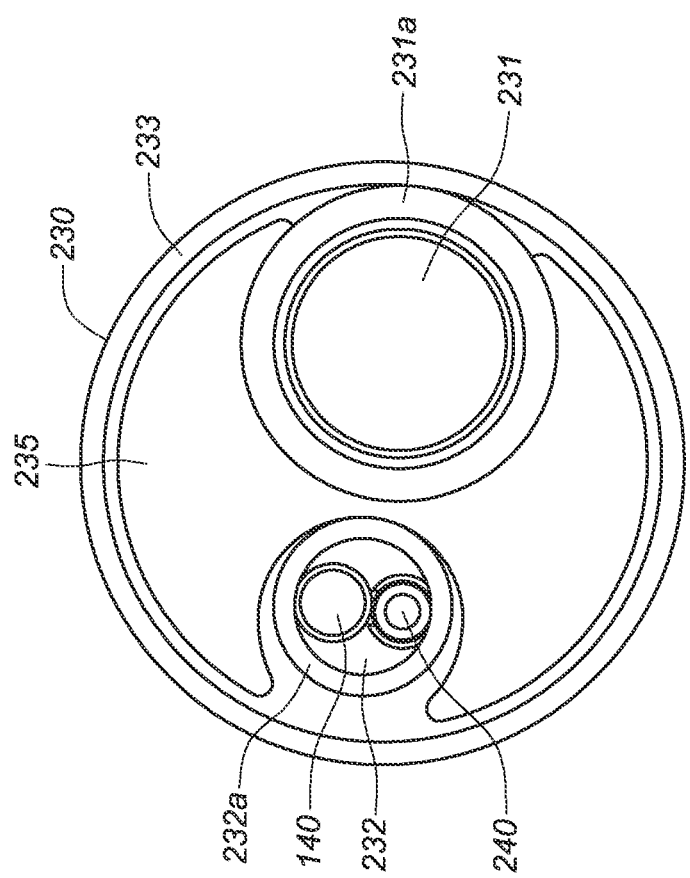

In an alternative embodiment, as seen in FIGS. 4A-4E, inner shaft 230 can include an outer torqueing tube 233 (FIGS. 4B-4E), one or more lumens for housing one or more implants 102 and/or other components, and one or more torqueing supports 235. In this embodiment, inner shaft 230 includes a first elongate tubular member 231a having a first lumen 231 in which one or more implants 102 can be housed. First elongate tubular member 231a also has a second elongate tubular member 232a (or tether) having a second lumen 232 in which a third elongate tubular member 140 and a fourth elongate tubular member 240, which could act as an inflation lumen, can be housed. In an alternative embodiment, the second elongate tubular member 232a (or tether) can be used for release/actuation and the inflation lumen can be concentric with the tether. As seen in FIGS. 4D and 4E, the first 231a and second 232a elongate tubular members can sit side-by-side and be held in place by the torqueing supports 235. The torqueing supports 235 can be small plates spaced within the outer torqueing tube 233 from a proximal to a distal end of outer torqueing tube 233. For example, the torqueing supports 235 may be placed about 3 to about 6 inches apart, alternatively about 2 to about 5 inches apart, alternatively about 1 to about 4 inches apart. The torqueing supports 235 can be bonded or otherwise fixed in place relative to the outer torqueing tube 233 to ensure that axial and angular position of the outer torqueing tube 233 can be maintained by the user. The first elongate tubular member 231a can be fixed to the torqueing supports 235 to ensure that the first elongate tubular member 231a moves with the outer torqueing tube 233. The second elongate tubular member 232a may not be fixed to the torqueing supports 235 so that the second elongate tubular member 232a can move axially and rotationally relative to the support plate and outer torqueing tube 233.

As seen in FIG. 4B, the flexible tip 243 may be created by fixing the first elongate tubular member or implant delivery tube 231a such that its distal end 237 extends beyond the distal tip 239 of the outer torqueing tube 233 by between about 0 cm and 1.5 cm, alternatively between about 0 cm and 1.0 cm, and alternatively between about 0.2 and 1.0 cm.

The components of the inner shaft may be made from appropriate materials. The first elongate tubular member or implant delivery tube 231a may be a braided tubular assembly with a lubricious liner. It may be made from a laser cut hypotube with a lubricious liner, a single polymer extrusion, or other appropriate material. The outer torqueing tube 233 may be made from a laser cut hypotube, a braided construction, a polymer extrusion, or other appropriate material. The torqueing supports 235 may be laser-cut metal plates, molded plastic components, extruded materials, or other appropriate material.

FIG. 2B depicts implant 102 after three ring-shaped structures 111a, 111b, and 111c have been deployed. Proximal retraction of shaft 130 continues until the entirety of implant 102, or at least all of ring-shaped structures 111, have exited lumen 131. If the physician is satisfied with the deployed position of implant 102 and the deployed shape of implant 102, then implant 102 can be released from delivery device 103. A control wire 146 (not shown in FIG. 2B) extends within the length of control member 140, either in the same lumen as anchor delivery member 150 or in a different lumen, and is coupled to retainer 142. Control wire 146 can be routed into member 140 through an opening 148.

Release of the distal end of implant 102 can be accomplished by releasing retainer 142. Retainer 142 can be a cylindrical structure or other sleeve that linearly or rotationally actuates over a cavity or recess in which a portion of implant 102 is housed. In the embodiment of FIG. 2B, retainer 142 includes an opening or slot that allows distal engagement member 114 to pass therethrough. Retainer 142 can rotate with respect to the cavity or recess in which distal engagement member 114 (not shown) is housed until the opening or slot is positioned over member 114, at which point member 114 is free to release from distal control member 130. Rotation of retainer 142 can be accomplished by rotation of a rotatable shaft, rod or other member coupled with retainer 142 (and accessible at proximal control device 200). Alternative embodiments of retainers can be found in FIGS. 2C-2F of International Application No. PCT/US19/32637, filed May 16, 2019, which was previously incorporated by reference in its entirety for all purposes.

Figure 2C:
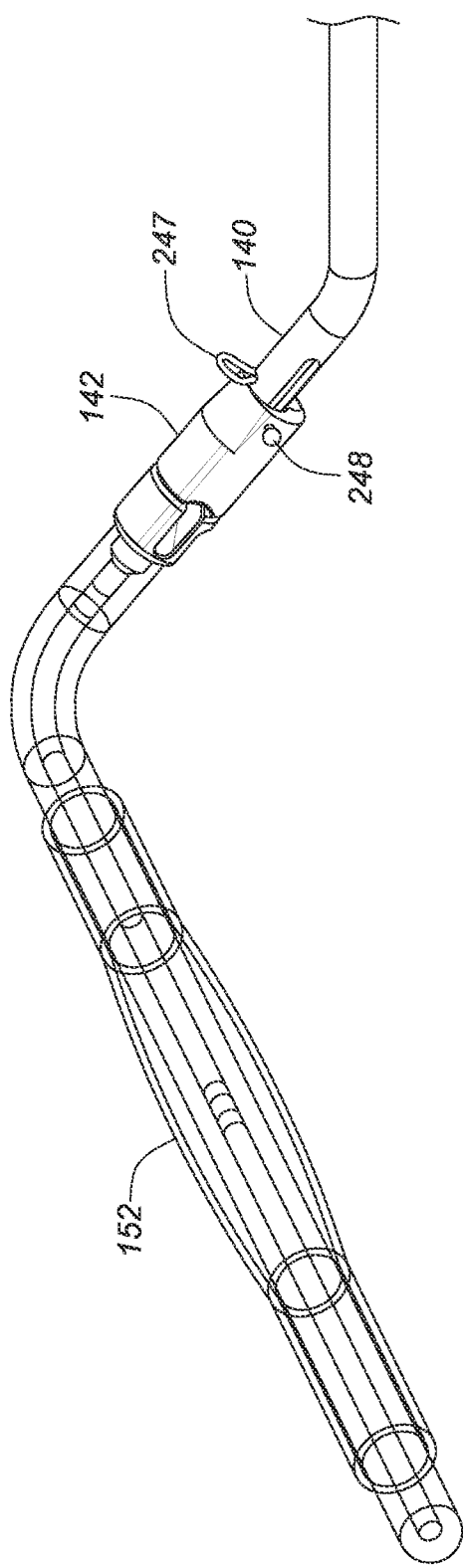
FIGS. 2C-2G are perspective views depicting an example of a release mechanism.
Figure 2D:
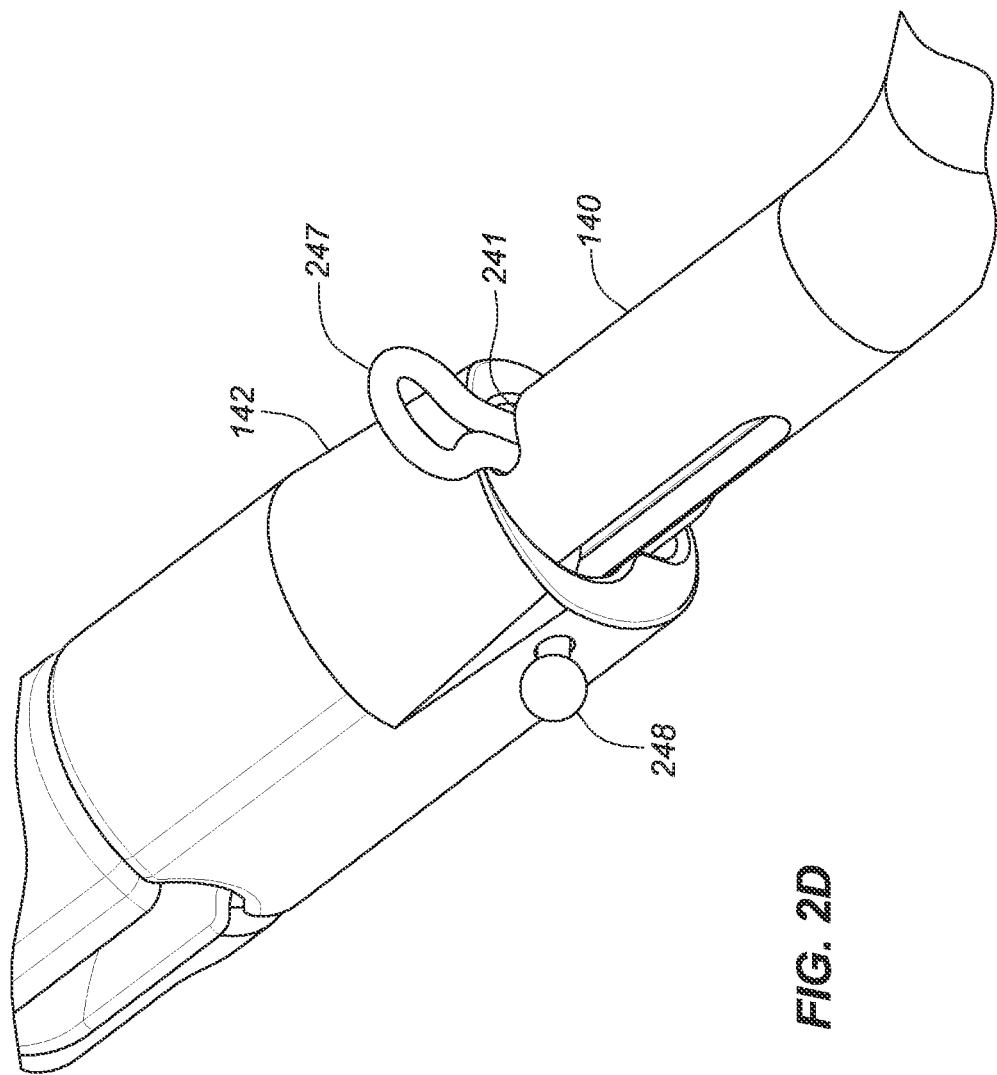
Figure 2E:
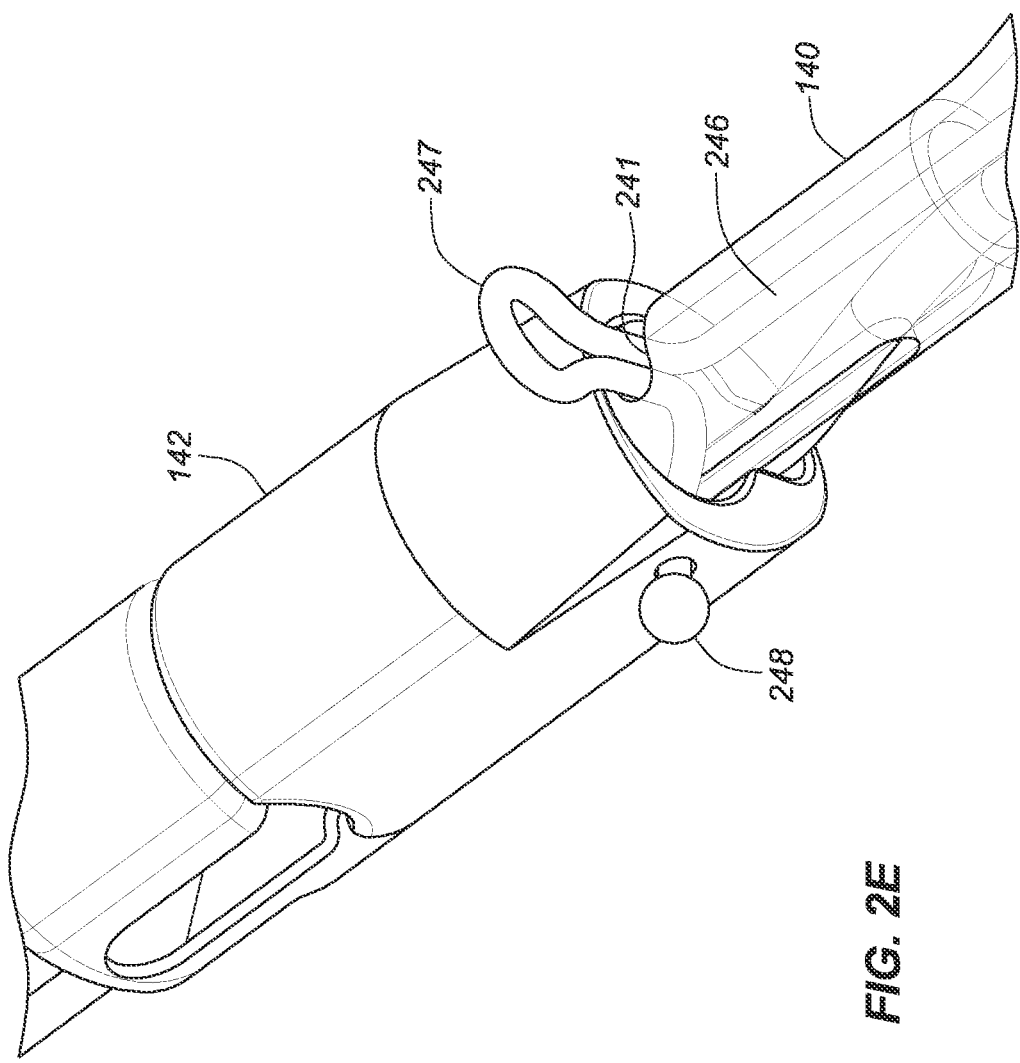

FIGS. 2C-2G are perspective views depicting another example embodiment of system 100 with an alternative retainer 142 that can be fixed in position with a tether lock. As in other embodiments, retainer 142 slides distally and/or proximally with respect to distal control member 140. Distal engagement member 114 of implant 102 can be received within a corresponding recess 143 (FIG. 2G) of distal control member 140. Retainer 142 can slide over distal engagement member 114 while received within this recess 143 until retainer 142 abuts a portion of member 140, which has opening 241 located near its distal end. A control wire 246 extends within the length of control member 140, either in the same lumen as anchor delivery member 150 or in a different lumen, and attaches or couples to retainer 142 at its distal end 248. As seen in FIG. 2E, control wire 246 passes out of and back into opening 241 in distal control member 140, such that control member 246 forms a loop 247 that protrudes from the opening and extends along an axis perpendicular to a longitudinal axis of the distal control member and a longitudinal axis of retainer 142. Loop 247, which is located adjacent to and proximal of retainer 142, prevents retainer 142 from moving in a proximal direction over distal control member 140.

Figure 2F:
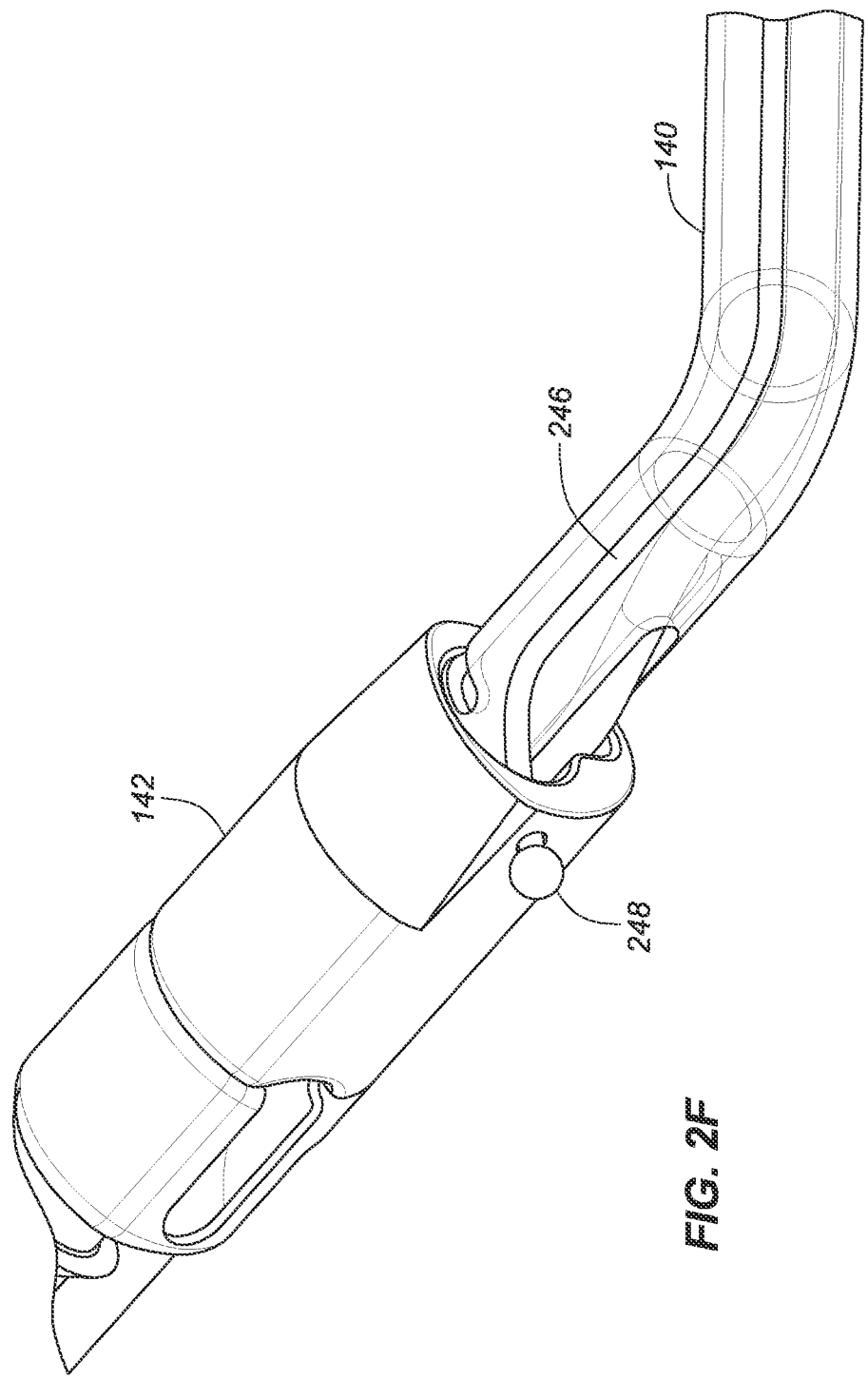
Figure 2G:
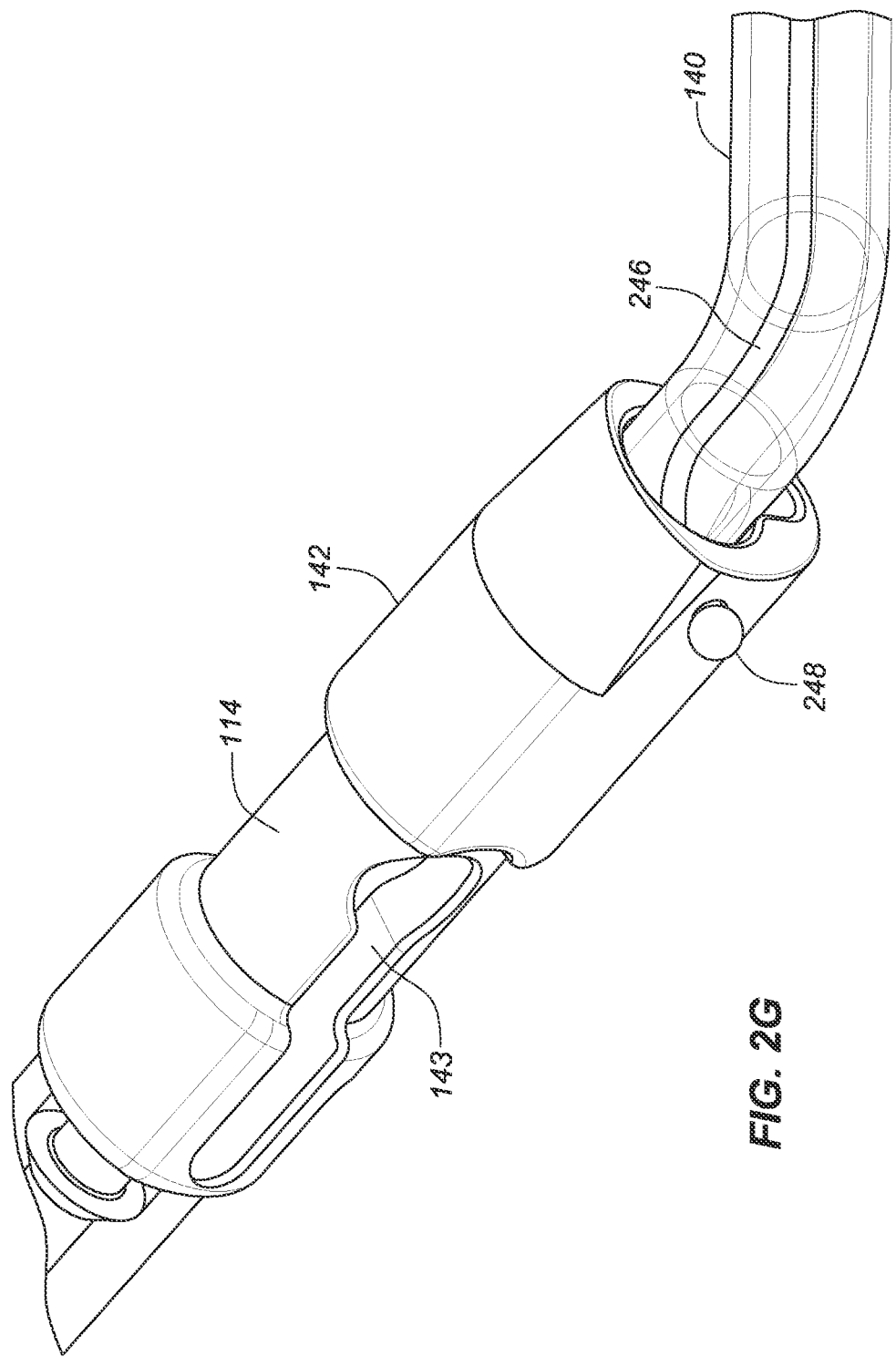

Upon satisfactory deployment of implant 102 within the urethra, e.g., in the state of FIG. 2C, control wire 246 can be tensioned by pulling control wire 246 in a proximal direction (away from the implant 102). As seen in FIG. 2F, the tension pulls loop 247 into the lumen of distal control member 140, thereby removing the obstruction preventing retainer 142 from sliding proximally. After the loop is withdrawn into the lumen of distal control member 140, as seen in FIG. 2G, retainer 140 is proximally retracted by further pulling control wire 246 proximally to expose engagement member 114 and permit its release from member 140.

Control member 146, 246 may be made from nitinol, Kevlar, stainless steel, suture, liquid crystal polymers (LCP) or any other tensionable material.

Figure 2H:
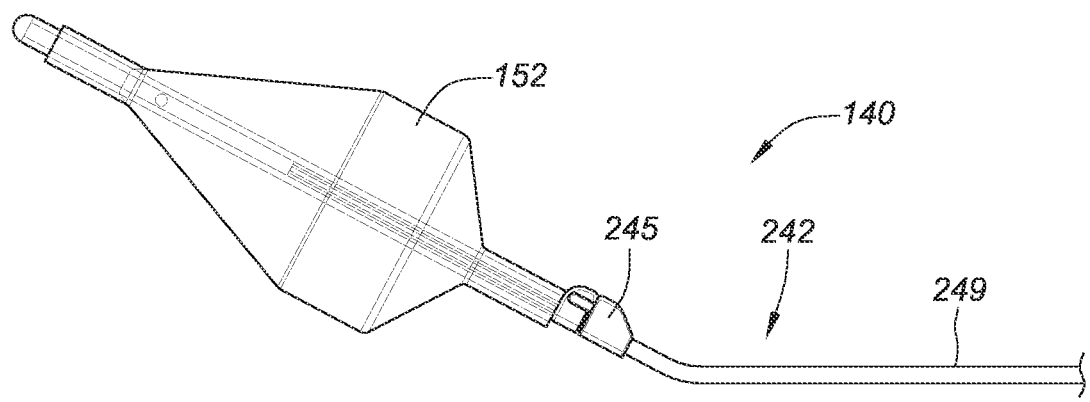
FIGS. 2H-2J are views depicting an alternative example of a release mechanism.
Figure 2I:
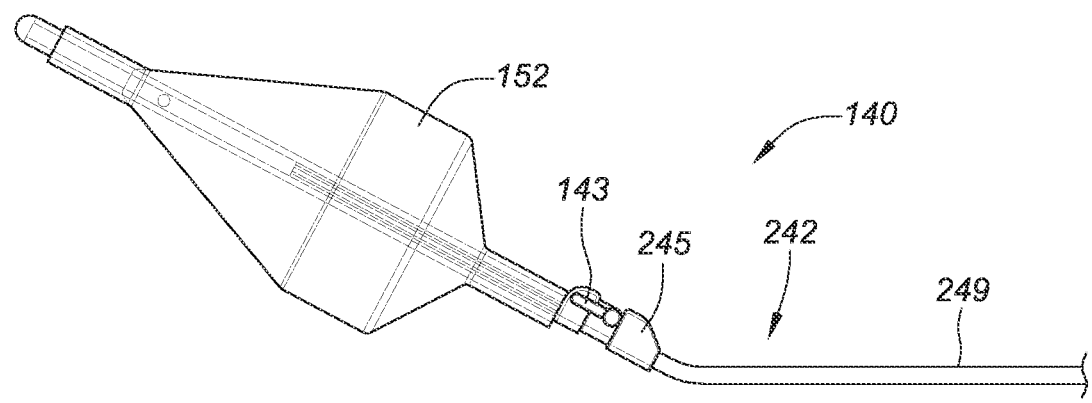
Figure 2J:
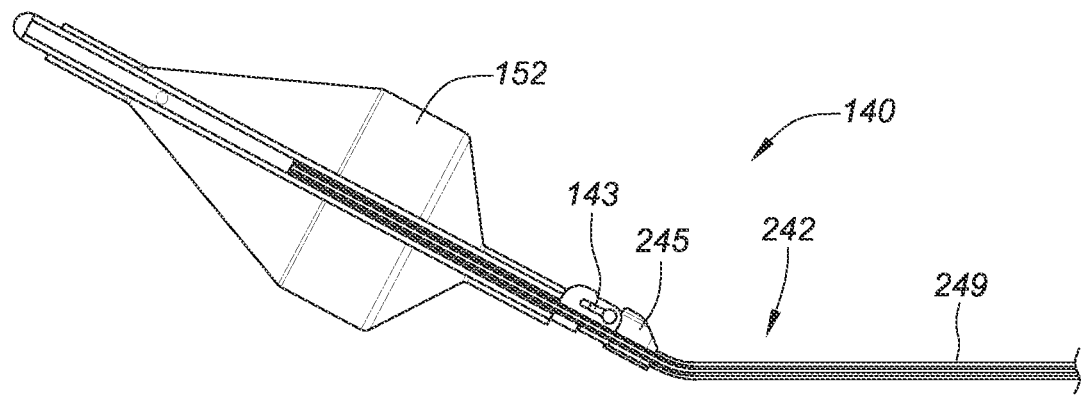

FIGS. 2H-2J illustrate another example embodiment of system 100 with an alternative retainer 242 that can be fixed in position. As with other embodiments described, retainer 242 can be a cylindrical structure or other sleeve that linearly or rotationally actuates over a cavity or recess in which a portion of implant 102 is housed. Retainer 242 includes cover 245 that is coupled to an outer tube 249 that extends to the control device 200. In the embodiment of FIGS. 2H-2J, retainer 242 includes an opening or slot (not shown) that allows distal engagement member 114 to pass therethrough. FIG. 2H shows cover 245 closed over the recess 143 that is adapted to hold distal engagement member 114. Retainer 242 can be withdrawn proximally with respect to the cavity or recess in which distal engagement member 114 is housed until the opening or slot is positioned over member 114, at which point member 114 is free to release from distal control member 130. As seen in FIG. 2I, cover 245 has been withdrawn by actuating outer tube 249 proximally. Withdrawal of cover 245 of retainer 242 can be accomplished by withdrawing outer tube 249 proximally, which is accessible at proximal control device 200. FIG. 2J is a cross-section showing the retainer 242 and the inflation lumen that communicates with anchor 152. The inflated diameter of the anchor balloon can be between about 1 cm and 7 cm, alternatively between about 2 cm and 6 cm, alternatively between about 1 cm and 6 cm.

Figure 3A:
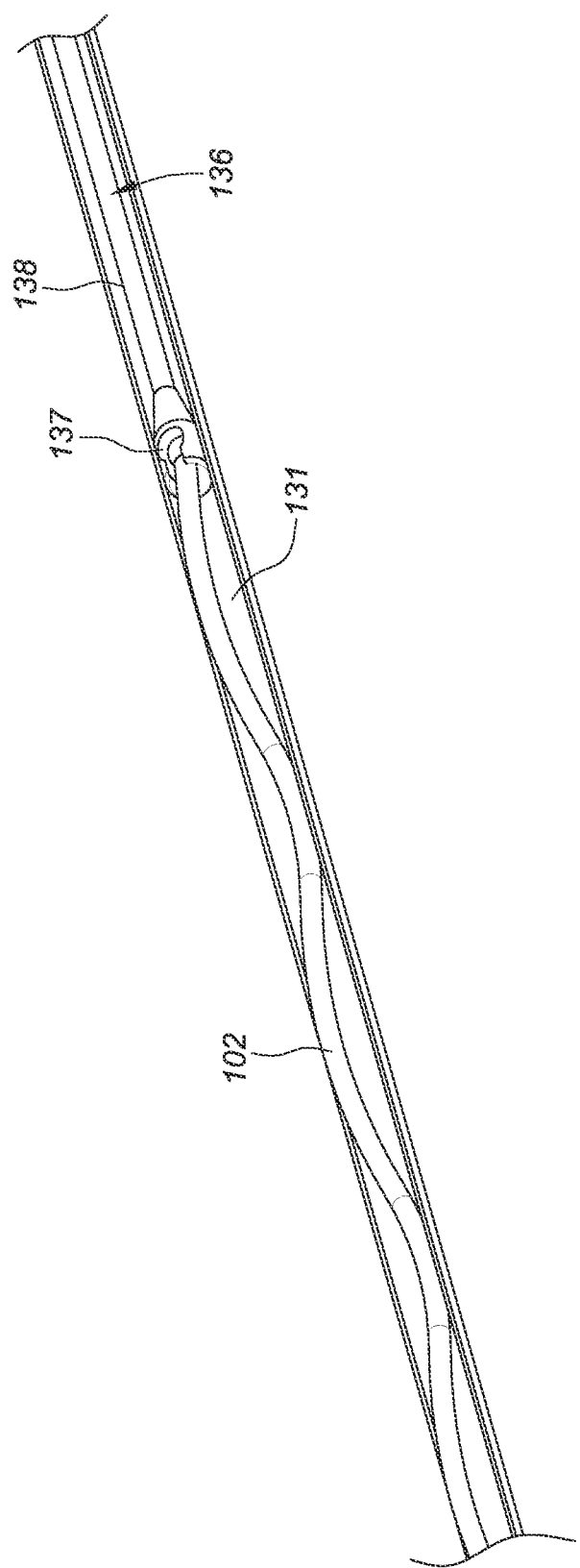
FIGS. 3A-3C are perspective views depicting example embodiments of a grasper component in use within a delivery system.

Release of the proximal end of implant 102 is also controllable. FIG. 3A is a partial cross-sectional view depicting an example embodiment of system 100 with a portion of implant 102 shown within inner lumen 131 of inner shaft 130. Here, implant 102 is in the lineated state prior to deployment with proximal engagement member 115 coupled with a grasper 136 that is slidable distally and/or proximally within lumen 131. Grasper 136 can include a distal end region 137 on or coupled with a shaft 138. Grasper 136 is preferably controllable to rotate and longitudinally translate (e.g., push and pull) implant 102 with respect to inner shaft 130.

Figure 3B:
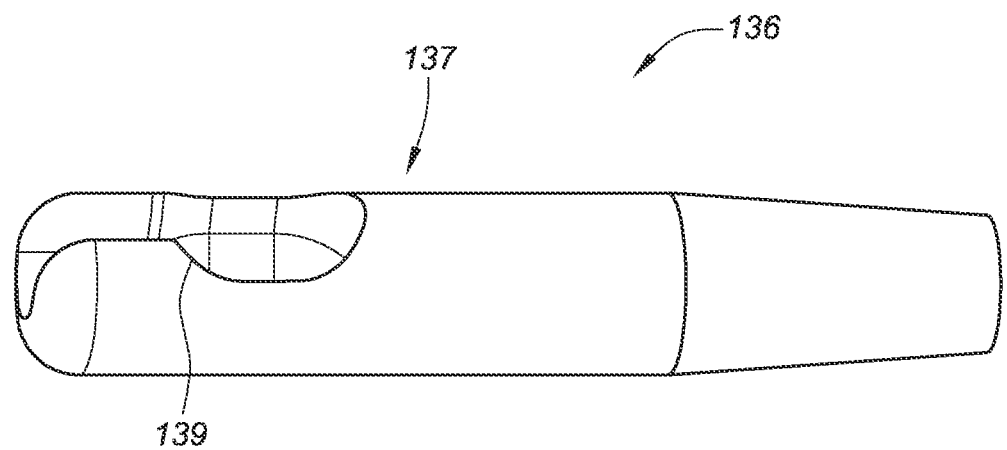
Figure 3C:
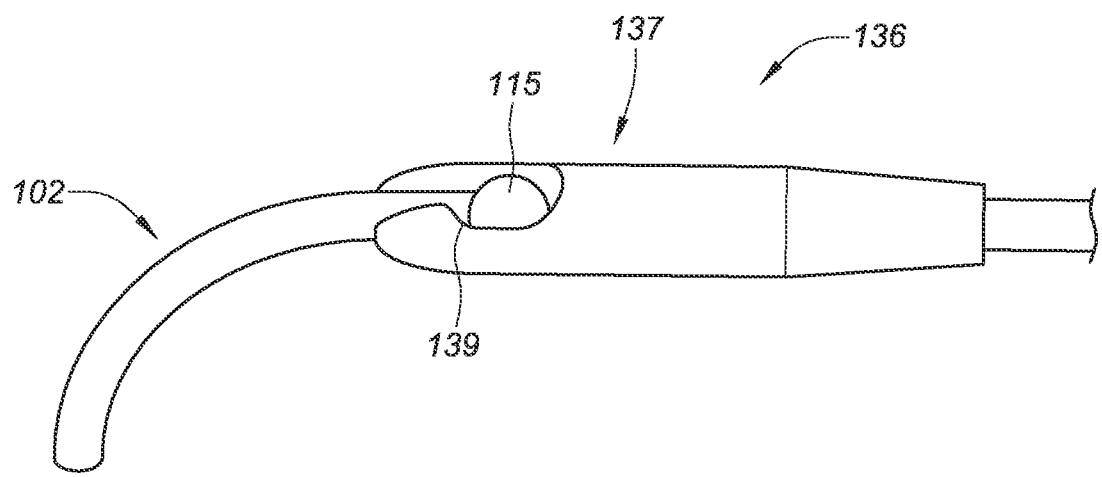

FIGS. 3B and 3C are perspective views depicting an example embodiment of distal end region 137 of grasper 136 without implant 102 and with implant 102, respectively. Grasper 136 includes a recess (also referred to as a cavity or pocket) 139 for receiving and holding proximal engagement member 115. Here, the enlarged portion 115 is retained within recess 139 by a distal necked down region having a relatively smaller width. While within inner lumen 131, the sidewalls of inner shaft 130 maintain proximal engagement member 115 within recess 139. When distal end region 137 exits inner lumen 131 (either by retracting inner shaft 130 with respect to grasper 136 or by advancing grasper 136 with respect to inner shaft 130), the restraint imparted by the inner shaft sidewalls is no longer present and engagement member 115 is free to release from grasper 136. Thus, when the physician is satisfied with placement of the deployed implant 102, distal engagement member 114 can be released by moving retainer 142 and permitting distal engagement member 114 to decouple from control member 140, and proximal engagement member 115 can be released by exposing grasper 136 from within inner shaft 130 and permitting proximal engagement member 115 to decouple from grasper 136.

Grasper 136 can also assist in loading implant 102. In some embodiments, application of a tensile force on implant 102 with grasper 136 (while the opposite end of implant 102 is secured, for example, by retainer 142) facilitates the transition of implant 102 from the at-rest configuration to a lineated configuration suitable for insertion of implant 102 into inner shaft 130.

Anchor delivery member 150 can have multiple different configurations and geometries (e.g., including those that extend in one direction across the bladder wall, two directions across the bladder wall (e.g., left and right), or three or more directions across the bladder wall). Additional examples of anchor delivery members and anchors are described in FIGS. 2B and 4A-4J of International Application No. PCT/US19/32637, filed May 16, 2019, which was previously incorporated by reference in its entirety for all purposes.

Upon completion of the implant deployment procedure, anchor 152 can be collapsed or retracted to permit removal of delivery device 103. For instance, in embodiments where anchor 152 is a balloon, that balloon is deflated and optionally retracted back into a lumen of device 103, and subsequently withdrawn from the bladder and urethra. In embodiments where anchor 152 is a wire form or other expandable member (such as those described with respect to FIGS. 4A-4G of International Application No. PCT/US19/32637, filed May 16, 2019, which was previously incorporated by reference in its entirety for all purposes), anchor 152 is retracted back into the lumen of device 103 from which it was deployed, and device 103 can subsequently be withdrawn from the bladder and urethra. Retraction can be accomplished using fluid or pneumatic actuation, a screw type mechanism, or others.

Example Embodiments of Proximal Control Devices and Related Methods

Figure 5C:
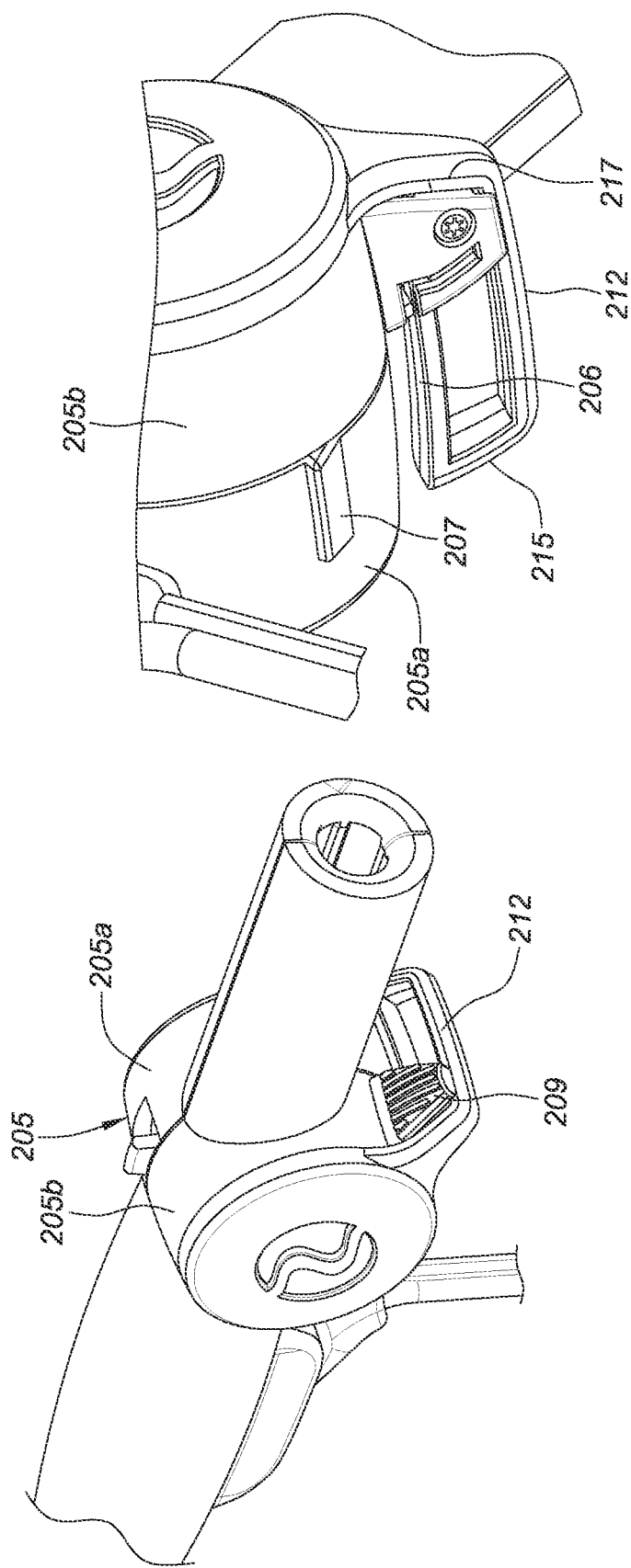
FIGS. 5C-5F are perspective views depicting an example embodiment of a steering lock device.
Figure 5D:
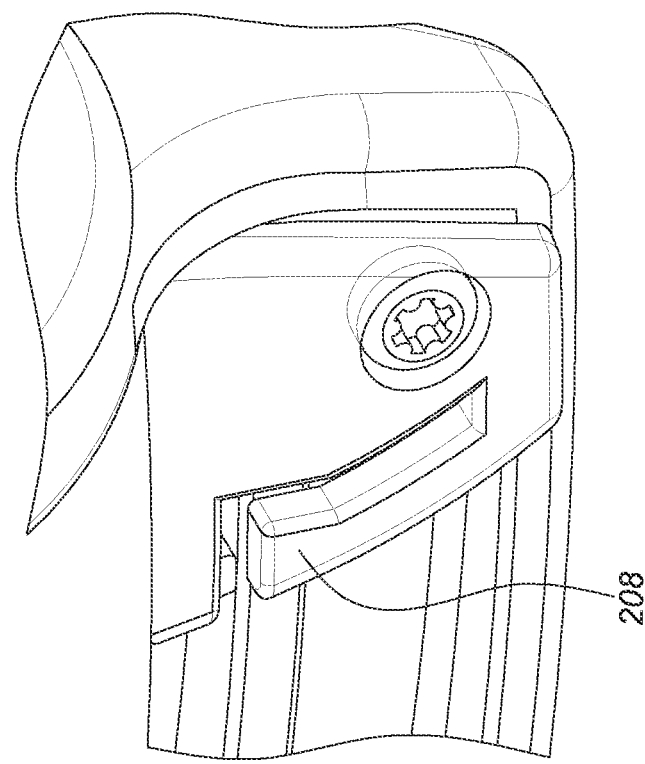
Figure 5D:
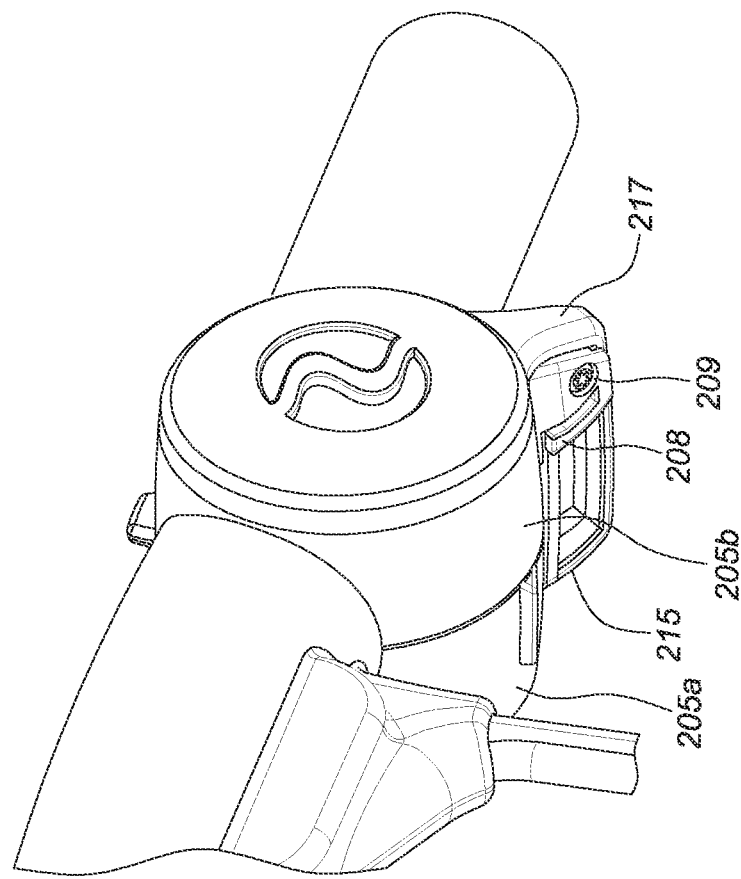

FIG. 5A is a side view depicting an example embodiment of delivery system 100 prior to deployment of implant 102, and FIG. 5B is a side view depicting this embodiment with implant 102 in a deployed configuration (anchor delivery member 150 and distal control member 140 are not shown). In this embodiment proximal control device 200 is a handheld device having a handle 201, a first user actuator 202 (configured in this example as a trigger), a main body 203, and a second user actuator 205. A longitudinal axis of delivery device 103 is indicated by dashed line 204. Proximal control device 200 can include mechanisms that are manually powered by actuation of actuator 202 to cause relative motions of the components of device 103. In other embodiments, proximal control device 200 can utilize electrically powered mechanisms instead. Second user actuator 205 can be configured to control steering of delivery device 103. Here, as seen in FIGS. 5G and 5H, actuator 205 is configured as a rotatable wheel 225 that can wind or unwind a pull wire 221 within delivery device 103 and cause deflection of device 103 upwards and downwards as depicted here. Second user actuator 205 includes an extension 212 having paddle 206 extending from a first end 215 of the extension 212. As seen in FIG. 5A, prior to deployment, the extension 212 is closer to handle 201, e.g., extension 212 is angled toward handle 201. As seen in FIG. 5B, after implant 102 has been at least partially deployed from distal end region 104, extension 212 is angled away from handle 201 and angled or pointed towards distal end region 104. The dotted lines in FIG. 5B also indicate that the distal end of the inner tubular member 120 can be deflected to enable placement of the implant further anteriorly. Proximal control device 200 can be configured so that, after all of ring-shaped structures 111 have been deployed from inner lumen 131 but prior to advancement of proximal engagement feature 115 and recess 139 from within lumen 131, further deployment of implant 102 is automatically prevented. This provides the physician with an opportunity to verify that implant 102 has been properly deployed and placed prior to releasing implant 102 from delivery device 103. A detailed description of the control device 200 and the parts and gear assemblies contained therein, can be found in, e.g., FIGS. 6A-9F, of International Application No. PCT/US19/32637, filed May 16, 2019, which was previously incorporated by reference in its entirety for all purposes.

The device may also include a steering lock that enables the user to lock the steering anteriorly to place the implant in a more anterior position. As discussed previously, the steerability of the device can include a pull wire 225 that extends from distal end region 104 of delivery device 103 (e.g., where the distal ends of the pull wires are secured to a plate or other structure within distal end region 104) to proximal control device 200, where they can be manipulated by the user to steer delivery device 103. The steering structures can be located in one or more lumens of outer shaft 120, or can be coupled to or embedded within a sidewall of outer shaft 120. Delivery device 103 can be biased to deflect in a particular lateral direction (e.g., bend) such that device 103 automatically deflects in that manner and forces imparted to steer delivery device 103 are in opposition to this biased deflection.

The steering lock is part of extension 212 attached to actuator 205. As seen in FIGS. 5C-5H, actuator 205 includes a rotatable wheel 225, an extension 212, a latch 209, and a ledge 207. The housing of actuator 205 may include two halves, a right handle half 205a and a left handle half 205b. The rotatable wheel 225 is adapted to wind and unwind the pull wire and is located in and coupled to the housing. Extension 212 includes latch 209 and paddle 206, which extends from a first end 215 and terminates in detent 208, such that a gap exists between detent 208 and a second end 217 of extension 212. The second end 217 of extension 212 is attached to left handle half 205b and the first end is adjacent a portion of the right handle half 205a. The second end 217 of extension 212 includes the detent 208 and gap. The steering lock also includes ledge 207 that extends from right handle half 205a of the housing in proximity to the first end 215 of extension 212. Latch 209 is adapted to actuate or slide along the paddle 206. When latch 209 is located on the second end 217, detent 208 frictionally engages latch 209, thereby restraining latch 209 to the second end 217.

Figure 5E:
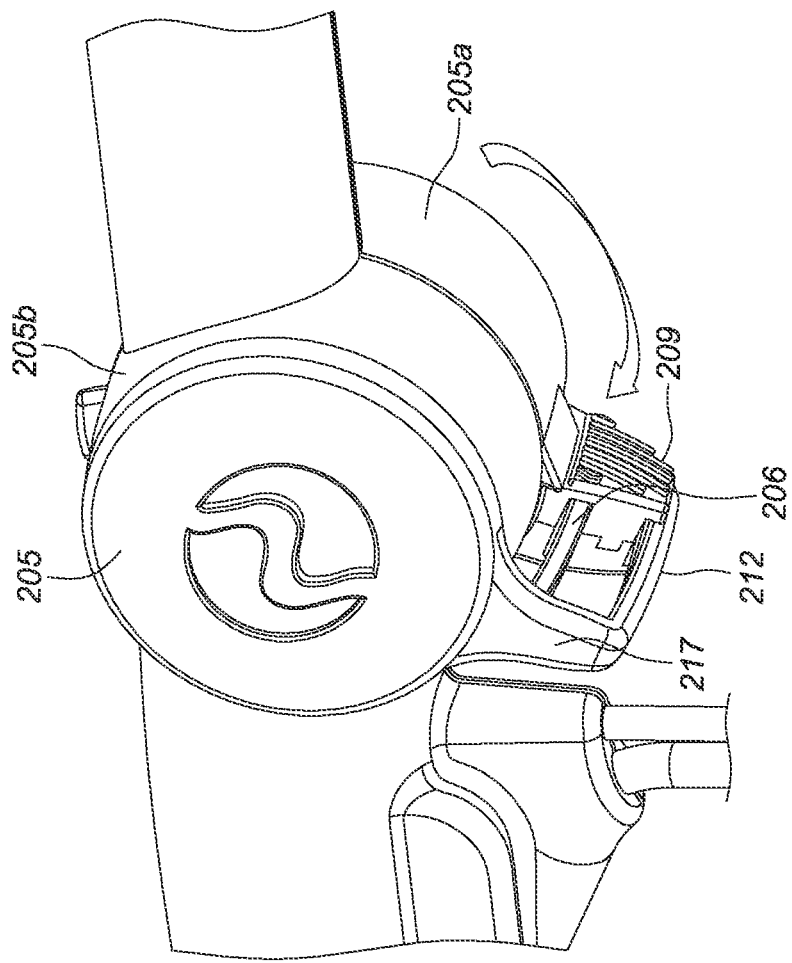
Figure 5E:
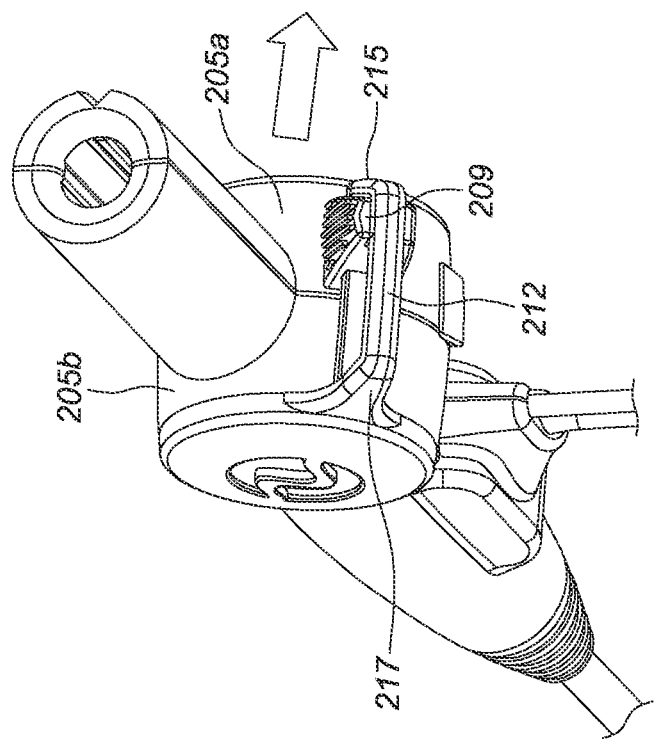
Figure 5F:
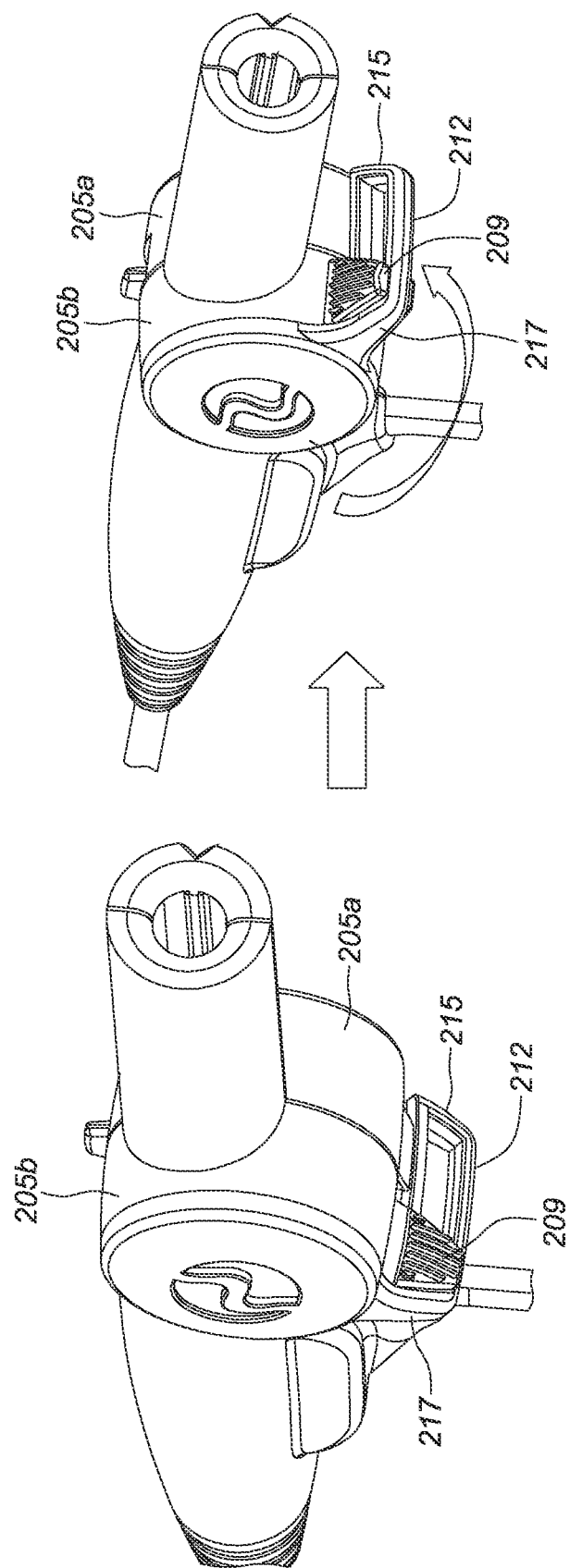
Figure 5G:
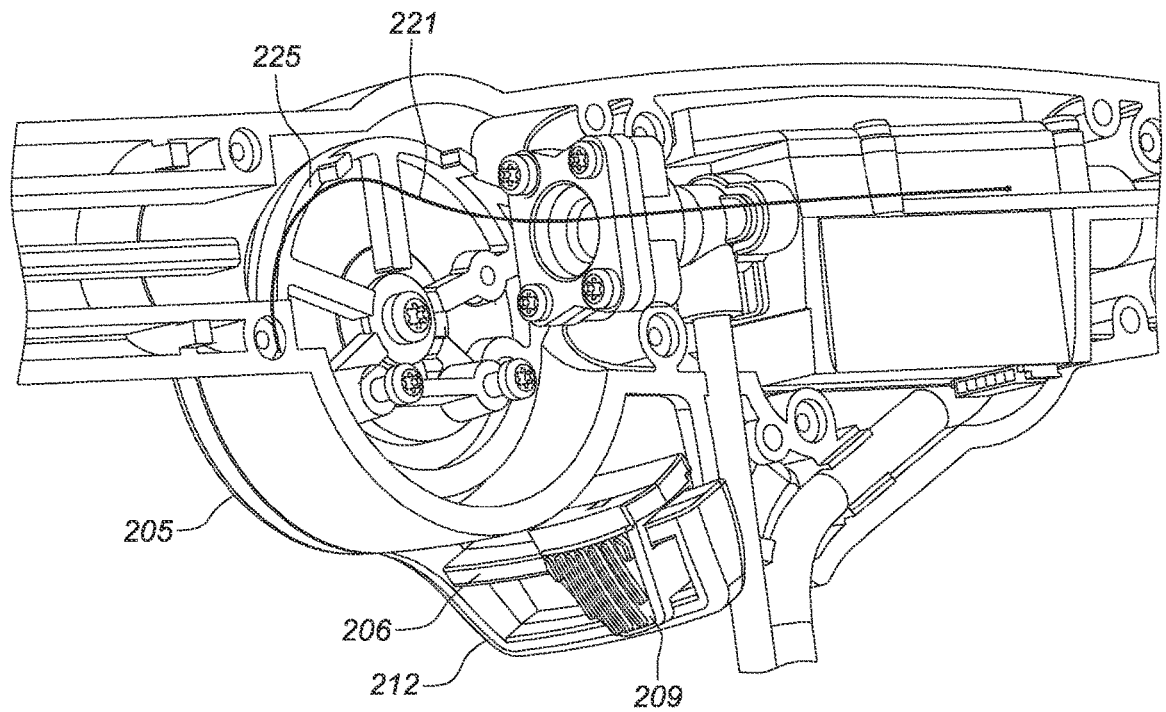
FIGS. 5G-5H are cross-sections depicting an example embodiment of a steering lock device.
Figure 5H:
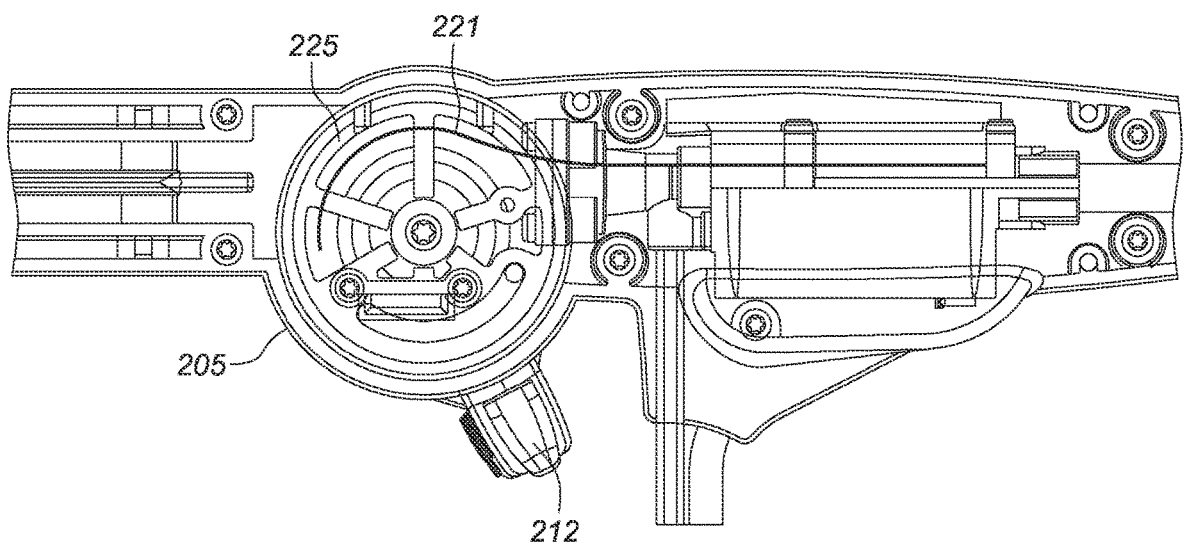

In use, as seen in FIG. 5E, the user can disengage latch 209 from detent 208 and move latch 209 along paddle 206 from the second end 217 to the first end 215 of extension 212. Once latch 209 is at the first end 215, extension 212 can be pushed in a direction towards distal end region 104 by the user until latch 209 comes into contact with ledge 207. Ledge 207 then frictionally engages latch 209 and holds extension 212 in a position angled toward distal end region 104 in a "locked" position. In the locked position, the rotatable wheel 225 cannot wind or unwind the pull wire 221 and the user cannot move (deflect or straighten) the distal end region 104 of the outer tubular member 103. As seen in FIG. 5F, to release paddle 206 from the "locked" position, the user can release latch 209 from ledge 207 and slide latch 209 along paddle 206 from the first end 215 to the second end 217 of extension 212. When latch 209 is no longer frictionally engaged by ledge 207, extension 212 can passively return to a rest position in which extension 212 is angled toward handle 201 (i.e., away from distal end region 104) due to spring-loading. In the unlocked position, the rotatable wheel 225 is capable of winding and unwinding the pull wire 221, thereby moving (deflecting or straightening) the distal end region 104 of the outer tubular member 103.

Example Embodiments of Delivery Methods

Figure 6A:
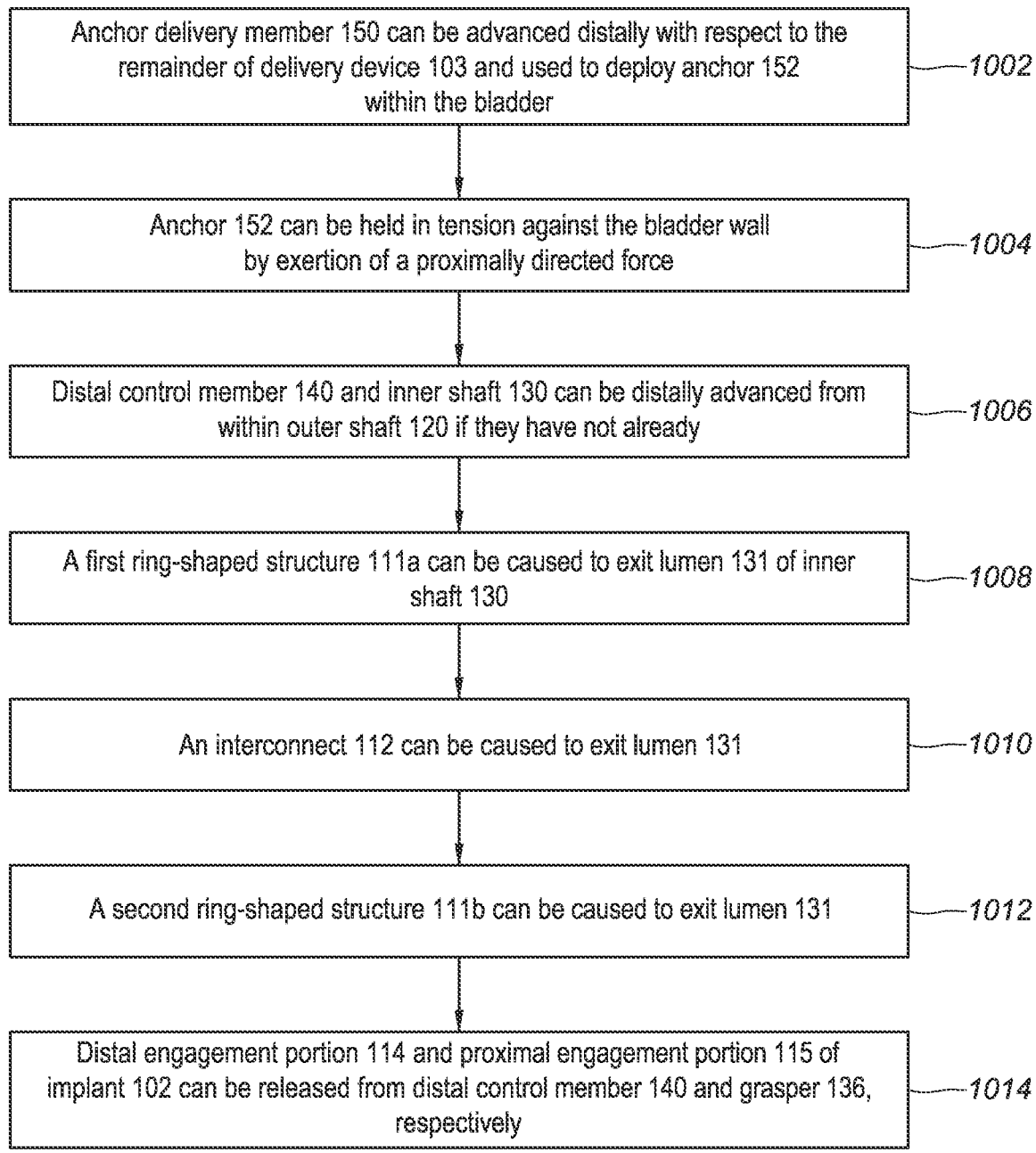
FIG. 6A is a flowchart depicting an example embodiment of a method for delivering an implant.

FIG. 6A is a flow diagram depicting an example embodiment of a method 1000 of delivering implant 102 using system 100. Distal end region of outer shaft 120 is inserted into the urethra, preferably with inner shaft 130, distal control member 140, and anchor delivery member 150 in retracted states fully contained within outer shaft 120 such that no part is extending from the open distal terminus of outer shaft 120. After advancement into the urethra, at step 1002 anchor delivery member 150 is advanced distally with respect to the remainder of delivery device 103 (e.g., members 120, 130, and 140) and used to deploy anchor 152 within the bladder. In some embodiments, deployment of anchor 152 can be the inflation of one or more balloons (e.g., as depicting in FIG. 2B,) by the introduction of an inflation medium through an injection (e.g., luer taper) port. The longitudinal positioning (e.g., advancement and retraction) of anchor delivery member 150 and/or any wire-form members can be accomplished manually by the user manipulating a proximal end of anchor delivery member 150 and/or any wire-form members either directly or with proximal control device 200.

At step 1004, anchor 152 can be held in tension against the bladder wall by exertion of a proximally directed force on device 200. Anchor 152 can therefore provide an ordinate for system 100 from which to deploy implant 102 in an accurate location. This feature can ensure the implant is not placed too close to the bladder neck.

At 1006, distal control member 140 and inner shaft 130 can then be distally advanced from within outer shaft 120 if they have not already (for example, step 1006 can occur prior to steps 1002 and/or 1004). The user can manipulate the position of proximal control device 200 with the aid of imaging (as described herein) until implant 102 is in the desired position. Once implant 102 is in the desired position, the implant deployment procedure can begin. The steps for implant deployment can be performed automatically by user actuation of proximal control device 200 (e.g., actuation of trigger 202, selection of a position for switch 604, etc.), or the steps can be performed directly by hand manipulation of each component of delivery device 103, or by a combination of the two as desired for the particular implementation.

In some embodiments, deployment of implant 102 from within lumen 131 is fully accomplished by (1) distally advancing grasper 136 with respect to inner shaft 130, while inner shaft 130 is not moved, while in other embodiments, deployment of implant 102 from within inner lumen 131 is fully accomplished by (2) proximally retracting inner shaft 130 with respect to grasper 136 while grasper 136 is not moved. In some embodiments, deployment of implant 102 is fully accomplished by (3) a combination of both movements. In still other embodiments, deployment of implant 102 is fully accomplished by (1), (2), or (3) in combination with one or more rotations of inner shaft 130, in one or more directions (e.g., clockwise or counterclockwise) with respect to distal control member 140.

An example embodiment of a sequence of steps 1008, 1010, and 1012 for deploying implant 102 is described with reference to FIG. 6A and the timing diagram of FIG. 6B. First with reference to FIG. 6A, at step 1008 a first ring-shaped structure 111a is caused to exit lumen 131 of inner shaft 130, at step 1010 an interconnect 112 is caused to exit lumen 131, and at step 1012 a second ring-shaped structure 111b is caused to exit lumen 131. Steps 1010 and 1012 can be repeated for each additional interconnect 112 and ring-shaped structure 111 present on implant 102.

Figure 6B:
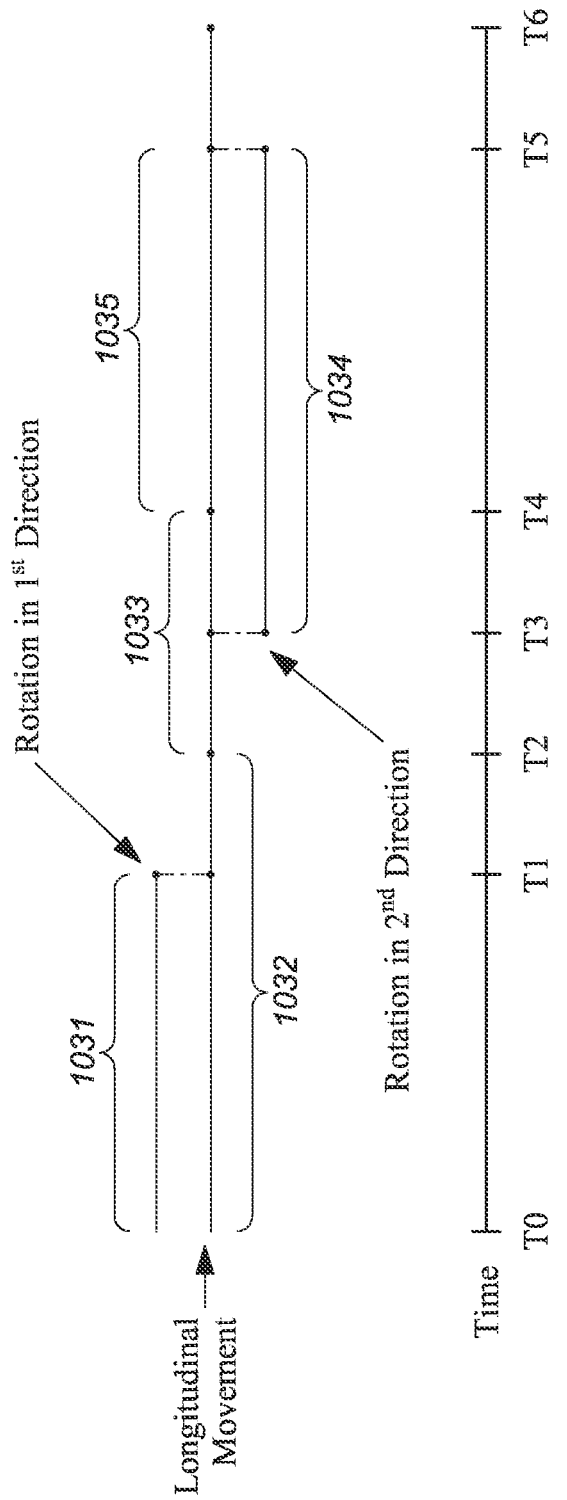
FIG. 6B is a timing diagram depicting an example embodiment of a sequence of steps for deploying an implant.

In FIG. 6B, step 1008 begins at the far left of the timing diagram at T0. Deployment of ring-shaped structure 111a corresponds to the duration of time marked 1008, deployment of interconnect 123 corresponds to time span 1010, and deployment of ring-shaped structure 111b corresponds to time span 1012. Those of ordinary skill in the art will recognize that the differentiations between deployment of a ring-shaped structure 111 and deployment of an interconnect 112 are approximations as the transitions between those portions of implant 102 can be gradual and do not have to have precise demarcations.

The embodiment described with respect to FIG. 6B is for an implant with ring-shaped structures 111 having opposite directions of winding (e.g., clockwise, then counterclockwise, then clockwise, etc.). Three different motions are indicated in FIG. 6B. At top is rotational motion of inner shaft 130 in one direction (e.g., clockwise), in the middle is longitudinal motion (e.g., proximal or distal) of one or more components of delivery device 103, and at bottom is rotational motion inner shaft 130 in the direction opposite (e.g., counterclockwise) that indicated at top. In embodiments where ring-shaped structures 111 of implant 102 are all wound in the same one direction, rotation of inner shaft 130 will also be in only one direction.

From time T0 to T1, deployment of implant 102 is accomplished by rotating inner shaft 130, as indicated in region 1031. At the same time, in region 1032, grasper 136, and thus implant 102, is distally advanced without moving outer shaft 120 longitudinally (neither distally nor proximally) nor rotationally, and also without longitudinally moving inner shaft 130 (neither distally nor proximally).

From time T1 to T2, rotation of inner shaft 130 is stopped but distal advancement of grasper 136 continues while shafts 120 and 130 do not move longitudinally.

From time T2 to T4, deployment of a first interconnect 112 takes place. In region 1033, from time T2 to T4, no distal advancement of grasper 136 (and implant 102) occurs. Deployment of interconnect 112 is accomplished by proximal retraction of both outer shaft 120 and inner shaft 130 while holding grasper 136 in place. This causes interconnect 112 to exit inner lumen 131 of shaft 130.

With respect to rotation of inner shaft 130, from time T2 to T3 no rotation of inner shaft 130 occurs. Within proximal control device 200 the interrupted portion of annular gear 802 continues and there is no rotation of shaft 130 by central gear 816.

In embodiments where interconnect 112 is straight, then it can be desirable to refrain from rotating shaft 130 while interconnect 112 is deployed from time T2 to T4. For embodiments where interconnect 112 is curved, such as the embodiment of FIGS. 1B-1D, it may be desirable to initiate rotation of inner shaft 130 during interconnect deployment. FIG. 6B depicts deployment for a curved interconnect 112, and from T3-T4 inner shaft 130 is rotated in the opposite direction as indicated by region 1034.

At T4, deployment of interconnect 112 is complete and deployment of second ring-shaped structure 111b begins. Proximal retraction of shafts 120 and 130 is stopped as indicated by the cessation of region 1033. Distal advancement of grasper shaft 138 is restarted in region 1035 at T4, while outer shaft 120 is not moved rotationally nor longitudinally. Rotation of inner shaft 130 continues as indicated in region 1034, but inner shaft 130 is not moved longitudinally These motions continue until time T5, at which point rotation of inner shaft 130 is stopped. Within proximal control device 200, an interrupted portion of annular gear 802 is reached and gear 802 disengages from the planetary gears and rotation of central gear 816 is stopped. User depression of trigger 202 continues from time T5-T6, the components operate with similar motions as described from time T1 to T2. If another interconnect 112 and ring-shaped structure 111 are present, then the sequence beginning at time T6 can be the same as that described beginning at time T2 and continuing to time T6.

In many embodiments described here, deployment of all of ring-shaped structures 111 can occur with a single continuous depression of trigger 202. In all of these embodiments, proximal control device 200 can instead be configured such that repeated pulls of trigger 202 are required to deploy all of ring-shaped structures 111 of implant 102.

During deployment, e.g., after time T0 up until completed deployment of the proximal-most ring-shaped structure 112, if the physician wishes to recapture implant 102, then depression of trigger 202 can be stopped. Trigger 202 can be spring-loaded or otherwise biased to return to the outermost position. See FIG. 6B.

If the physician is satisfied with deployment, then at 1014 distal engagement portion 114 and proximal engagement portion 115 of implant 102 can be released from distal control member 140 and grasper 136, respectively. By way of example, in proximal control device 200 the physician can pull tab 910 to permit trigger 202 to be depressed the rest of the way, which in turn can deploy proximal engagement portion 115 of implant 102, either by distal advancement of grasper 136, proximal retraction of shafts 120 and 130, or both. A tab can be coupled with control wire 146 and the pulling of the tab can pull wire 146 and remove retainer 142 from distal engagement portion 114.

Anchor 152 can then be recaptured (e.g., deflation of the balloon or retraction of the wire-form members) and withdrawn into anchor delivery member 150 if desired. Anchor delivery member 150, distal control member 140, and inner shaft 130 can be retracted into outer shaft 120 and then withdrawn from the urethra.

A more detailed description of the process by which the components in the control device accomplish the above steps is provided in International Application No. PCT/US19/32637, filed May 16, 2019, which was previously incorporated by reference in its entirety for all purposes.

Example Embodiments of User Assembly of Proximal Control Device

Referring back to FIG. 5A, proximal control device 200 can include a movable (e.g., retractable and/or advanceable) handle portion 1102 that can move with respect to the more proximally located handle portion 1103. FIG. 5A depicts movable handle portion 1102 in a distally advanced position prior to deployment of implant 102 and FIG. 5B depicts portion 1102 in a proximally retracted position after deployment of implant 102. Movable portion 1102 can be secured to and moved with outer shaft 120, and can also be moved independently of inner shaft 130, distal control member 140, and anchor delivery member 150 (not shown).

A more detailed description of embodiments of the proximal control device is provided in International Application No. PCT/US19/32637, filed May 16, 2019, which was previously incorporated by reference in its entirety for all purposes. Additional details may be found in U.S. Publ. No. 2021/0145619, which is hereby incorporated by reference in its entirety for all purposes.

Example Embodiments of Implant Placement

Figure 7:
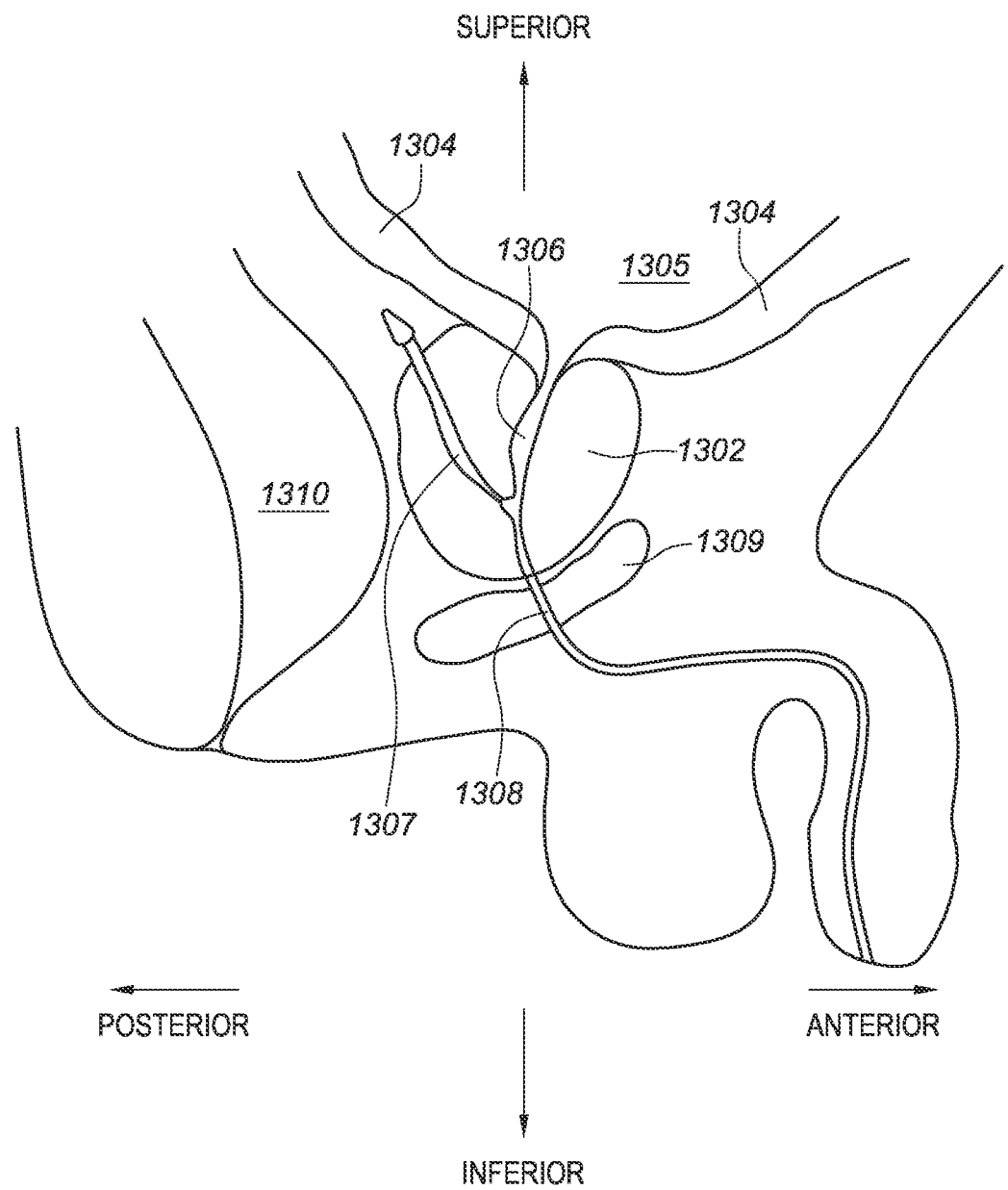
FIG. 7 is an example cross-section of the male anatomy.

All the embodiments of system 100 described herein can be used to deliver implant 102 to various locations in proximity to the prostate gland, or other locations within the human anatomy. FIG. 7 is a cross-section of the male anatomy that provides context for use in describing various examples of implantation locations within the prostatic urethra. Here, prostate gland 1302 is centrally located with bladder wall 1304 and bladder 1305 located superiorly. The prostatic urethra 1306 extends inferiorly from bladder 1305 past ejaculatory duct 1307 and through prostate gland 1302. The prostatic urethra 1306 becomes the membranous urethra 1308 at the general location of the external urethral sphincter 1309 and continues on to exit the body. The rectum is indicated by 1310.

FIG. 8A is a cross-section rotated from the viewpoint of FIG. 7 such that the posterior direction extends into the page in the anterior direction extends out of the page. Here an example embodiment of implant 102 is shown positioned within prostatic urethra 1306. Implant 102 is generally positioned centrally within prostatic urethra 1306 as viewed from this perspective, in other words, generally an equal distance from the superior and inferior edges of prostate gland 1302. Placement of implant 102 is generally at the discretion of the medical professional and can be offset either superiorly or inferiorly from the positions shown here, however a position within the prostatic urethra 1306 is generally preferred.

FIG. 8B depicts the area of prostate gland 1302 from generally the same perspective as that of FIG. 7, but with more detail. Here, prostate gland 1302 is in an enlarged state with a median lobe 1402 that protrudes into prostatic urethra 1306. FIG. 8C is a cross-section taken along line 8C-8C of FIG. 8B and shows the slit-like nature of prostatic urethra 1306 in this enlarged prostate gland 1302 where the width of urethra 1306 widens as it progresses from the anterior to the posterior side.

FIG. 8D depicts an example embodiment of a posteriorly placed implant 102 within the example anatomy described with respect to FIG. 8B and FIG. 8E is a cross-section taken along line 8E-8E of FIG. 8D. As can be seen here, implant 102 is placed generally along the posterior most surface of the prostatic urethra 1306. Implant 102 is sized to have a maximum diameter that is less than the width of prostatic urethra 1306 at its maximum central width (e.g., less than 50% of the width, less than 65% of the width, less than 80% of the width, etc.) such that implant 102 can be described as residing substantially on the posterior side of prostatic urethra 1306, and not in contact with the anterior most side of urethra 1306. The implications of this placement are shown in FIG. 8E where the opening through prostate gland 1302 that is created by implant 102 is positioned primarily on the posterior side of prostate gland 1302 and urethra 1306.

FIG. 8F depicts an example embodiment of an anteriorly placed implant 102 within the example anatomy described with respect to FIG. 8B and FIG. 8G is a cross-section taken along line 8G-8G of FIG. 8E. As can be seen here, implant 102 is placed generally along the anterior most surface of prostatic urethra 1306. Implant 102 can be sized to have a maximum diameter that is less than the width of prostatic urethra 1306 at its maximum central width (e.g., less than 50% of the width, less than 65% of the width, less than 80% of the width, etc.) such that implant 102 can be described as residing substantially on the anterior side of prostatic urethra 1306, and not in contact with the posterior most side of urethra 1306. The implications of this placement are shown in FIG. 8G where the opening through prostate gland 1302 that is created by implant 102 is positioned primarily on the anterior side of prostate gland 1302 and urethra 1306. With both the posterior placement and the anterior placement, implant 102 can still be placed generally centrally with respect to prostate gland 1302 as shown in FIG. 8A. Deployment of implant 102 in a posterior or anterior position is generally at the discretion of the medical professional. Other variations of placement can also be used including placements that are centrally located between the posterior most side and interior most side of urethra 1306, as well as variations in sizing such that implant 102 has a relatively larger or smaller diameter with respect to prostate 1302 than shown here.

Removal Methods

Figure 9A:
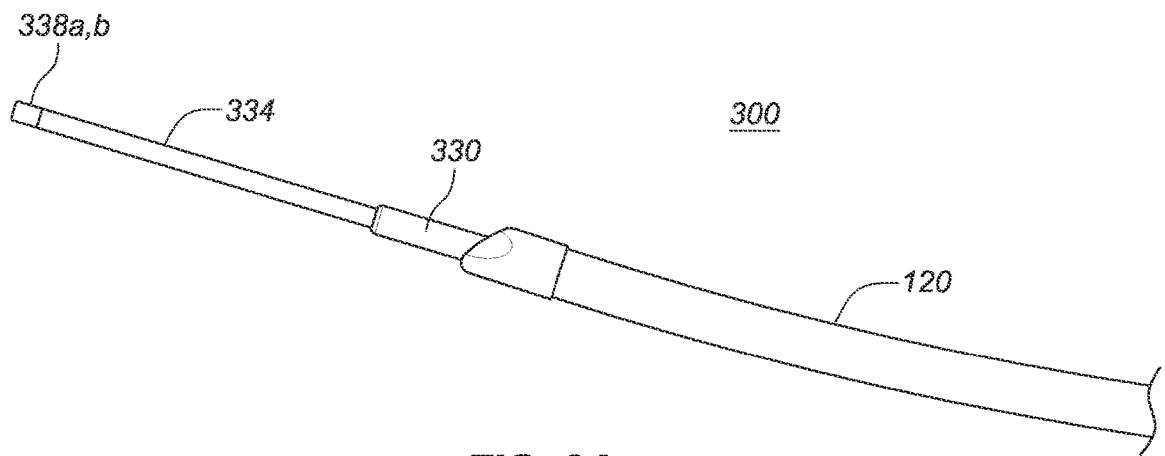
FIGS. 9A-9C is an example embodiment of a retrieval device.
Figure 9B:
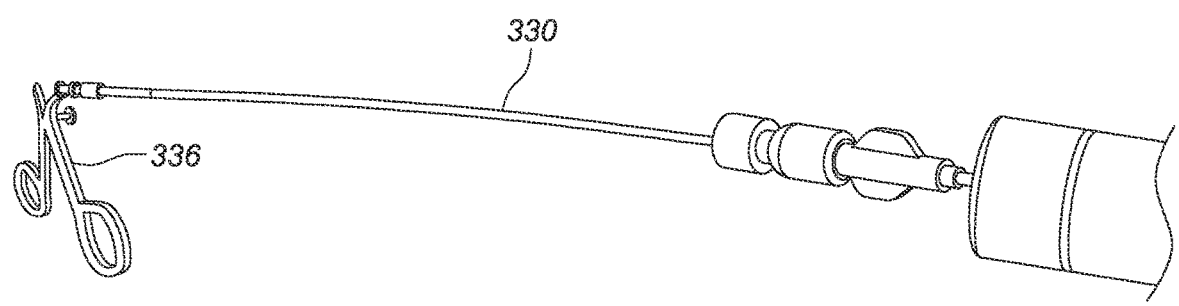
Figure 9C:
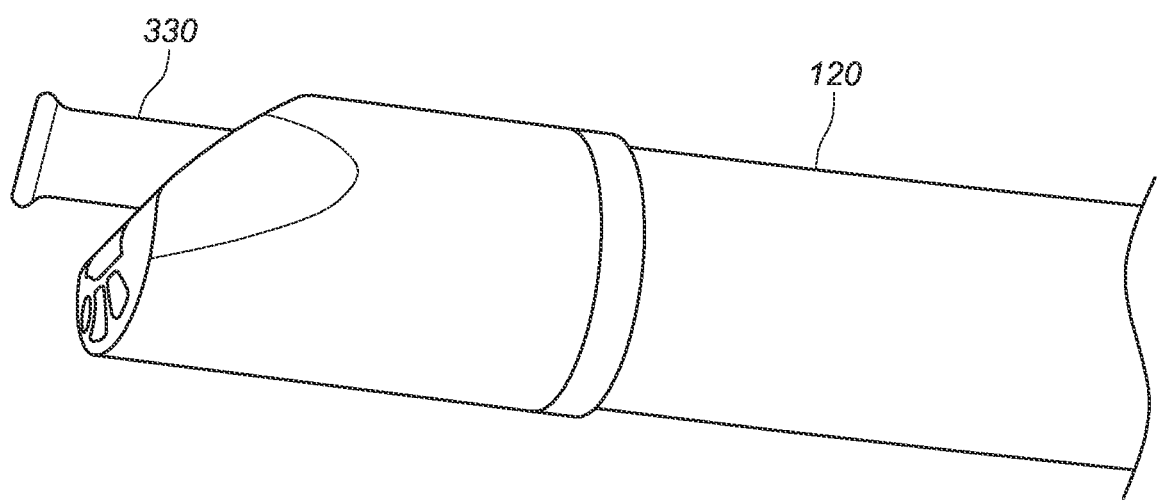
Figure 10A:
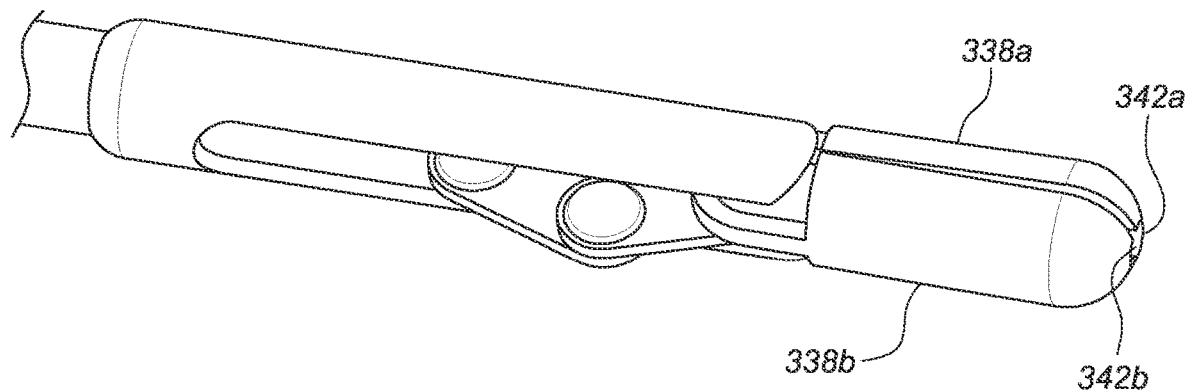
FIGS. 10A-10F are example embodiments of a distal end of a retrieval device.
Figure 10B:
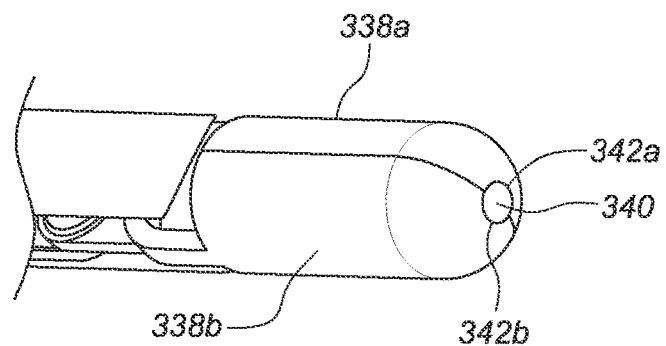
Figure 10C:
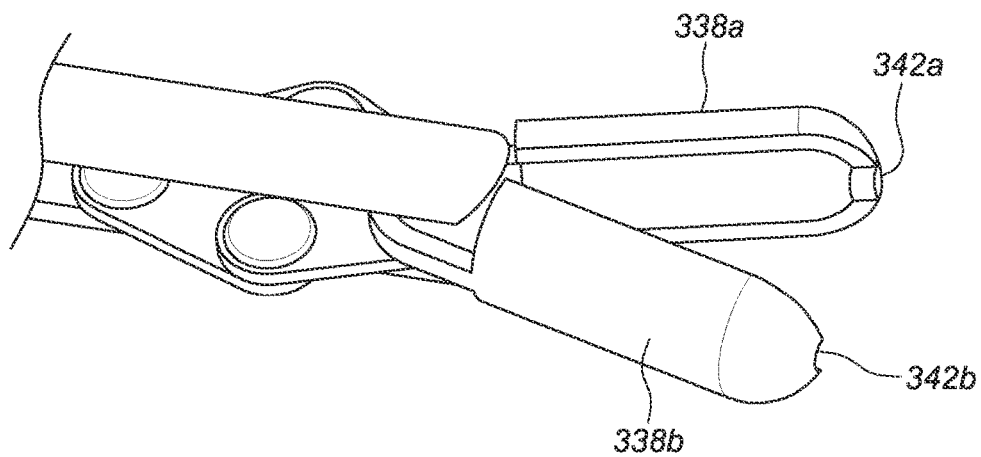
Figure 10D:
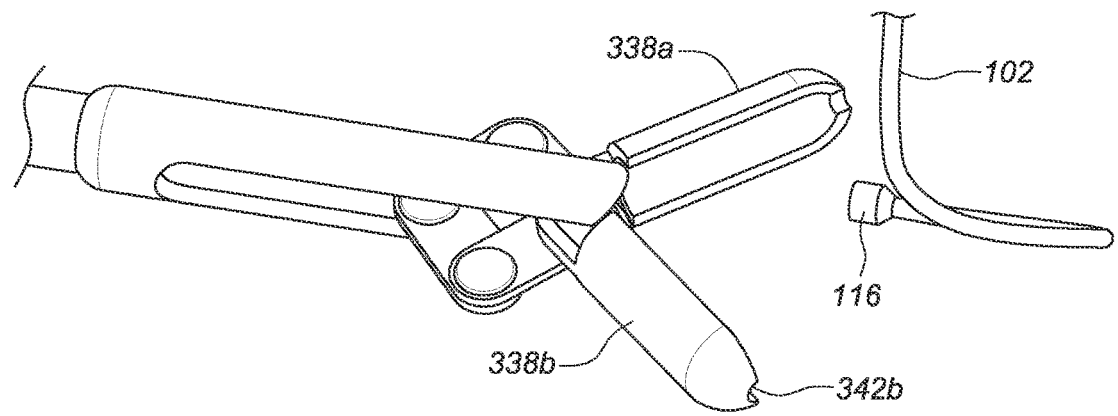
Figure 10E:
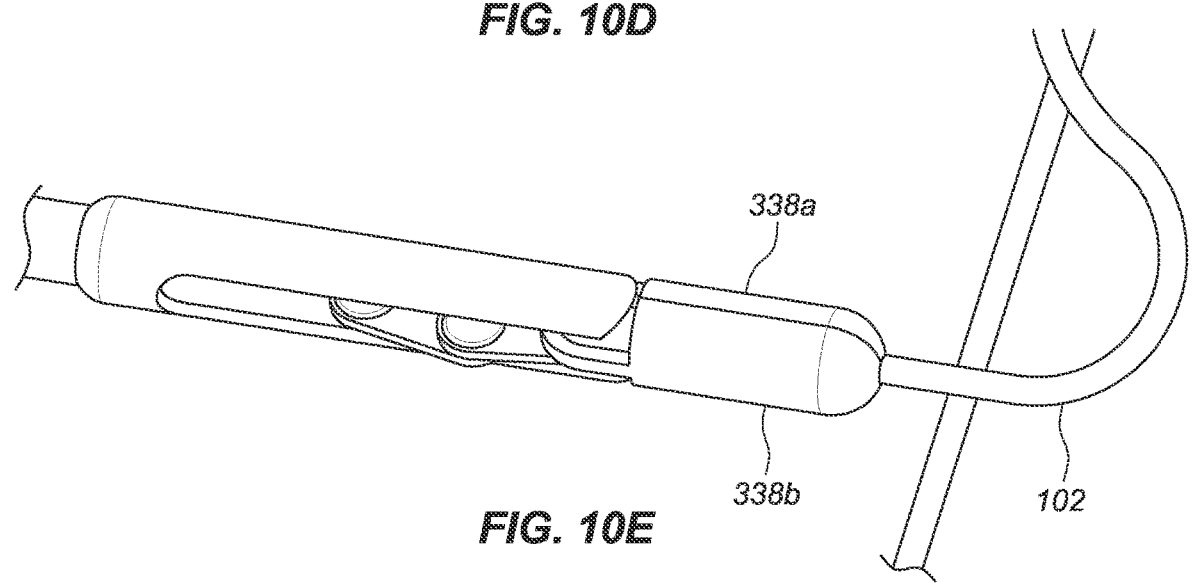
Figure 10F:
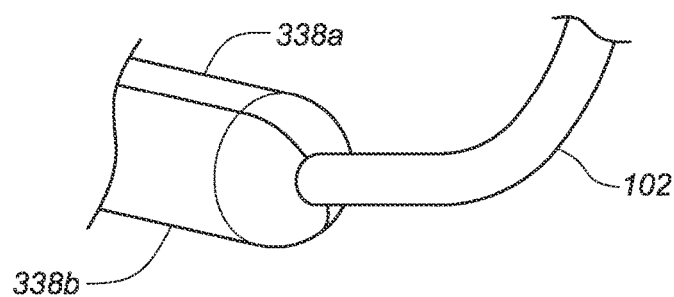
Figure 11A:
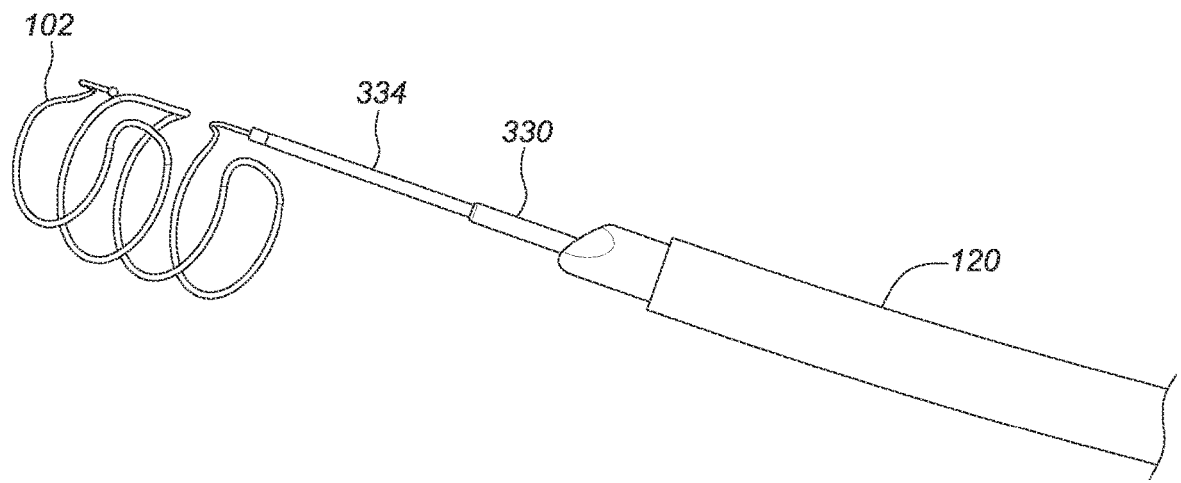
FIGS. 11A-11B are example embodiments of a retrieval device grasping an implant.
Figure 11B:
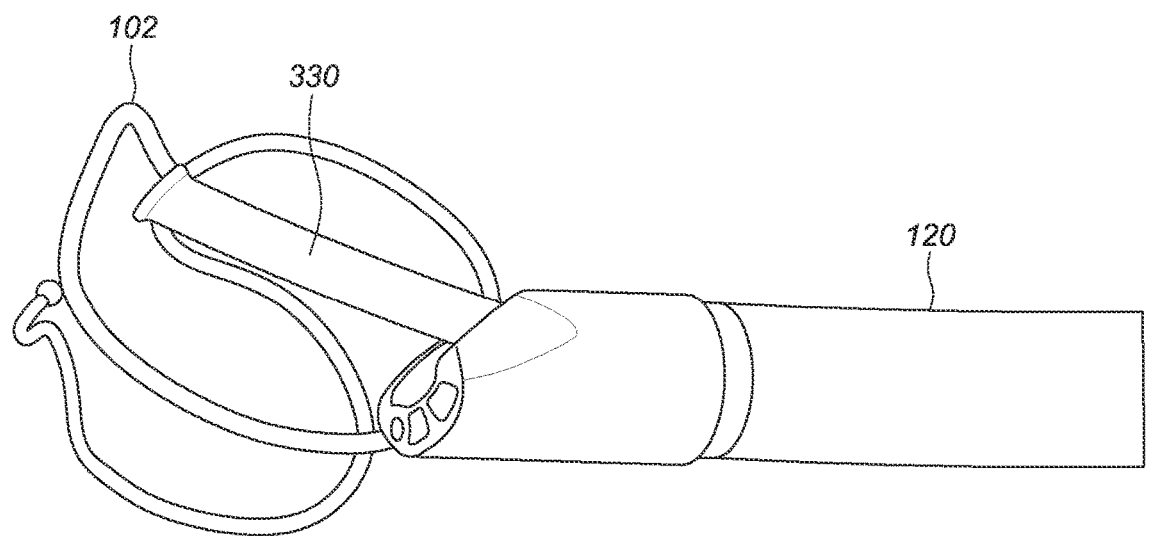

In one embodiment, the implant 102 can be removed by grasping an atraumatic end of the device and deforming the device from its expanded spiral shape to a roughly linear shape, such that it can be withdrawn through the lumen of a catheter. A retrieval device 300 configured to be inserted through the lumen 121 of outer tubular member 120 of delivery device 103 can be used for both acute and chronic retrieval of the implant 102. As depicted in FIGS. 9A-9C, delivery device 103 can be used to remove implant 102. An elongate flexible tubular member 330 can be delivered through first inner lumen 121 of outer tubular member 120. The elongate flexible tubular member 330 can be made of a polymer, e.g., PEEK. An actuating shaft 334 can be delivered through a lumen of the elongate flexible tubular member 330. The actuating shaft 334 may have forcep cups or opposed jaws 338a, b at a distal end and an actuating handle 336 configured to manipulate the opening and closing of the opposed jaws 338a, b at a proximal end. The actuating shaft 334 may also be configured to move axially relative to the elongate flexible tubular member 330 when the device handle 336 is articulated. The distal end of the actuating shaft 334 can be extended past the distal end of the elongate flexible tubular member 330, which can be extended past the distal end of the outer tubular member 120, to grasp either of atraumatic ends 116, 117, which are, e.g., rounded, spherical, cylindrical, frustoconical, or ballized of the implant 102. The opposed jaws 338a, b are configured to hold one of atraumatic ends 116, 117 within a cavity defined by the opposed jaws 338a, b in a closed configuration. As seen in FIGS. 10A-10F, the opposed jaws 338a, b may each further include a curved edge 342a, b in a distal region of the opposed jaws 338a, b, such that an opening 340 in the distal end is formed when the opposed jaws 338a, b are in the closed configuration, where the opening 340 communicates with the cavity defined by the opposed jaws 338a, b in the closed configuration. As seen in FIGS. 11A-11B, once either of atraumatic ends 116, 117 are grasped, proximal withdrawal of the articulating shaft 334 into the lumen of elongate flexible tubular member 330 will result in linearizing the implant 102 (i.e., pulling the implant into a roughly linear form) such that the implant can be withdrawn through the lumen 121 of outer tubular member 120.

Figure 12:
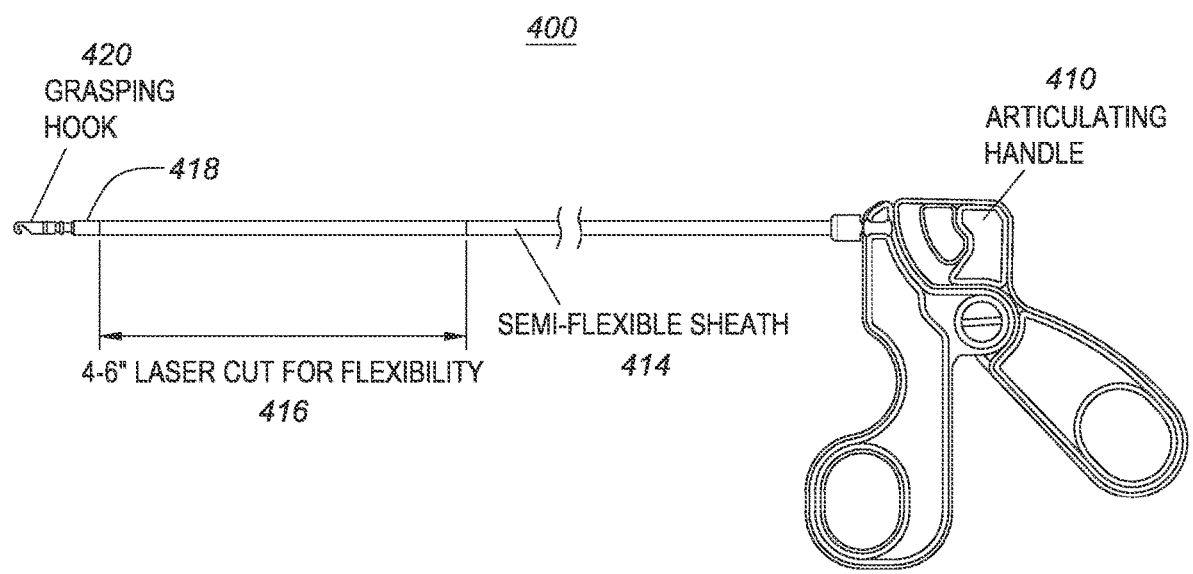
FIG. 12 is an example embodiment of an alternative retrieval device.
Figure 13A:
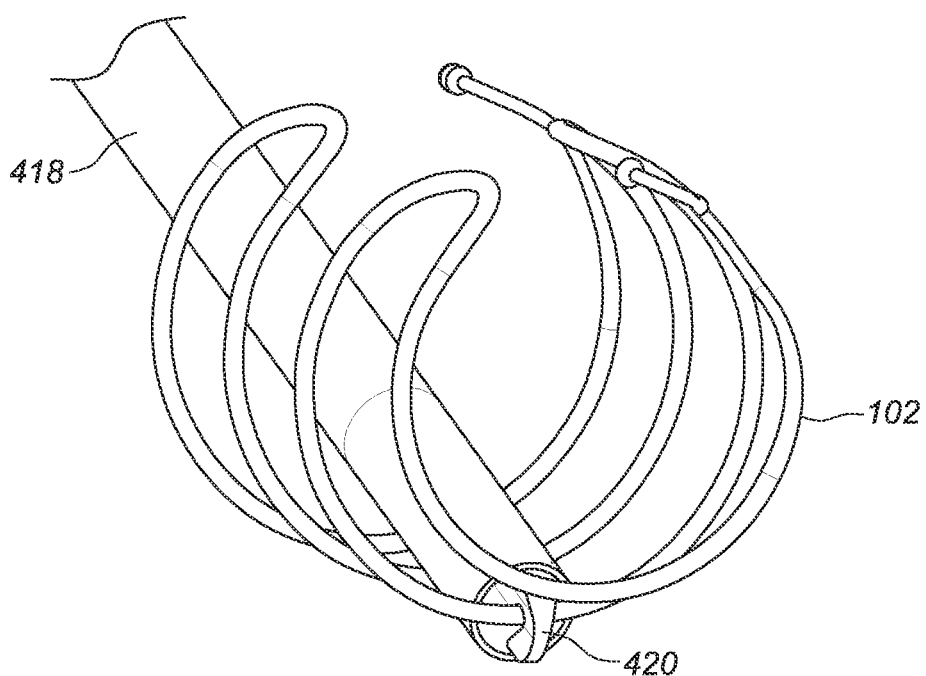
FIGS. 13A-13D depict perspective views of the distal end of the alternative retrieval device depicted in FIG. 12.
Figure 13B:
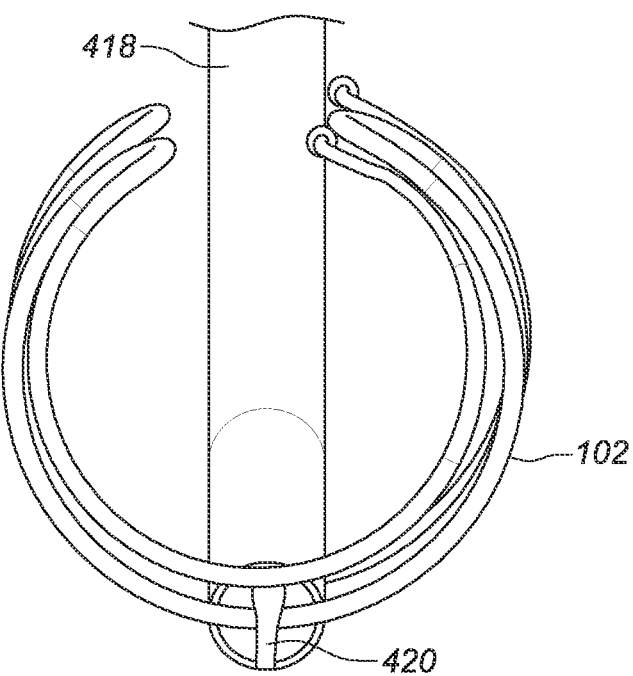
Figure 13C:
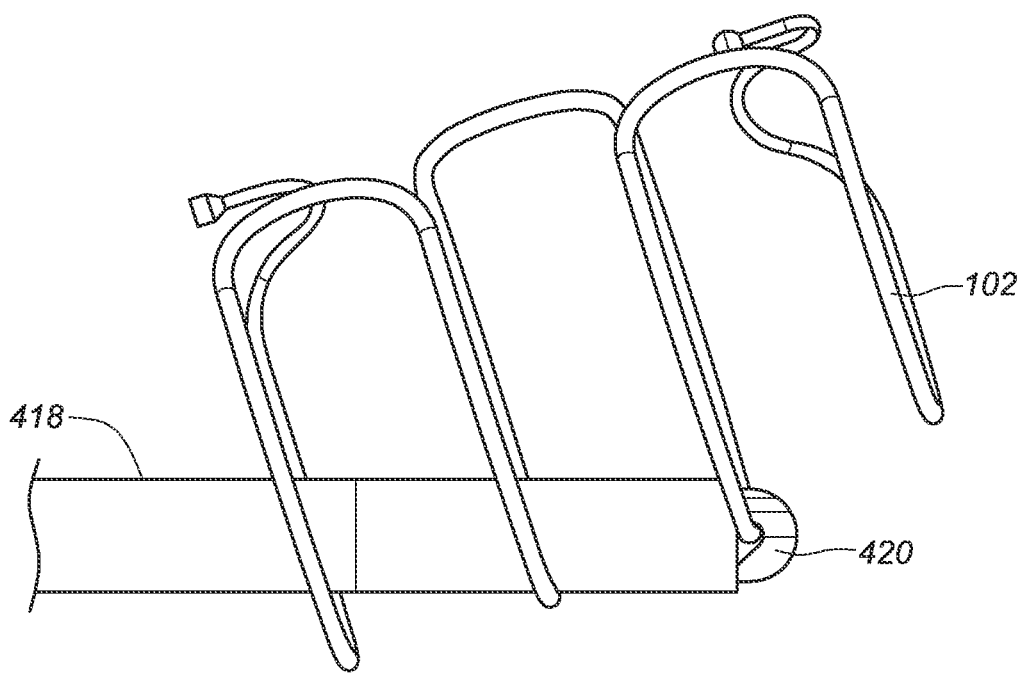
Figure 13D:
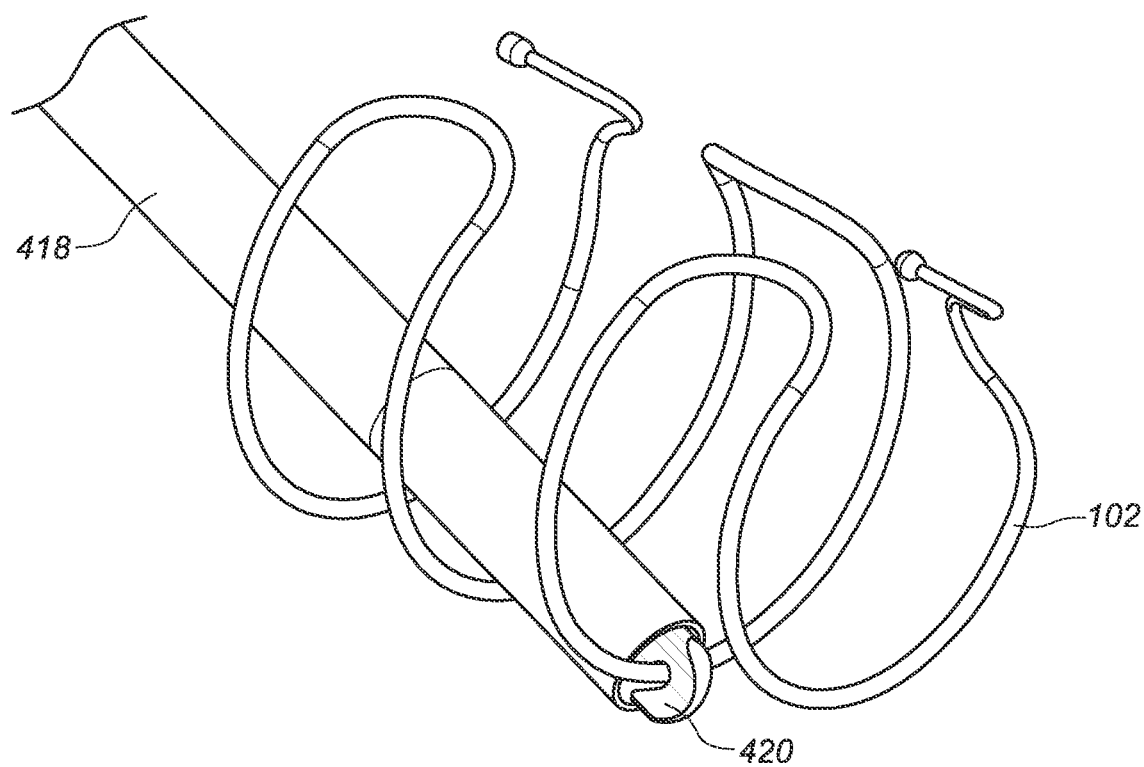

In another embodiment, the implant can be removed by grasping anywhere along the length of the implant, rather than only grasping an atraumatic end. Such a procedure could be performed in an in-office outpatient procedure. A single-use retrieval device 400 configured to be inserted through the lumen 121 of outer tubular member 120 of delivery device 103 can be used for both acute and chronic retrieval of the implant 102. As seen in FIG. 12, retrieval device 400 includes an articulating handle 410, semi-flexible sheath 414, actuating shaft 418 with grasping hook 420 at the distal end. Semi-flexible sheath 414 may be a stainless steel tube with a laser cut pattern in a distal region 416 for increased flexibility. The distal region 416 may be from about 3 to about 8 inches, alternatively from about 3 to about 7 inches, alternatively from about 4 to about 7 inches, alternatively from about 3 to about 6 inches from a distal end of the semi-flexible sheath 414. The laser cut pattern can allow for maneuverability when used through the working length of the delivery device 103. Within the semi-flexible sheath 414 is an actuating shaft 418 that is configured to move axially relative to the sheath 410 when the device handle 410 is articulated. The actuating shaft 418 may also be semi-flexible such that it can flex and maneuver when used through the working channel of the delivery device 103. Grasping hook 420 is located at the distal end of the actuating shaft 418. The atraumatic grasping hook 420 extends beyond the distal end of sheath 414 and can be visible via an imaging device when the retrieval device handle is in the "open" position. The grasping hook 420 can be withdrawn and recessed into sheath 414 when the articulating handle 410 is in the "closed" position.

As seen in FIGS. 15A-15C, the hook 420 may be shaped to enable visualization of the implant. As seen in FIG. 15C, a tip 428 of the hook may be narrower than a back portion 430 of the hook. The hook 420 may have a cross-sectional shape in which a back-side portion 430 of the cross-sectional shape is wider than a front-side portion 428. A width of the tip 428 of the hook may be between about 0.015" to about 0.050", alternatively between about 0.010" to about 0.040", alternatively between about 0.01" to about 0.030". The width of the front side portion 428 of the hook may be about ⅓ to about ⅔, alternatively about ¼ to about ¾, alternatively about ½ narrower than the largest width of the back-side portion 430.

Figure 14:
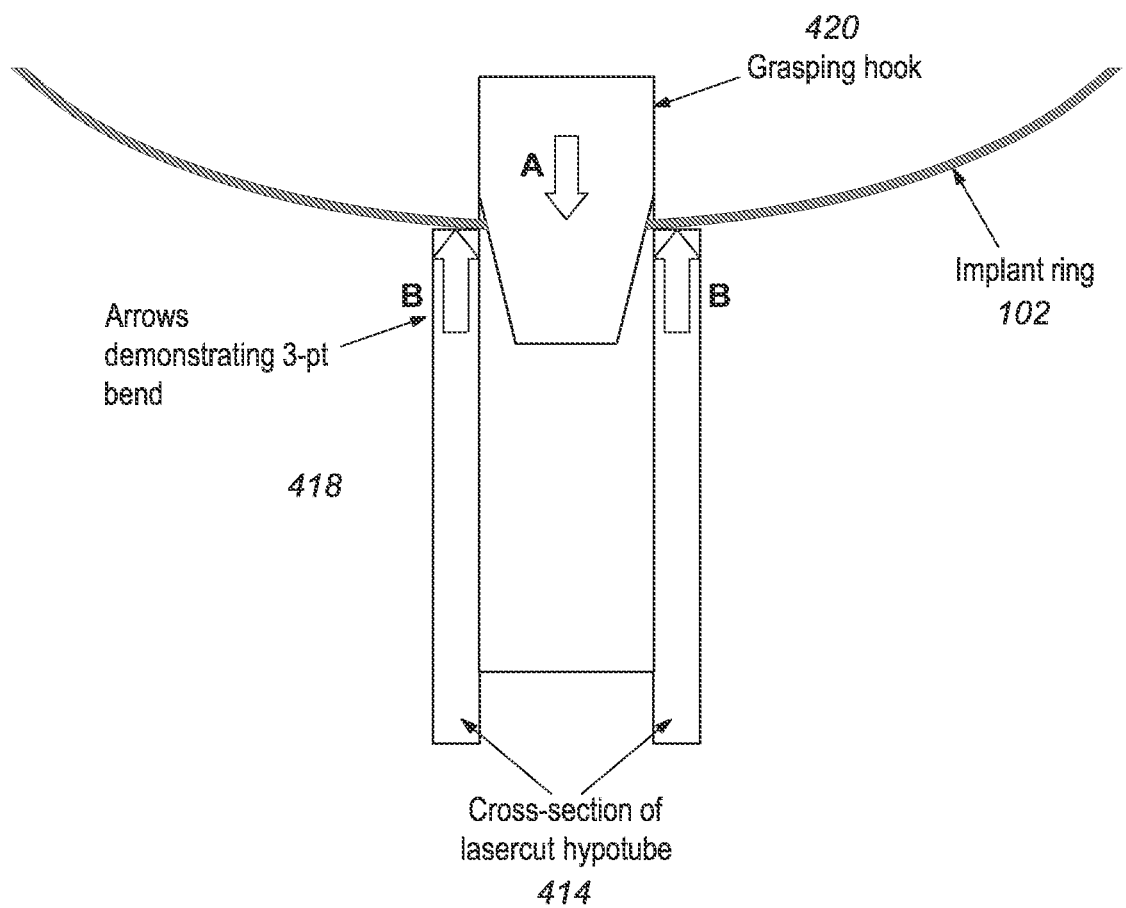
FIG. 14 is a depiction of forces applied to make a three-point bend.

Sheath 414 of retrieval device 400 is intended to be inserted into the first inner lumen 121 of outer tubular member 120 and maneuvered to the implant 102 to be removed. The grasping hook 420 may grasp any portion of the implant 102. For instance, the grasping hook 420 may grasp the implant anywhere along the elongate wire of the implant 102. The implant 102 has been "grasped" when any portion of it is inside the slot of the grasping hook 420 (see FIGS. 13A-13D). Once the implant is engaged by the grasping hook 420, the user may articulate the device handle 410. As seen in FIG. 14, articulation of the device handle 410 from an open to a closed position applies a 3-point bend to the grasped portion of the implant. The 3-point bend may be caused by force applied to the implant 102 by the outside wall 422 of the sheath 414 (see arrows in direction B) as the grasping hook 420 is withdrawn into the sheath 414 (see arrow in direction A). As force is applied to the device handle and the grasping hook is retracted, the implant effectively crimps due to the force of the 3-point bend. The grasping hook 420 and implant 102 are also partially withdrawn into the semi-flexible sheath. This action can induce high strain, which can permanently deform the implant. Once the handle has been fully articulated to a closed position and the implant is crimped and partially withdrawn the sheath 414, the implant 102 can be pulled from the lumen 121 and removed from the patient. The mechanism of removal relies on a "double lineation" of the implant; the wire on each side of the crimped hook straightens to substantially linear shapes as the retrieval device is pulled backward through the scope working channel. The sheath 414 may be a hypotube, e.g., a lasercut hypotube. In other embodiments, the sheath 414 may include a rigid member disposed over a distal region of the sheath 414, where the rigid member has compressive support and is sufficiently rigid to apply two counter forces to the implant 102 to form the 3-point bend. The rigid member may be tubular or non-tubular in shape.

The embodiments described herein are restated and expanded upon in the following paragraphs without explicit reference to the figures.

In many embodiments, a method of removing an implant from the urethra of a patient is described, the method including: advancing a portion of a removal device within a urethra of a patient to a position near the implant, wherein the removal device comprises an outer tubular member, an inner elongate tubular member within a lumen of the outer tubular member, and an elongate actuating member within a lumen of the inner elongate tubular member, the elongate actuating member having a proximal end coupled to a handle and a distal end comprising a hook; advancing the distal end of the elongate actuating member distal of a distal end of the outer tubular member and distal of a distal end of the inner elongate tubular member; grasping a portion of the implant with the hook; proximally withdrawing the hook and at least a portion of the implant into the lumen of the inner elongate tubular member such that a bend forms in the implant; and withdrawing the implant through the lumen of the outer tubular member, wherein the implant is in an axially elongate shape while in the lumen of the inner elongate tubular member.

In some embodiments, the implant has a first end, a second end, and a middle portion, and wherein the hook grasps the implant in the middle portion.

In some embodiments, the implant comprises an elongate wire and at least one enlarged end, and wherein the hook grasps the elongate wire.

In some embodiments, the inner elongate tubular member comprises a flexible distal region. In some embodiments, the flexible distal region comprises a laser cut tube.

In some embodiments, the inner elongate tubular member is a hypotube.

In some embodiments, the removal device further includes a rigid member disposed over a distal region of the inner elongate tubular member.

In some embodiments, a three-point bend forms in the implant.

In some embodiments, a bend forms in the implant as a result of a force applied to the implant by a wall of the inner elongate tubular member and the hook.

In some embodiments, the axially elongate shape includes a double lineation of the implant.

In some embodiments, the method further includes the step of viewing the hook with an imaging device after the hook is advanced distally beyond the distal end of the outer tubular member.

In some embodiments, the hook and the at least a portion of the implant are proximally withdrawn by actuating the handle coupled to the proximal end of the elongate actuating member.

In some embodiments, the implant has an expanded helical shape.

In some embodiments, a tip of the hook has a width between about 0.015" to about 0.050".

In some embodiments, a tip portion of the hook is narrower than a back portion of the hook.

In many embodiments, a system for retrieving an implant is described, the system includes a retrieval device including: an outer tubular member having a distal end and a lumen; an inner elongate tubular member within the lumen of the outer tubular member; an elongate actuating member within a lumen of the inner elongate tubular member, the elongate actuating member having a proximal end coupled to a handle and a distal end comprising a hook; and a proximal control device coupled with the inner tubular member and releasably coupled with the outer tubular member through a coupling mechanism, where the proximal control device is configured to longitudinally move the inner elongate tubular member, the outer tubular member, and the elongate actuating member, and also configured to move the elongate actuating member within the lumen of the inner elongate tubular member.

In some embodiments, the implant has a first end, a second end, and a middle portion, and wherein the hook is configured to grasp the implant in the middle portion.

In some embodiments, the inner elongate tubular member comprises a flexible distal region. In some embodiments, the flexible distal region comprises a laser cut tube.

In some embodiments, the inner elongate tubular member is a hypotube.

In some embodiments, the system further includes a rigid member disposed over a distal region of the inner elongate tubular member.

In some embodiments, the outer tubular member further comprises an imaging device located in a distal end region of the outer tubular member.

In some embodiments, the proximal control device is configured to longitudinally move the inner elongate tubular member, the outer tubular member, and the elongate actuating member concurrently.

In some embodiments, the implant has an expanded helical shape.

In many embodiments, a method of removing an implant from the urethra of a patient is described, the method including: advancing a removal device within a urethra of a patient to a position near the implant, wherein the removal device comprises an outer tubular member, an inner elongate tubular member within a lumen of the outer tubular member, an elongate actuating member within a lumen of the inner elongate tubular member, the elongate actuating member comprising a proximal end and a distal end, wherein the distal end comprises opposed first and second jaws configured to open and close; advancing the distal end of the elongate actuating member distal of a distal end of the inner elongate tubular member; grasping a portion of the implant with the opposed first and second jaws; and proximally withdrawing the elongate actuating member in the lumen of the inner elongate tubular member, wherein at least a portion of the implant assumes an axially elongated shape within the lumen of the inner elongate tubular member.

In some embodiments, the opposed first and second jaws grasp an enlarged end of the implant. In some embodiments, the shape of the enlarged end is can be a ball, a cylinder, or a cone. In some embodiments, the opposed first and second jaws are in a closed configuration, the opposed first and second jaws have an opening at a distal end of the closed configuration. In some embodiments, the implant includes an elongate wire and at least one enlarged end, and where the at least one enlarged end is grasped by the opposed first and second jaws, and where the elongate wire extends through the opening at the distal end of the closed configuration.

In some embodiments, the implant is in an axially elongate shape while in the lumen of the outer tubular member. In some embodiments, the axially elongated shape is substantially linear.

In some embodiments, the method further includes the step of viewing the distal end of the elongate actuating member with an imaging device after the distal end of the elongate actuating member is advanced distally beyond the distal end of the outer tubular member.

In some embodiments, the implant has an expanded helical shape.

In some embodiments, a tip of the hook has a width between about 0.015" to about 0.050".

In some embodiments, a tip portion of the hook is narrower than a back portion of the hook.

In many embodiments, a system for retrieving an implant is described, the system including: a retrieval device including: an outer tubular member having a distal end and a lumen; an inner elongate tubular member within the lumen of the outer tubular member; an elongate actuating member within a lumen of the inner elongate tubular member, the elongate actuating member comprising a proximal end and a distal end, wherein the distal end comprises first and second jaws configured to open and close; and a proximal control device coupled with the elongate actuating member and the inner elongate tubular member, and releasably coupled with the outer tubular member through a coupling mechanism, where the proximal control device is configured to longitudinally move the elongate actuating member, inner elongate tubular member, and the outer tubular member, and also configured to move the elongate actuating member longitudinally within the lumen of the inner tubular member.

In some embodiments, the implant has a first end, a second end, and a middle portion, and wherein at least one of the first and second ends is an enlarged atraumatic end. In some embodiments, the opposed first and second jaws are configured to grasp the enlarged atraumatic end of the implant.

In some embodiments, the opposed first and second jaws, when in a closed configuration, have an opening at a distal end of the closed configuration. In some embodiments, the implant comprises an elongate wire and at least one enlarged end, and wherein the opposed first and second jaws are configured to grasp the at least one enlarged end, and wherein the opening at the distal end of the closed configuration is configured for the elongate wire to extend therethrough.

In some embodiments, the outer tubular member further comprises an imaging device located in a distal end region of the outer tubular member.

In some embodiments, the proximal control device is configured to longitudinally move the elongate member, inner elongate member, and the outer tubular member concurrently.

In some embodiments, the implant has an expanded helical shape.

In many embodiments, a method of removing an implant from the urethra of a patient is described, the method including: advancing a removal device within a urethra of a patient to a position near the implant, wherein the removal device comprises an outer tubular member, an inner elongate tubular member within a lumen of the outer tubular member, an elongate actuating member within a lumen of the inner elongate tubular member, the elongate actuating member comprising a proximal end and a distal end, wherein the distal end comprises a grasper; advancing the distal end of the elongate actuating member distal of a distal end of the inner elongate tubular member; grabbing a portion of the implant with the grasper; and proximally withdrawing the elongate actuating member in the lumen of the inner elongate tubular member, wherein at least a portion of the implant assumes an axially elongated shape within the lumen of the inner elongate tubular member.

In some embodiments, the grasper comprises opposed first and second jaws. In some embodiments, the opposed first and second jaws grab an enlarged end of the implant. In some embodiments, the opposed first and second jaws are in a closed configuration, the opposed first and second jaws have an opening at a distal end of the closed configuration. In some embodiments, the implant comprises an elongate wire and at least one enlarged end, and wherein the at least one enlarged end is grabbed by the opposed first and second jaws, and wherein the elongate wire extends through the opening at the distal end of the closed configuration. In some embodiments, the axially elongated shape is substantially linear.

In some embodiments, the grasper comprises a hook. In some embodiments, the implant has a first end, a second end, and a middle portion, and wherein the hook grasps the implant in the middle portion. In some embodiments, the implant comprises an elongate wire and at least one enlarged end, and wherein the hook grasps the elongate wire. In some embodiments, the inner elongate tubular member comprises a flexible distal region. In some embodiments, the flexible distal region comprises a laser cut tube. In some embodiments, the inner elongate tubular member is a hypotube. In some embodiments, the removal device further includes a rigid member disposed over a distal region of the inner elongate tubular member. In some embodiments, when the hook and the portion of the implant are proximally withdrawn in the lumen of the inner elongate tubular member, a bend forms in the implant. In some embodiments, the bend is a three-point bend. In some embodiments, the bend forms in the implant as a result of a plurality of forces applied to the implant by a wall of the inner elongate tubular member and the hook. In some embodiments, the axially elongate shape includes a double lineation of the implant. In some embodiments, the method further includes the step of viewing the hook with an imaging device after the hook is advanced distally beyond the distal end of the outer tubular member.

In some embodiments, the implant has an expanded helical shape.

In some embodiments, a tip of the hook has a width between about 0.015" to about 0.050".

In some embodiments, a tip portion of the hook is narrower than a back portion of the hook.

In many embodiments, a system for retrieving an implant is described, the system including a retrieval device including: an outer tubular member having a distal end and a lumen; an inner elongate tubular member within the lumen of the outer tubular member; an elongate actuating member within a lumen of the inner elongate tubular member, the elongate actuating member comprising a proximal end and a distal end, wherein the distal end comprises a grasper; and a proximal control device coupled with the elongate actuating member and the inner elongate actuating member, and releasably coupled with the outer tubular member through a coupling mechanism, wherein the proximal control device is configured to longitudinally move the elongate actuating member, inner elongate tubular member, and the outer tubular member, and also configured to move the elongate actuating member longitudinally within the lumen of the inner tubular member.

In some embodiments, the grasper comprises opposed first and second jaws. In some embodiments, the implant has a first end, a second end, and a middle portion, and wherein at least one of the first and second ends is an enlarged atraumatic end. In some embodiments, the opposed first and second jaws are configured to grasp the enlarged atraumatic end of the implant. In some embodiments, the opposed first and second jaws, when in a closed configuration, have an opening at a distal end of the closed configuration. In some embodiments, the implant comprises an elongate wire and at least one enlarged end, and wherein the opposed first and second jaws are configured to grasp the at least one enlarged end, and wherein the opening at the distal end of the closed configuration is configured for the elongate wire to extend therethrough.

In some embodiments, the outer tubular member further comprises an imaging device located in a distal end region of the outer tubular member.

In some embodiments, the proximal control device is configured to longitudinally move the elongate member, inner elongate member, and the outer tubular member concurrently.

In some embodiments, the grasper comprises a hook. In some embodiments, the implant has a first end, a second end, and a middle portion, and wherein the hook is configured to grasp the implant in the middle portion. In some embodiments, the inner elongate tubular member comprises a flexible distal region. In some embodiments, the inner elongate tubular member is a hypotube. In some embodiments, the system further includes a rigid member disposed over a distal region of the inner elongate tubular member. In some embodiments, the flexible distal region comprises a laser cut tube. In some embodiments, the implant has an expanded helical shape. In some embodiments, a tip of the hook has a width between about 0.015" to about 0.050". In some embodiments, a tip portion of the hook is narrower than a back portion of the hook.

Systems, devices, and methods are provided for retrieval of an implant from the prostatic urethra. Embodiments of retrieval systems can include a device for insertion into the patient and a proximal control device for use in grasping a portion of the implant and withdrawing the implant into a lumen of the retrieval system.

Aspects of the invention are set out in the independent claims and preferred features are set out in the dependent claims. Preferred features of each aspect may be provided in combination with each other within particular embodiments and may also be provided in combination with other aspects.

Clauses

Exemplary embodiments are set out in the following numbered clauses.

Clause 1. A method of removing an implant from the urethra of a patient, the method comprising: advancing a portion of a removal device within a urethra of a patient to a position near the implant, wherein the removal device comprises an outer tubular member, an inner elongate tubular member within a lumen of the outer tubular member, and an elongate actuating member within a lumen of the inner elongate tubular member, the elongate actuating member having a proximal end coupled to a handle and a distal end comprising a hook; advancing the distal end of the elongate actuating member distal of a distal end of the outer tubular member and distal of a distal end of the inner elongate tubular member; grasping a portion of the implant with the hook; proximally withdrawing the hook and at least a portion of the implant into the lumen of the inner elongate tubular member such that a bend forms in the implant; and withdrawing the implant through the lumen of the outer tubular member, wherein the implant is in an axially elongate shape while in the lumen of the inner elongate tubular member.

Clause 2. The method of clause 1, wherein the implant has a first end, a second end, and a middle portion, and wherein the hook grasps the implant in the middle portion.

Clause 3. The method of clause 1, wherein the implant comprises an elongate wire and at least one enlarged end, and wherein the hook grasps the elongate wire.

Clause 4. The method of clause 1, wherein the inner elongate tubular member comprises a flexible distal region.

Clause 5. The method of clause 4, wherein the flexible distal region comprises a laser cut tube.

Clause 6. The method of clause 1, wherein the inner elongate tubular member is a hypotube.

Clause 7. The method of clause 1, wherein the removal device further comprises a rigid member disposed over a distal region of the inner elongate tubular member.

Clause 8. The method of clause 1, wherein a three-point bend forms in the implant.

Clause 9. The method of clause 1, wherein a bend forms in the implant as a result of a force applied to the implant by a wall of the inner elongate tubular member and the hook.

Clause 10. The method of clause 1, wherein the axially elongate shape includes a double lineation of the implant.

Clause 11. The method of clause 1, further comprising the step of viewing the hook with an imaging device after the hook is advanced distally beyond the distal end of the outer tubular member.

Clause 12. The method of clause 1, wherein the hook and the at least a portion of the implant are proximally withdrawn by actuating the handle coupled to the proximal end of the elongate actuating member.

Clause 13. The method of clause 1, wherein the implant has an expanded helical shape.

Clause 14. The method of clause 1, wherein a tip of the hook has a width between about 0.015" to about 0.050".

Clause 15. The method of clause 1, wherein a tip portion of the hook is narrower than a back portion of the hook.

Clause 16. A system for retrieving an implant, the system comprising a retrieval device comprising: an outer tubular member having a distal end and a lumen; an inner elongate tubular member within the lumen of the outer tubular member; an elongate actuating member within a lumen of the inner elongate tubular member, the elongate actuating member having a proximal end coupled to a handle and a distal end comprising a hook; and a proximal control device coupled with the inner tubular member and releasably coupled with the outer tubular member through a coupling mechanism, wherein the proximal control device is configured to longitudinally move the inner elongate tubular member, the outer tubular member, and the elongate actuating member, and also configured to move the elongate actuating member within the lumen of the inner elongate tubular member.

Clause 17. The system of clause 16, wherein the implant has a first end, a second end, and a middle portion, and wherein the hook is configured to grasp the implant in the middle portion.

Clause 18. The system of clause 16, wherein the inner elongate tubular member comprises a flexible distal region.

Clause 19. The system of clause 16, wherein the inner elongate tubular member is a hypotube.

Clause 20. The system of clause 16, wherein the system further comprises a rigid member disposed over a distal region of the inner elongate tubular member.

Clause 21. The system of clause 18, wherein the flexible distal region comprises a laser cut tube.

Clause 22. The system of clause 16, wherein the outer tubular member further comprises an imaging device located in a distal end region of the outer tubular member.

Clause 23. The system of clause 16, wherein the proximal control device is configured to longitudinally move the inner elongate tubular member, the outer tubular member, and the elongate actuating member concurrently.

Clause 24. The system of clause 16, wherein the implant has an expanded helical shape.

Clause 25. The system of clause 16, wherein a tip of the hook has a width between about 0.015" to about 0.050".

Clause 26. The system of clause 16, wherein a tip portion of the hook is narrower than a back portion of the hook.

Clause 27. A method of removing an implant from the urethra of a patient, the method comprising: advancing a removal device within a urethra of a patient to a position near the implant, wherein the removal device comprises an outer tubular member, an inner elongate tubular member within a lumen of the outer tubular member, an elongate actuating member within a lumen of the inner elongate tubular member, the elongate actuating member comprising a proximal end and a distal end, wherein the distal end comprises opposed first and second jaws configured to open and close; advancing the distal end of the elongate actuating member distal of a distal end of the inner elongate tubular member; grasping a portion of the implant with the opposed first and second jaws; and proximally withdrawing the elongate actuating member in the lumen of the inner elongate tubular member, wherein at least a portion of the implant assumes an axially elongated shape within the lumen of the inner elongate tubular member.

Clause 28. The method of clause 27, wherein the opposed first and second jaws grasp an enlarged end of the implant.

Clause 29. The method of clause 28, wherein the enlarged end is in a shape selected from the group consisting of a ball, a cylinder, and a cone.

Clause 30. The method of clause 28, wherein when the opposed first and second jaws are in a closed configuration, the opposed first and second jaws have an opening at a distal end of the closed configuration.

Clause 31. The method of clause 30, wherein the implant comprises an elongate wire and at least one enlarged end, and wherein the at least one enlarged end is grasped by the opposed first and second jaws, and wherein the elongate wire extends through the opening at the distal end of the closed configuration.

Clause 32. The method of clause 27, wherein the implant is in an axially elongate shape while in the lumen of the outer tubular member.

Clause 33. The method of clause 32, wherein the axially elongated shape is substantially linear.

Clause 34. The method of clause 27, further comprising the step of viewing the distal end of the elongate actuating member with an imaging device after the distal end of the elongate actuating member is advanced distally beyond the distal end of the outer tubular member.

Clause 35. The method of clause 27, wherein the implant has an expanded helical shape.

Clause 36. A system for retrieving an implant, the system comprising a retrieval device comprising: an outer tubular member having a distal end and a lumen; an inner elongate tubular member within the lumen of the outer tubular member; an elongate actuating member within a lumen of the inner elongate tubular member, the elongate actuating member comprising a proximal end and a distal end, wherein the distal end comprises first and second jaws configured to open and close; and a proximal control device coupled with the elongate actuating member and the inner elongate tubular member, and releasably coupled with the outer tubular member through a coupling mechanism, wherein the proximal control device is configured to longitudinally move the elongate actuating member, inner elongate tubular member, and the outer tubular member, and also configured to move the elongate actuating member longitudinally within the lumen of the inner tubular member.

Clause 37. The system of clause 36, wherein the implant has a first end, a second end, and a middle portion, and wherein at least one of the first and second ends is an enlarged atraumatic end.

Clause 38. The system of clause 37, wherein the opposed first and second jaws are configured to grasp the enlarged atraumatic end of the implant.

Clause 39. The system of clause 36, wherein the opposed first and second jaws, when in a closed configuration, have an opening at a distal end of the closed configuration.

Clause 40. The system of clause 39, wherein the implant comprises an elongate wire and at least one enlarged end, and wherein the opposed first and second jaws are configured to grasp the at least one enlarged end, and wherein the opening at the distal end of the closed configuration is configured for the elongate wire to extend therethrough.

Clause 41. The system of clause 36, wherein the outer tubular member further comprises an imaging device located in a distal end region of the outer tubular member.

Clause 42. The system of clause 36, wherein the proximal control device is configured to longitudinally move the elongate member, inner elongate member, and the outer tubular member concurrently.

Clause 43. The system of clause 36, wherein the implant has an expanded helical shape.

Clause 44. A method of removing an implant from the urethra of a patient, the method comprising: advancing a removal device within a urethra of a patient to a position near the implant, wherein the removal device comprises an outer tubular member, an inner elongate tubular member within a lumen of the outer tubular member, an elongate actuating member within a lumen of the inner elongate tubular member, the elongate actuating member comprising a proximal end and a distal end, wherein the distal end comprises a grasper; advancing the distal end of the elongate actuating member distal of a distal end of the inner elongate tubular member; grabbing a portion of the implant with the grasper; and proximally withdrawing the elongate actuating member in the lumen of the inner elongate tubular member, wherein at least a portion of the implant assumes an axially elongated shape within the lumen of the inner elongate tubular member.

Clause 45. The method of clause 44, wherein the grasper comprises opposed first and second jaws.

Clause 46. The method of clause 45, wherein the opposed first and second jaws grab an enlarged end of the implant.

Clause 47. The method of clause 45, wherein when the opposed first and second jaws are in a closed configuration, the opposed first and second jaws have an opening at a distal end of the closed configuration.

Clause 48. The method of clause 47, wherein the implant comprises an elongate wire and at least one enlarged end, and wherein the at least one enlarged end is grabbed by the opposed first and second jaws, and wherein the elongate wire extends through the opening at the distal end of the closed configuration.

Clause 49. The method of clause 45, wherein the axially elongated shape is substantially linear.

Clause 50. The method of clause 44, wherein the grasper comprises a hook.

Clause 51. The method of clause 50, wherein the implant has a first end, a second end, and a middle portion, and wherein the hook grasps the implant in the middle portion.

Clause 52. The method of clause 50, wherein the implant comprises an elongate wire and at least one enlarged end, and wherein the hook grasps the elongate wire.

Clause 53. The method of clause 50, wherein a tip of the hook has a width between about 0.015" to about 0.050".

Clause 54. The method of clause 50, wherein a tip portion of the hook is narrower than a back portion of the hook.

Clause 55. The method of clause 50, wherein the inner elongate tubular member comprises a flexible distal region.

Clause 56. The method of clause 55, wherein the flexible distal region comprises a laser cut tube.

Clause 57. The method of clause 50, wherein the inner elongate tubular member is a hypotube.

Clause 58. The method of clause 50, wherein the removal device further comprises a rigid member disposed over a distal region of the inner elongate tubular member.

Clause 59. The method of clause 50, wherein when the hook and the portion of the implant are proximally withdrawn in the lumen of the inner elongate tubular member, a bend forms in the implant.

Clause 60. The method of clause 59, wherein the bend is a three-point bend.

Clause 61. The method of clause 59, wherein the bend forms in the implant as a result of a plurality of forces applied to the implant by a wall of the inner elongate tubular member and the hook.

Clause 62. The method of clause 50, wherein the axially elongate shape includes a double lineation of the implant.

Clause 63. The method of clause 50, further comprising the step of viewing the hook with an imaging device after the hook is advanced distally beyond the distal end of the outer tubular member.

Clause 64. The method of clause 44, wherein the implant has an expanded helical shape.

Clause 65. A system for retrieving an implant, the system comprising a retrieval device comprising: an outer tubular member having a distal end and a lumen; an inner elongate tubular member within the lumen of the outer tubular member; an elongate actuating member within a lumen of the inner elongate tubular member, the elongate actuating member comprising a proximal end and a distal end, wherein the distal end comprises a grasper; and a proximal control device coupled with the elongate actuating member and the inner elongate actuating member, and releasably coupled with the outer tubular member through a coupling mechanism, wherein the proximal control device is configured to longitudinally move the elongate actuating member, inner elongate tubular member, and the outer tubular member, and also configured to move the elongate actuating member longitudinally within the lumen of the inner tubular member.

Clause 66. The system of clause 65, wherein the grasper comprises opposed first and second jaws.

Clause 67. The system of clause 66, wherein the implant has a first end, a second end, and a middle portion, and wherein at least one of the first and second ends is an enlarged atraumatic end.

Clause 68. The system of clause 67, wherein the opposed first and second jaws are configured to grasp the enlarged atraumatic end of the implant.

Clause 69. The system of clause 66, wherein the opposed first and second jaws, when in a closed configuration, have an opening at a distal end of the closed configuration.

Clause 70. The system of clause 69, wherein the implant comprises an elongate wire and at least one enlarged end, and wherein the opposed first and second jaws are configured to grasp the at least one enlarged end, and wherein the opening at the distal end of the closed configuration is configured for the elongate wire to extend therethrough.

Clause 71. The system of clause 65, wherein the outer tubular member further comprises an imaging device located in a distal end region of the outer tubular member.

Clause 72. The system of clause 65, wherein the proximal control device is configured to longitudinally move the elongate member, inner elongate member, and the outer tubular member concurrently.

Clause 73. The system of clause 65, wherein the grasper comprises a hook.

Clause 74. The system of clause 73, wherein the implant has a first end, a second end, and a middle portion, and wherein the hook is configured to grasp the implant in the middle portion.

Clause 75. The system of clause 73, wherein a tip of the hook has a width between about 0.01 Clause 5" to about 0.050".

Clause 76. The system of clause 73, wherein a tip portion of the hook is narrower than a back portion of the hook.

Clause 77. The system of clause 73, wherein the inner elongate tubular member comprises a flexible distal region.

Clause 78. The system of clause 77, wherein the flexible distal region comprises a laser cut tube.

Clause 79. The system of clause 73, wherein the inner elongate tubular member is a hypotube.

Clause 80. The system of clause 73, wherein the system further comprises a rigid member disposed over a distal region of the inner elongate tubular member.

Clause 81. The system of clause 65, wherein the implant has an expanded helical shape.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of removing an implant from the urethra of a patient, the method comprising:
    advancing a removal device within a urethra of a patient to a position near the implant, wherein the implant comprises a first portion, a second portion, and a third portion between the first portion and the second portion, wherein the removal device comprises an outer tubular member, an inner elongate tubular member within a lumen of the outer tubular member, an elongate actuating member within a lumen of the inner elongate tubular member, the elongate actuating member comprising a proximal end and a distal end, wherein the distal end comprises a grasper;
    advancing the distal end of the elongate actuating member distal of a distal end of the inner elongate tubular member;
    grabbing the third portion of the implant with the grasper; and
    proximally withdrawing the elongate actuating member in the lumen of the inner elongate tubular member forming a bend in the third portion, wherein the first portion and the second portion of the implant are substantially straightened on either side of the bend within the lumen of the inner elongate tubular member.

2. The method of claim 1, wherein the grasper comprises a hook.

3. The method of claim 2, wherein the implant comprises an elongate wire and at least one enlarged end, and wherein the hook grasps the elongate wire.

4. The method of claim 2, wherein a tip of the hook has a width between about 0.015" to about 0.050".

5. The method of claim 2, wherein a tip portion of the hook is narrower than a back portion of the hook.

6. The method of claim 2, wherein the inner elongate tubular member comprises a flexible distal region.

7. The method of claim 6, wherein the flexible distal region comprises a laser cut tube.

8. The method of claim 2, wherein the inner elongate tubular member is a hypotube.

9. The method of claim 2, wherein the removal device further comprises a rigid member disposed over a distal region of the inner elongate tubular member.

10. The method of claim 2, further comprising the step of viewing the hook with an imaging device after the hook is advanced distally beyond the distal end of the outer tubular member.

11. The method of claim 1, wherein the bend forms in the implant as a result of a plurality of forces applied to the implant by a wall of the inner elongate tubular member and the hook.

12. The method of claim 1, wherein the implant has an expanded helical shape.

* * * * *